US009994851B2

(12) United States Patent
Wilton et al.

(10) Patent No.: US 9,994,851 B2
(45) Date of Patent: *Jun. 12, 2018

(54) ANTISENSE OLIGONUCLEOTIDES FOR INDUCING EXON SKIPPING AND METHODS OF USE THEREOF

(71) Applicant: The University of Western Australia, Crawley (AU)

(72) Inventors: Stephen Donald Wilton, Applecross (AU); Sue Fletcher, Bayswater (AU); Graham McClorey, Bayswater (AU)

(73) Assignee: The University of Western Australia, Crawley (AU)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/705,172

(22) Filed: Sep. 14, 2017

(65) Prior Publication Data
US 2018/0002697 A1 Jan. 4, 2018

Related U.S. Application Data

(63) Continuation of application No. 15/274,772, filed on Sep. 23, 2016, which is a continuation of application No. 14/740,097, filed on Jun. 15, 2015, now Pat. No. 9,605,262, which is a continuation of application No. 13/741,150, filed on Jan. 14, 2013, now abandoned, which is a continuation of application No. 13/168,857, filed on Jun. 24, 2011, now abandoned, which is a continuation of application No. 12/837,359, filed on Jul. 15, 2010, now Pat. No. 8,232,384, which is a continuation of application No. 11/570,691, filed as application No. PCT/AU2005/000943 on Jun. 28, 2005, now Pat. No. 7,807,816.

(30) Foreign Application Priority Data

Jun. 28, 2004 (AU) .................................. 2004903474

(51) Int. Cl.
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/3233* (2013.01); *C12N 2310/33* (2013.01); *C12N 2310/3341* (2013.01); *C12N 2310/3519* (2013.01); *C12N 2320/30* (2013.01); *C12N 2320/33* (2013.01)

(58) Field of Classification Search
CPC .................................................... C07H 21/04
See application file for complete search history.

(56) References Cited

U.S. PATENT DOCUMENTS

| | | | |
|---|---|---|---|
| 4,458,066 A | 7/1984 | Caruthers et al. | |
| 5,034,506 A | 7/1991 | Summerton et al. | |
| 5,138,045 A | 8/1992 | Cook et al. | |
| 5,142,047 A | 8/1992 | Summerton et al. | |
| 5,149,797 A | 9/1992 | Pederson et al. | |
| 5,166,315 A | 11/1992 | Summerton et al. | |
| 5,185,444 A | 2/1993 | Summerton et al. | |
| 5,190,931 A | 3/1993 | Inouye | |
| 5,217,866 A | 6/1993 | Summerton et al. | |
| 5,506,337 A | 4/1996 | Summerton et al. | |
| 5,521,063 A | 5/1996 | Summerton et al. | |
| 5,627,274 A | 5/1997 | Kole et al. | |
| 5,665,593 A | 9/1997 | Kole et al. | |
| 5,698,685 A | 12/1997 | Summerton et al. | |
| 5,801,154 A | 9/1998 | Baracchini et al. | |
| 5,869,252 A | 2/1999 | Bouma et al. | |
| 5,892,023 A | 4/1999 | Pirotzky et al. | |
| 5,916,808 A | 6/1999 | Kole et al. | |
| 5,976,879 A | 11/1999 | Kole et al. | |
| 6,153,436 A | 11/2000 | Hermonat et al. | |
| 6,210,892 B1 | 4/2001 | Bennett et al. | |
| 6,312,900 B1 | 11/2001 | Dean et al. | |
| 6,391,636 B1 | 5/2002 | Monia | |
| 6,451,991 B1 | 9/2002 | Martin et al. | |
| 6,653,466 B2 | 11/2003 | Matsuo | |
| 6,653,467 B1 | 11/2003 | Matsuo et al. | |
| 6,656,732 B1 | 12/2003 | Bennett et al. | |
| 6,727,355 B2 | 4/2004 | Matsuo et al. | |
| 6,784,291 B2 | 8/2004 | Iversen et al. | |
| 6,806,084 B1 | 10/2004 | Debs et al. | |
| 7,001,761 B2 | 2/2006 | Xiao | |
| 7,070,807 B2 | 7/2006 | Mixson | |
| 7,163,695 B2 | 1/2007 | Mixson | |
| 7,250,289 B2 | 7/2007 | Zhou | |
| 7,314,750 B2 | 1/2008 | Zhou | |
| 7,468,418 B2 | 12/2008 | Iversen et al. | |
| 7,534,879 B2 | 5/2009 | van Deutekom | |
| 7,655,785 B1 | 2/2010 | Bentwich | |
| 7,655,788 B2 | 2/2010 | Khvorova et al. | |
| 7,807,816 B2 | 10/2010 | Wilton et al. | |
| 7,902,160 B2 | 3/2011 | Matsuo et al. | |
| 7,960,541 B2 | 6/2011 | Wilton et al. | |
| 7,973,015 B2 | 7/2011 | van Ommen et al. | |
| 8,084,601 B2 | 12/2011 | Popplewell et al. | |
| 8,232,384 B2 | 7/2012 | Wilton et al. | |
| 8,324,371 B2 | 12/2012 | Popplewell et al. | |

(Continued)

FOREIGN PATENT DOCUMENTS

AU 2003284638 A1 6/2004
AU 780517 B2 3/2005

(Continued)

OTHER PUBLICATIONS

"Efficacy Study of AVI-4658 to Induce Dystrophin Expression in Selected Duchenne Muscular Dystrophy Patients" ClinicalTrials.gov dated Jan. 22, 2013.

(Continued)

*Primary Examiner* — Kimberly Chong
(74) *Attorney, Agent, or Firm* — Sterne, Kessler, Goldstein & Fox P.L.L.C.

(57) ABSTRACT

An antisense molecule capable of binding to a selected target site to induce exon skipping in the dystrophin gene, as set forth in SEQ ID NO: 1 to 214.

2 Claims, 22 Drawing Sheets

(56) References Cited

U.S. PATENT DOCUMENTS

| | | |
|---|---|---|
| 8,361,979 B2 | 1/2013 | Aartsma-Rus et al. |
| 8,436,163 B2 | 5/2013 | Iversen et al. |
| 8,450,474 B2 | 5/2013 | Wilton et al. |
| 8,455,634 B2 | 6/2013 | Wilton et al. |
| 8,455,635 B2 | 6/2013 | Wilton et al. |
| 8,455,636 B2 | 6/2013 | Wilton et al. |
| 8,461,325 B2 | 6/2013 | Popplewell et al. |
| 8,476,423 B2 | 7/2013 | Wilton et al. |
| 8,486,907 B2 | 7/2013 | Wilton et al. |
| 8,501,703 B2 | 8/2013 | Bennett et al. |
| 8,501,704 B2 | 8/2013 | Mourich et al. |
| 8,524,676 B2 | 9/2013 | Stein et al. |
| 8,524,880 B2 | 9/2013 | Wilton et al. |
| 8,536,147 B2 | 9/2013 | Weller et al. |
| 8,552,172 B2 | 10/2013 | Popplewell et al. |
| 8,592,386 B2 | 11/2013 | Mourich et al. |
| 8,618,270 B2 | 12/2013 | Iversen et al. |
| 8,624,019 B2 | 1/2014 | Matsuo et al. |
| 8,637,483 B2 | 1/2014 | Wilton et al. |
| 8,697,858 B2 | 4/2014 | Iversen |
| 8,741,863 B2 | 6/2014 | Moulton et al. |
| 8,759,307 B2 | 6/2014 | Stein et al. |
| 8,759,507 B2 | 6/2014 | Van Deutekorn |
| 8,779,128 B2 | 7/2014 | Hanson et al. |
| 8,785,407 B2 | 7/2014 | Stein et al. |
| 8,785,410 B2 | 7/2014 | Iversen et al. |
| 8,835,402 B2 | 9/2014 | Kole et al. |
| 8,865,883 B2 | 10/2014 | Sazani et al. |
| 8,871,918 B2 | 10/2014 | Sazani et al. |
| 8,877,725 B2 | 11/2014 | Iversen et al. |
| 8,895,722 B2 | 11/2014 | Iversen et al. |
| 8,906,872 B2 | 12/2014 | Iversen et al. |
| 9,018,368 B2 | 4/2015 | Wilton et al. |
| 9,024,007 B2 | 5/2015 | Wilton et al. |
| 9,035,040 B2 | 5/2015 | Wilton et al. |
| 9,175,286 B2 | 11/2015 | Wilton et al. |
| 9,217,148 B2 | 12/2015 | Bestwick et al. |
| 9,228,187 B2 | 1/2016 | Wilton et al. |
| 9,234,198 B1 | 1/2016 | Sazani et al. |
| 9,249,416 B2 | 2/2016 | Wilton et al. |
| 9,416,361 B2 | 8/2016 | Iversen et al. |
| 9,422,555 B2 | 8/2016 | Wilton et al. |
| 9,434,948 B2 | 9/2016 | Sazani et al. |
| 9,441,229 B2 | 9/2016 | Wilton et al. |
| 9,447,415 B2 | 9/2016 | Wilton et al. |
| 9,447,416 B2 | 9/2016 | Sazani et al. |
| 9,447,417 B2 | 9/2016 | Sazani et al. |
| 9,453,225 B2 | 9/2016 | Sazani et al. |
| 9,506,058 B2 | 11/2016 | Kaye |
| 9,605,262 B2 | 3/2017 | Wilton et al. |
| 9,758,783 B2 | 9/2017 | Wilton et al. |
| 2001/0056077 A1 | 12/2001 | Matsuo |
| 2002/0049173 A1 | 4/2002 | Bennett et al. |
| 2002/0055481 A1 | 5/2002 | Matsuo et al. |
| 2002/0110819 A1 | 8/2002 | Weller et al. |
| 2002/0156235 A1 | 10/2002 | Manoharan et al. |
| 2003/0166588 A1 | 9/2003 | Iversen et al. |
| 2003/0224353 A1 | 12/2003 | Stein et al. |
| 2003/0235845 A1 | 12/2003 | van Ommen et al. |
| 2004/0248833 A1 | 12/2004 | Emanuele et al. |
| 2004/0254137 A1 | 12/2004 | Ackermann et al. |
| 2004/0266720 A1 | 12/2004 | Iversen et al. |
| 2005/0026164 A1 | 2/2005 | Zhou |
| 2005/0048495 A1 | 3/2005 | Baker et al. |
| 2005/0153935 A1 | 7/2005 | Iversen et al. |
| 2006/0099616 A1 | 5/2006 | van Ommen et al. |
| 2006/0147952 A1 | 7/2006 | van Ommen et al. |
| 2006/0148740 A1 | 7/2006 | Platenburg |
| 2006/0287268 A1 | 12/2006 | Iversen et al. |
| 2007/0037165 A1 | 2/2007 | Venter et al. |
| 2007/0082861 A1 | 4/2007 | Matsuo et al. |
| 2007/0265215 A1 | 11/2007 | Iversen et al. |
| 2008/0194463 A1 | 8/2008 | Weller et al. |
| 2008/0200409 A1 | 8/2008 | Wilson et al. |
| 2008/0209581 A1 | 8/2008 | van Ommen et al. |
| 2009/0076246 A1 | 3/2009 | van Deutekom |
| 2009/0082547 A1 | 3/2009 | Iversen et al. |
| 2009/0088562 A1 | 4/2009 | Weller et al. |
| 2009/0099066 A1 | 4/2009 | Moulton et al. |
| 2009/0228998 A1 | 9/2009 | van Ommen et al. |
| 2009/0269755 A1 | 10/2009 | Aartsma-Rus et al. |
| 2009/0312532 A1 | 12/2009 | Van Eutekom et al. |
| 2010/0016215 A1 | 1/2010 | Moulton et al. |
| 2010/0130591 A1 | 5/2010 | Sazani et al. |
| 2010/0168212 A1 | 7/2010 | Popplewell et al. |
| 2011/0015253 A1 | 1/2011 | Wilton et al. |
| 2011/0015258 A1 | 1/2011 | Wilton et al. |
| 2011/0046203 A1 | 2/2011 | Wilton et al. |
| 2011/0046360 A1 | 2/2011 | Matsuo et al. |
| 2011/0110960 A1 | 5/2011 | Platenburg |
| 2011/0263682 A1 | 10/2011 | De Kimpe et al. |
| 2011/0263686 A1 | 10/2011 | Wilton et al. |
| 2011/0281787 A1 | 11/2011 | Lu et al. |
| 2011/0294753 A1 | 12/2011 | De Kimpe et al. |
| 2011/0312086 A1 | 12/2011 | Van Deutekom |
| 2012/0022134 A1 | 1/2012 | De Kimpe et al. |
| 2012/0022144 A1 | 1/2012 | Wilton et al. |
| 2012/0022145 A1 | 1/2012 | Wilton et al. |
| 2012/0029057 A1 | 2/2012 | Wilton et al. |
| 2012/0029058 A1 | 2/2012 | Wilton et al. |
| 2012/0029059 A1 | 2/2012 | Wilton et al. |
| 2012/0029060 A1 | 2/2012 | Wilton et al. |
| 2012/0041050 A1 | 2/2012 | Wilton et al. |
| 2012/0046342 A1 | 2/2012 | Van Deutekom et al. |
| 2012/0053228 A1 | 3/2012 | Iversen et al. |
| 2012/0059042 A1 | 3/2012 | Platenburg et al. |
| 2012/0065169 A1 | 3/2012 | Hanson et al. |
| 2012/0065244 A1 | 3/2012 | Popplewell et al. |
| 2012/0108652 A1 | 5/2012 | Popplewell et al. |
| 2012/0108653 A1 | 5/2012 | Popplewell et al. |
| 2012/0115150 A1 | 5/2012 | Bozzoni et al. |
| 2012/0122801 A1 | 5/2012 | Platenburg |
| 2012/0149756 A1 | 6/2012 | Schumperli et al. |
| 2012/0172415 A1 | 7/2012 | Voit et al. |
| 2012/0202752 A1 | 8/2012 | Lu |
| 2012/0289457 A1 | 11/2012 | Hanson |
| 2013/0072671 A1 | 3/2013 | Van Deutekom |
| 2013/0090465 A1 | 4/2013 | Matsu et al. |
| 2013/0116310 A1 | 5/2013 | Wilton et al. |
| 2013/0190390 A1 | 7/2013 | Sazani et al. |
| 2013/0197220 A1 | 8/2013 | Ueda |
| 2013/0211062 A1 | 8/2013 | Watanabe et al. |
| 2013/0217755 A1 | 8/2013 | Wilton et al. |
| 2013/0253033 A1 | 9/2013 | Wilton et al. |
| 2013/0253180 A1 | 9/2013 | Wilton et al. |
| 2013/0274313 A1 | 10/2013 | Wilton et al. |
| 2013/0289096 A1 | 10/2013 | Popplewell et al. |
| 2013/0302806 A1 | 11/2013 | Van Deutekorn |
| 2013/0331438 A1 | 12/2013 | Wilton et al. |
| 2014/0045916 A1 | 2/2014 | Iversen et al. |
| 2014/0057964 A1 | 2/2014 | Popplewell et al. |
| 2014/0080896 A1 | 3/2014 | Nelson et al. |
| 2014/0080898 A1 | 3/2014 | Wilton et al. |
| 2014/0094500 A1 | 4/2014 | Sazani et al. |
| 2014/0113955 A1 | 4/2014 | De Kimpe et al. |
| 2014/0128592 A1 | 5/2014 | De Kimpe et al. |
| 2014/0155587 A1 | 6/2014 | Wilton et al. |
| 2014/0213635 A1 | 7/2014 | Van Deutekom |
| 2014/0221458 A1 | 8/2014 | De Kimpe et al. |
| 2014/0243515 A1 | 8/2014 | Wilton et al. |
| 2014/0243516 A1 | 8/2014 | Wilton et al. |
| 2014/0275212 A1 | 9/2014 | van Deutekom |
| 2014/0296323 A1 | 10/2014 | Leumann et al. |
| 2014/0315862 A1 | 10/2014 | Kaye |
| 2014/0315977 A1 | 10/2014 | Bestwick et al. |
| 2014/0316123 A1 | 10/2014 | Matsuo et al. |
| 2014/0323544 A1 | 10/2014 | Bestwick et al. |
| 2014/0329762 A1 | 11/2014 | Kaye |
| 2014/0329881 A1 | 11/2014 | Bestwick et al. |
| 2014/0343266 A1 | 11/2014 | Watanabe et al. |
| 2014/0350067 A1 | 11/2014 | Wilton et al. |
| 2014/0350076 A1 | 11/2014 | Van Deutekorn |
| 2014/0357698 A1 | 12/2014 | Van Deutekom et al. |
| 2014/0357855 A1 | 12/2014 | Van Deutekom et al. |

(56) References Cited

U.S. PATENT DOCUMENTS

| | | |
|---|---|---|
| 2015/0045413 A1 | 2/2015 | De Visser et al. |
| 2015/0057330 A1 | 2/2015 | Wilton et al. |
| 2015/0152415 A1 | 6/2015 | Sazani et al. |
| 2015/0232839 A1 | 8/2015 | Iversen et al. |
| 2015/0353931 A1 | 12/2015 | Wilton et al. |
| 2015/0361428 A1 | 12/2015 | Bestwick et al. |
| 2015/0376615 A1 | 12/2015 | Wilton et al. |
| 2015/0376616 A1 | 12/2015 | Wilton et al. |
| 2015/0376617 A1 | 12/2015 | Sazani et al. |
| 2015/0376618 A1 | 12/2015 | Sazani et al. |
| 2016/0002631 A1 | 1/2016 | Wilton et al. |
| 2016/0002632 A1 | 1/2016 | Wilton et al. |
| 2016/0002633 A1 | 1/2016 | Sazani et al. |
| 2016/0002634 A1 | 1/2016 | Sazani et al. |
| 2016/0002635 A1 | 1/2016 | Wilton et al. |
| 2016/0002637 A1 | 1/2016 | Sazani et al. |
| 2016/0040162 A1 | 2/2016 | Bestwick et al. |
| 2016/0177301 A1 | 6/2016 | Wilton et al. |
| 2016/0298111 A1 | 10/2016 | Bestwick et al. |
| 2017/0009233 A1 | 1/2017 | Wilton et al. |
| 2017/0009234 A1 | 1/2017 | Wilton et al. |
| 2017/0283799 A1 | 10/2017 | Kaye |
| 2017/0292125 A1 | 10/2017 | Sazani et al. |
| 2017/0369875 A1 | 12/2017 | Bestwick et al. |
| 2017/0369876 A1 | 12/2017 | Bestwick et al. |
| 2018/0002689 A1 | 1/2018 | Bestwick et al. |

FOREIGN PATENT DOCUMENTS

| | | |
|---|---|---|
| CA | 2507125 A1 | 6/2004 |
| EP | 1054058 A1 | 11/2000 |
| EP | 1160318 A2 | 12/2001 |
| EP | 1191097 A1 | 3/2002 |
| EP | 1191098 A2 | 3/2002 |
| EP | 1495769 A1 | 1/2005 |
| EP | 1544297 A2 | 6/2005 |
| EP | 1568769 A1 | 8/2005 |
| EP | 1619249 A1 | 1/2006 |
| EP | 1191098 B9 | 6/2006 |
| EP | 1766010 B1 | 3/2007 |
| EP | 1857548 A1 | 11/2007 |
| EP | 1495769 B1 | 2/2008 |
| EP | 1160318 B1 | 5/2008 |
| EP | 1619249 B1 | 9/2008 |
| EP | 1544297 B1 | 9/2009 |
| EP | 2119783 A1 | 11/2009 |
| EP | 2135948 A2 | 12/2009 |
| EP | 2206781 A2 | 7/2010 |
| EP | 2258863 A1 | 12/2010 |
| EP | 2284264 A1 | 2/2011 |
| EP | 2374885 A2 | 10/2011 |
| EP | 2386636 A2 | 11/2011 |
| EP | 2392660 A2 | 12/2011 |
| EP | 2500430 A2 | 9/2012 |
| EP | 2530153 A1 | 12/2012 |
| EP | 2530154 A1 | 12/2012 |
| EP | 2530155 A1 | 12/2012 |
| EP | 2530156 A1 | 12/2012 |
| EP | 2581448 A1 | 4/2013 |
| EP | 2594640 A1 | 5/2013 |
| EP | 2594641 A1 | 5/2013 |
| EP | 2594642 A1 | 5/2013 |
| EP | 2602322 A1 | 6/2013 |
| EP | 2607484 A1 | 6/2013 |
| EP | 2612917 A1 | 7/2013 |
| EP | 2614827 A2 | 7/2013 |
| EP | 2623507 A1 | 8/2013 |
| EP | 2636740 A1 | 9/2013 |
| EP | 2636741 A1 | 9/2013 |
| EP | 2636742 A1 | 9/2013 |
| EP | 2435582 B1 | 10/2013 |
| EP | 1606407 B1 | 12/2013 |
| EP | 2435583 B1 | 7/2014 |
| EP | 2488165 B1 | 7/2014 |
| EP | 2135948 B1 | 9/2014 |
| EP | 2799548 A1 | 11/2014 |
| EP | 2801618 A1 | 11/2014 |
| JP | 2000-325085 A | 11/2000 |
| JP | 2002-010790 A | 1/2002 |
| JP | 2002-529499 A | 9/2002 |
| JP | 2002-325582 A | 11/2002 |
| JP | 2002-340857 A | 11/2002 |
| JP | 2004-509622 A | 4/2004 |
| JP | 2010-268815 A | 12/2010 |
| JP | 2011-101655 A | 5/2011 |
| JP | 4777777 B2 | 9/2011 |
| JP | 2011-200235 A | 10/2011 |
| JP | 4846965 B2 | 12/2011 |
| JP | 5138722 B2 | 2/2013 |
| JP | 5378423 B2 | 12/2013 |
| JP | 2014-054250 A | 3/2014 |
| JP | 2014-111638 A | 6/2014 |
| JP | 2014-138589 A | 7/2014 |
| WO | 93/20227 A1 | 10/1993 |
| WO | 94/02595 A1 | 2/1994 |
| WO | 94/26887 A1 | 11/1994 |
| WO | 96/10391 A1 | 4/1996 |
| WO | 96/10392 A1 | 4/1996 |
| WO | 97/30067 A1 | 8/1997 |
| WO | 97/34638 A1 | 9/1997 |
| WO | 00/15780 A1 | 3/2000 |
| WO | 00/44897 A1 | 8/2000 |
| WO | 00/78341 A1 | 12/2000 |
| WO | 01/49775 A2 | 7/2001 |
| WO | 01/72765 A1 | 10/2001 |
| WO | 01/83503 A2 | 11/2001 |
| WO | 01/83740 A2 | 11/2001 |
| WO | 02/018656 A2 | 3/2002 |
| WO | 02/24906 A1 | 3/2002 |
| WO | 02/29406 A1 | 4/2002 |
| WO | 03/053341 A2 | 7/2003 |
| WO | 04/048570 A1 | 6/2004 |
| WO | 04/083432 A1 | 9/2004 |
| WO | 04/083446 A2 | 9/2004 |
| WO | 2005/115479 A2 | 12/2005 |
| WO | 2006/000057 A1 | 1/2006 |
| WO | 2006/021724 A2 | 3/2006 |
| WO | 2006/112705 A2 | 10/2006 |
| WO | 2007/058894 A2 | 5/2007 |
| WO | 2007/133812 A2 | 11/2007 |
| WO | 2007/135105 A1 | 11/2007 |
| WO | 2008/036127 A2 | 3/2008 |
| WO | 2009/054725 A2 | 4/2009 |
| WO | 2009/101399 A1 | 8/2009 |
| WO | 2009/139630 A2 | 11/2009 |
| WO | 2010/048586 A1 | 4/2010 |
| WO | 2010/050801 A1 | 5/2010 |
| WO | 2010/050802 A1 | 5/2010 |
| WO | 2010/115993 A1 | 10/2010 |
| WO | 2010/123369 A1 | 10/2010 |
| WO | 2010/136415 A1 | 12/2010 |
| WO | 2010/136417 A1 | 12/2010 |
| WO | 2010/150231 A1 | 12/2010 |
| WO | 2011/024077 A2 | 3/2011 |
| WO | 2011/045747 A1 | 4/2011 |
| WO | 2011/057350 A1 | 5/2011 |
| WO | 2011/143008 A1 | 11/2011 |
| WO | 2012/001941 A1 | 1/2012 |
| WO | 2012/029986 A1 | 3/2012 |
| WO | 2012/043730 A1 | 4/2012 |
| WO | 2012/109296 A1 | 8/2012 |
| WO | 2012/150960 A1 | 11/2012 |
| WO | 2013/033407 A2 | 3/2013 |
| WO | 2013/053928 A1 | 4/2013 |
| WO | 2013/100190 A1 | 7/2013 |
| WO | 2013/112053 A1 | 8/2013 |
| WO | 2013/142087 A1 | 9/2013 |
| WO | 2014/007620 A2 | 1/2014 |
| WO | 2014/100714 A1 | 6/2014 |
| WO | 2014/144978 A2 | 9/2014 |
| WO | 2014/153220 A2 | 9/2014 |
| WO | 2014/153240 A2 | 9/2014 |
| WO | 2014/172669 A1 | 10/2014 |
| WO | 2017/059131 A1 | 4/2017 |

(56) References Cited

FOREIGN PATENT DOCUMENTS

OTHER PUBLICATIONS

"Efficacy Study of AVI-4658 to Induce Dystrophin Expression in Selected Duchenne Muscular Dystrophy Patients," Clinical Trial Identifier No. NCT01396239, ClinicalTrials.gov, dated Jul. 15, 2011, p. 1-4.
"Efficacy, Safety, and Tolerability Rollover Study of Eteplirsen in Subjects with Duchenne Muscular Dystrophy," Clinical Trial Identifier No. NCT01540409, ClinicalTrials.gov, published online Feb. 23, 2012, p. 1-4.
"Eteplirsen—Inhibitor of Dystrophin Expression—Treatment of Duchenne Muscular Dystrophy", Drugs of the Future, vol. 38(1):13-17 (2013).
"Open-Label, Multiple-Dose, Efficacy, Safety, and Tolerability Study of Eteplirsen in Subjects With Duchenne Muscular Dystrophy Who Participated in Study 4658-US- 201," ClinicalTrials.gov dated Jul. 31, 2012, 3 pages.
"Open-Label, Multiple-Dose, Efficacy, Safety, and Tolerability Study of Eteplirsen in Subjects With Duchenne Muscular Dystrophy Who Participated in Study 4658-US-201," ClinicalTrials.gov dated Oct. 17, 2013, 3 pages.
"Open-Label, Multiple-Dose, Efficacy, Safety, and Tolerability Study of Eteplirsen in Subjects With Duchenne Muscular Dystrophy Who Participated in Study 4658-US-201," ClinicalTrials.gov dated Feb. 27, 2012, 3 pages.
2nd Expert Declaration of Dr. Erik Sontheimer ("S Decl.") (Exhibit No. 1067 filed in interferences 106008, 106007 on Dec. 23, 2014).
3rd Declaration of Erik J. Sontheimer, Ph.D. ("3rd S. Decl."), pp. 123, Exhibit No. 1186 filed in Interferences 106,007 and 106,008 on Feb. 17, 2015.
A Comparative Study on AONs between 20 and 50 Nucleotides Designed to Induce the Skipping of Exon 53 from the Dystrophin Pre-mRNA, pp. 6, Exhibit No. 1128 filed in Interferences 106,007 and 106,008 on Feb. 17, 2015.
A Comparative Study on AONs Between 20 and 50 Nucleotides Designed to Induce the Skipping of Exon 51 from the Dystrophin Pre-mRNA, pp. 6, Exhibit No. 1127 filed in Interferences 106,007 and 106,008 on Feb. 17, 2015.
Aartsma-Rus A, et al. "Theoretic applicability of antisense-mediated exon skipping for Duchenne muscular dystrophy mutations," Hum Mutat 2009;30:293-99.
Aartsma-Rus et al., "Antisense-induced exon skipping for duplications in Duchenne muscular dystrophy," BMC Medical Genetics 8:43 (2007), (University of Western Australia Exhibit 2135, filed Apr. 3, 2015 in Interferences 106007, 106008, and 106013, pp. 1-9.).
Aartsma-Rus, Annemieke et al., "194th ENMC international workshop. 3rd ENMC workshop on exon skipping: Towards clinical application of antisense-mediated exon skipping for Duchenne muscular dystrophy Dec. 8-10, 2012, Naarden, The Netherlands," Neuromuscular Disorders, vol. 23:934-944 (2013).
Aartsma-Rus, Annemieke et al., "Antisense-Induced Multiexon Skipping for Duchenne Muscular Dystrophy Makes More Sense," Am. J. Hum. Genet., vol. 74:83-92 (2004).
Aartsma-Rus, Annemieke et al., "Functional Analysis of 114 Exon-Internal AONs for Targeted DMD Exon Skipping: Indication for Steric Hindrance of SR Protein Binding Sites," Oligonucleotides, vol. 15:284-297 (2005) (Exhibit No. 2016 filed in interferences 106008, 106013, 106007 on Nov. 18, 2014).
Aartsma-Rus, Annemieke et al., "Guidelines for Antisense Oligonucleotide Design and Insight Into Splice-modulating Mechanisms," Molecular Therapy, vol. 17(3):548-553 (2009) (Exhibit No. 2014 filed in interferences 106008, 106013, 106007 on Nov. 18, 2014).
Aartsma-Rus, Annemieke et al., "Guidelines for Antisense Oligonucleotide Design and Insight Into Splice-modulating Mechanisms," Molecular Therapy, vol. 17(3):548-553 (2009). Supplementary Table 1.
Aartsma-Rus, Annemieke et al., "Targeted exon skipping as a potential gene correction therapy for Duchenne muscular dystrophy," Neuromuscular Disorders, vol. 12:S71-S77 (2002).
Aartsma-Rus, Annemieke et al., "Therapeutic antisense-induced exon skipping in cultured muscle cells from six different DMD patients," Human Molecular Genetics, vol. 12(8):907-914 (2003).
Abbs, Stephen et al., "A convenient multiplex PCR system for the detection of dystrophin gene deletions: a comparative analysis with cDNA hybridisation shows mistypings by both methods," J. Med. Genet., vol. 28:304-311 (1991).
Abes, S. et al., "Efficient Splicing Correction by PNA Conjugation to an R6-Penetratin Delivery Peptide", Nucleic Acids Research vol. 35(13):4495-4502 (2007).
Agrawal, Sudhir et al., "GEM 91—An Antisense Oligonucleotide Phosphorothioate as a Therapeutic Agent for AIDS," Antisense Research and Development, vol. 2:261-266 (1992).
Agrawal, Sudhir et al., "Oligodeoxynucleoside phosphoramidates and phosphorothioates as inhibitors of human immunodeficiency virus," Proc. Natl. Acad. Sci. USA, vol. 85:7079-7083 (1988).
Ahmad A, et al., "Mdx mice inducibly expressing dystrophin provide insights into the potential of gene therapy for Duchenne muscular dystrophy," Hum Mol Genet 2000;9:2507-2515.
Akhtar, Saghir et al., "Cellular uptake and intracellular fate of antisense oligonucleotides," Trends in Cell Biology, vol. 2:139-144 (1992).
Akhtar, Saghir, "Delivery Strategies for Antisense Oligonucleotide Therapeutics," CRC Press, Inc., Boca Raton, FL, 160 pages (1995).
Alignments of Dystrophin mRNA and Oligonucleotides, 6 pages, submitted to the Patent Trial and Appeal Board in Interference No. 106008, dated Nov. 18, 2014 (Exhibit No. 1054 filed in interferences 106008, 106007 on Nov. 18, 2014).
Alter, Julia et al., "Systemic delivery of morpholino oligonucleotide restores dystrophin expression bodywide and improves dystrophic pathology," Nature Medicine, vol. 12(2):175-177 (2006).
Amendment under 37 CFR 1.312 for U.S. Appl. No. 14/248,279, 5 pages, dated Sep. 19, 2014 (Exhibit No. 2053 filed in interferences 106008, 106013, 106007 on Nov. 18, 2014).
Analysis of Second PCR Product by Gel Electrophoresis, pp. 1, Exhibit No. 1182 filed in Interferences 106,007 and 106,008 on Feb. 16, 2015.
Anderson, W. French, "Human Gene Therapy," Science, vol. 256:808-813 (1992).
Annotated scenario introduced and referred to during Mar. 12, 2015 deposition of Erik J. Sontheimer, Ph.D., (University of Western Australia Exhibit 2139, filed Apr. 3, 2015 in Interferences 106007, 106008, and 106013, p. 1.).
Anthony, Karen et al., "Dystrophin quantification: Biological and Translational Research Implications," Neurology, vol. 83:1-8 (2014) (Exhibit No. 2028 filed in interferences 106008, 106013, 106007 on Nov. 18, 2014).
AON PS1958 Mass Spectrometry Data, pp. 7, Exhibit No. 1146 filed in Interferences 106,007 and 106,008 on Feb. 16, 2015.
AON PS1958 UPLC Data, pp. 2, Exhibit No. 1157 filed in Interferences 106,007 and 106,008 on Feb. 16, 2015.
AON PS1959 Mass Spectrometry Data, pp. 5, Exhibit No. 1147 filed in Interferences 106,007 and 106,008 on Feb. 16, 2015.
AON PS1959 UPLC Data, pp. 2, Exhibit No. 1158 filed in Interferences 106,007 and 106,008 on Feb. 16, 2015.
AON PS1960 Mass Spectrometry Data, pp. 8, Exhibit No. 1148 filed in Interferences 106,007 and 106,008 on Feb. 16, 2015.
AON PS1960 UPLC Data, pp. 2, Exhibit No. 1159 filed in Interferences 106,007 and 106,008 on Feb. 16, 2015.
AON PS1961 Mass Spectrometry Data, pp. 5, Exhibit No. 1149 filed in Interferences 106,007 and 106,008 on Feb. 16, 2015.
AON PS1961 UPLC Data, pp. 2, Exhibit No. 1160 filed in Interferences 106,007 and 106,008 on Feb. 16, 2015.
AON PS1962 Mass Spectrometry Data, pp. 7, Exhibit No. 1150 filed in Interferences 106,007 and 106,008 on Feb. 16, 2015.
AON PS1962 UPLC Data, pp. 2, Exhibit No. 1161 filed in Interferences 106,007 and 106,008 on Feb. 16, 2015.
AON PS1963 Mass Spectrometry Data, pp. 10, Exhibit No. 1151 filed in Interferences 106,007 and 106,008 on Feb. 16, 2015.

(56) References Cited

OTHER PUBLICATIONS

AON PS1963 UPLC Data, pp. 2, Exhibit No. 1162 filed in Interferences 106,007 and 106,008 on Feb. 16, 2015.
AON PS1964 Mass Spectrometry Data, pp. 13, Exhibit No. 1152 filed in Interferences 106,007 and 106,008 on Feb. 16, 2015.
AON PS1964 UPLC Data, pp. 2, Exhibit No. 1163 filed in Interferences 106,007 and 106,008 on Feb. 16, 2015.
AON PS1965 Mass Spectrometry Data, pp. 9, Exhibit No. 1153 filed in Interferences 106,007 and 106,008 on Feb. 16, 2015.
AON PS1965 UPLC Data, pp. 2, Exhibit No. 1164 filed in Interferences 106,007 and 106,008 on Feb. 16, 2015.
Hammond, Suzan M., et al., "Genetic therapies for RNA missplicing diseases," Cell, vol. 27, No. 5, pp. 196-205 (May 2011), Exhibit No. 1113 filed in interferences 106,007 and 106,008 on Feb. 17, 2015.
Hammond,Suzan M., et al., "PRO-051, an antisense oligonucleotide for the potential treatment of Duchenne muscular dystrophy," Curr. Opinion Mol. Therap., vol. 12, No. 4, pp. 478-486 (2010), Exhibit No. 1121 filed in interferences 106,007 and 106,008 on Feb. 13, 2015.
Harding, PL et al., "The Influence of Antisense Oligonucleotide Length on Dystrophin Exon Skipping," Molecular Therapy, vol. 15(1):157-166 (2007) (Exhibit No. 1030 filed in interferences 106008, 106007 on Nov. 18, 2014).
Havenga et al., "Exploiting the Natural Diversity in Adenovirus Tropism for Therapy and Prevention of Disease," J. Virol., vol. 76, No. 9, pp. 4612-4620 (May 2002), Exhibit No. 1123 filed in interferences 106,007 and 106,008 on Feb. 13, 2015.
Heasman, Janet, "Morpholino Oligos: Making Sense of Antisense?" Developmental Biology, vol. 243:209-214 (2002).
Heemskerk, Hans A. et al., "In vivo comparison of 2'-O-methyl phosphorothioate and morpholino antisense oligonucleotides for Duchenne muscular dystrophy exon skipping," The Journal of Gene Medicine, vol. 11:257-266 (2009) (Exhibit No. 2020 filed in interferences 106008, 106013, 106007 on Nov. 18, 2014).
Heid, Christian A. et al., "Real Time Quantitative PCR," Genome Research, vol. 6:986-994 (1996) (Exhibit No. 1061 filed in interferences 106008, 106007 on Nov. 18, 2014).
Herschlag, Daniel et al., "Contributions of 2'Hydroxyl Groups of the RNA Substrate to Binding and Catalysis by the Tetrahymena Ribozyme: An Energetic Picture of an Active Site Composed of RNA," Biochemistry, vol. 32:8299-8311 (1993) (Exhibit No. 1031 filed in interferences 106008, 106007 on Nov. 18, 2014).
Hoffman EP, et al., "Characterization of dystrophin in musclebiopsy specimens from patients with Duchenne's or Becker's muscular dystrophy" N Engl J Med 1988;318:1363-68.
Hoffman EP, et al., "Restoring dystrophin expression in Duchenne muscular dystrophy muscle: Progress in exon skipping and stop codon read through," Am J Path 2011;179:12-22.
Hudziak, Robert M. et al., "Antiproliferative Effects of Steric Blocking Phosphorodiamidate Morpholino Antisense Agents Directed against c-myc," Antisense & Nucleic Acid Drug Development, vol. 10:163-176 (2000) (Exhibit No. 1032 filed in interferences 106008, 106007 on Nov. 18, 2014).
Hussey, Nicole D. et al., "Analysis of five Duchenne muscular dystrophy exons and gender determination using conventional duplex polymerase chain reaction on single cells," Molecular Human Reproduction, vol. 5(11)1089-1094 (1999).
Interim Guidance on Patent Subject Matter Eligibility ("The December Guidance," 16 pages,(Exhibit No. 2119 filed in interferences 106,007 and 106,008 on Feb. 17, 2015.
International Patent Application No. PCT/AU2000/00693 ("Wraight"), published as WO 00/78341 on Dec. 28, 2000, 201 pages, (Exhibit No. 2125 filed in interferences 106,007 and 106,008 on Feb. 17, 2015.
International Preliminary Report on Patentability and Written Opinion for Application No. PCT/US20091061960, 8 pages, dated Apr. 26, 2011.
International Preliminary Report on Patentability for Application No. PCT/AU2005/000943, 8 pages, dated Dec. 28, 2006.
International Preliminary Report on Patentability, PCT/US2013/077216, dated Jun. 23, 2015, pp. 1-7.
International Preliminary Report on Patentability, PCT/US2014/029610, dated Jul. 1, 2015, pp. 1-122.
International Preliminary Report on Patentability, PCT/US2014/029689, dated Sep. 15, 2015, pp. 1-10.
International Preliminary Report on Patentability, PCT/US2014/029766, dated Sep. 15, 2015, pp. 1-10.
International Search Report and Written Opinion of the International Searching Authority issued in International Patent Application No. PCT/US2013/077216 dated dated Mar. 27, 2014.
International Search Report and Written Opinion of the International Searching Authority issued in International Patent Application No. PCT/US2014/029610 dated Sep. 18, 2014.
International Search Report and Written Opinion of the International Searching Authority issued in International Patent Application No. PCT/US2014/029689, 8 pages, dated Oct. 21, 2014.
International Search Report and Written Opinion of the International Searching Authority issued in International Patent Application No. PCT/US2014/029766 dated Oct. 21, 2014.
International Search Report and Written Opinion, PCT/US2016/054534, dated Jan. 17, 2017, 13 pages.
International Search Report for Application No. PCT/AU2005/000943, 5 pages, dated Oct. 20, 2005.
International Search Report for Application No. PCT/US01/14410, 5 pages, dated Mar. 6, 2002.
International Search Report for Application No. PCT/US2009/061960, 5 pages, dated Apr. 6, 2010.
Invitation to pay fees and Partial International Search Report issued by the International Search Authority in International Patent Application No. PCT/US2014/029689 dated Jul. 29, 2014.
ISIS Pharmaceuticals website, 2 pages, http://www.isispharm.com/Pipeline/Therapeutic-Areas/Other.htm (2014) Exhibit No. 2021 filed in interferences 106008, 106013, 106007 on Nov. 18, 2014).
Iversen, Patrick L. et al., "Efficacy of Antisense Morpholino Oligomer Targeted to c-myc in Prostate Cancer Xenograft Murine Model and a Phase I Safety Study in Humans," Clinical Cancer Research, vol. 9:2510-2519 (2003).
Jarver, Peter et al., "A Chemical View of Oligonucleotides for Exon Skipping and Related Drug Applications," Nucleic Acid Therapeutics, vol. 24(1):37-47 (2014) (Exhibit No. 2061 filed in interferences 106008, 106013, 106007 on Nov. 18, 2014).
Jason, Tracey L.H. et al., "Toxicology of antisense therapeutics," Toxicology and Applied Pharmacology, vol. 201:66-83 (2004) (Exhibit No. 2027 filed in interferences 106008, 106013, 106007 on Nov. 18, 2014).
Jearawiriyapaisarn, Natee et al., "Long-term improvement in mdx cardiomyopathy after therapy with peptide-conjugated morpholino oligomers," Cardiovascular Research, vol. 85:444-453 (2010).
Jearawiriyapaisarn, Natee et al., "Sustained Dystrophin Expression Induced by Peptide-conjugated Morpholino Oligomers in the Muscles of mdx Mice," Mol. Ther., vol. 16(9):1624-1629 (2008).
Jett Foundation Presentation by McSherry, C. "Patient and Caregiver-Reported Outcomes of Patients in Clinical Trials of Eteplirsen for Treatment of Duchenne" at Peripheral and Central Nervous System Drugs Advisory Committee, Apr. 25, 2016, 17 pages.
Job Posting by Sarepta for "Scientist II, Muscle Biology" (2 pages), (Academisch Ziekenhuis Leiden Exhibit 1233, filed Apr. 3, 2015 in Interference 106007 and 106008).
Jones, Simon S. et al., "The Protection of Uracil and Guanine Residues in Oligonucleotide Synthesis," Tetrahedron Letters, vol. 22(47):4755-4758 (1981).
Karlen, Yann et al., "Statistical significance of quantitative PCR," BMC Bioinformatics, 8:131, 16 pages (2007) (Exhibit No. 1033 filed in interferences 106008, 106007 on Nov. 18, 2014).
Karras, James G. et al., "Deletion of Individual Exons and Induction of Soluble Murine Interleukin-5 Receptor-alpha Chain Expression through Antisense Oligonucleotide-Mediated Redirection of PremRNA splicing," Molecular Pharmacology, vol. 58:380-387 (2000).
Kaye, Ed, "Results of the Eteplirsen Phase 2b and Phase 2b Extension Study in Duchenne Muscular Dystrophy," 8th Annual

(56) References Cited

OTHER PUBLICATIONS

Meeting of the Oligonucleotide Therapeutics Society, Session 9: Advances in Oligonucleotide Clinical Development II, p. 48 (2012).
Kinali, Maria et al., "Local restoration of dystrophin expression with the morpholino oligomer AVI-4658 in Duchenne muscular dystrophy: a single-blind, placebo-controlled, dose-escalation, proof-of-concept study," Lancet Neurol., vol. 8:918-928 (2009).
King et al., "A Dictionary of Genetics," Oxford University Press, 4th Ed. (1990), Exhibit No. 1189 filed in Interferences 106,007 and 106,008 on Feb. 17, 2015.
Koenig, M. et al., "The Complete Sequence of Dystrophin Predicts a Rod-Shaped Cytoskeleton Protein," Cell, vol. 53:219-228 (1988) (Exhibit No. 1010 filed in interferences 106008, 106007 on Nov. 18, 2014).
Koenig, M. et al., "The Molecular Basis for Duchenne versus Becker Muscular Dystrophy: Correlation of Severity with Type of Deletion," Am. J. Hum. Genet., vol. 45:498-506 (1989) (Exhibit No. 1011 filed in interferences 106008, 106007 on Nov. 18, 2014).
Kohler M, et al., "Quality of life, physical disability and respiratory impairment in Duchenne muscular dystrophy," Am J Respir Crit Care Med 2005;172:1032-6.
Kole et al. "Exon skipping therapy for Duchenne muscular dystrophy," Advanced Drug Delivery Reviews, vol. 87:104-107 (2015).
Koshkin, Alexei A. et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecendented Nucleic Acid Recognition," Tetrahedron, vol. 54:3607-3630 (1998) (Exhibit No. 2007 filed in interferences 106008, 106013, 106007 on Nov. 18, 2014).
Kurreck J., "Antisense Technologies: Improvement Through Novel Chemical Modifications", European Journal of Biochemistry, vol. 270(8):1628-1644 (2003).
Lab-on-a-Chip Data, pp. 28, Exhibit No. 1185 filed in Interferences 106,007 and 106,008 on Feb. 16, 2015.
Sarepta Briefing Information for the Apr. 25, 2016 Meeting of the Peripheral and Central Nervous System Drugs Advisory Committee, Eteplirsen Briefing Document, NDA 206488, 186 pages.
Sarepta Presentation at Peripheral and Central Nervous System Drugs Advisory Committee, Apr. 25, 2016, 133 pages.
Sarepta Press Release, Sarepta Issues Statement on Advisory Committee Outcome for Use of Eteplirsen in the Treatment of Duchenne Muscular Dystrophy, Apr. 25, 2016, 2 pages.
Sarepta Therapeutics Press Release, dated Jan. 12, 2015, Exhibit No. 1119 filed in interferences 106,007 and 106,008 on Feb. 17, 2015.
Sarepta Therapeutics, Advisory Committee Briefing Materials: Available for Public Release, "Peripheral and Central Nervous System Drugs Advisory Committee," Eteplirsen Briefing Document Addendum, NDA 206488, pp. 1-9, dated Jan. 22, 2016.
Sarepta Therapeutics, Advisory Committee Briefing Materials: Available for Public Release, "Peripheral and Central Nervous System Drugs Advisory Committee," Eteplirsen Briefing Document, NDA 206488, pp. 1-166, dated Jan. 22, 2016.
Sarepta Therapeutics, Inc. News Release, "Sarepta Therapeutics Announces FDA Accelerated Approval of EXONDYS61™ (eteplirsen) injection, an Exon Skipping Therapy to Treat Duchenne Muscular Dystrophy (DMD) Patients Amenable to Skipping Exon 51," Sep. 19, 2016, 2 pages.
Sarepta, "AVI BioPharma Initiates Dosing in Phase 2 Study of Eteplirsen in Duchenne Muscular Dystrophy Patients," press release, 4 pages, dated Aug. 15, 2011 (Exhibit No. 2082 filed in interferences 106008, 106013, 106007 on Nov. 18, 2014).
Sarepta, "Sarepta Therapeutics Announces Eteplirsen Demonstrates Continued Stability on Walking Test through 120 Weeks in Phase IIb Study in Duchenne Muscular Dystrophy," press release, 3 pages, dated Jan. 15, 2014 (Exhibit No. 2034 filed in interferences 106008, 106013, 106007 on Nov. 18, 2014).
Sarepta, "Sarepta Therapeutics Reports Long-Term Outcomes through 144 Weeks from Phase IIb Study of Eteplirsen in Duchenne Muscular Dystrophy," press release, http://investorrelations.sarepta.com/phoenix.zhtml?c=64231&p=irol-newsArticle&id=1946426, 4 pages, dated Jul. 10, 2014.
Scully, Michele et al., "Review of Phase II and Phase III Clinical Trials for Duchenne Muscular Dystrophy", Expert Opinion on Orphan Drugs, vol. 1(1):33-46 (2013).
Second Preliminary Amendment filed in U.S. Appl. No. 13/550,210, 5 pages, dated Jan. 3, 2013 (Exhibit No. 2062 filed in interferences 106008, 106013, 106007 on Nov. 18, 2014).
Second Written Opinion for Application No. PCT/AU2010/001520, 7 pages, dated Oct. 13, 2011.
Semi Quantitative Lab-on-Chip Analysis of Second PCR Product, pp. 1, Exhibit No. 1183 filed in Interferences 106,007 and 106,008 on Feb. 16, 2015.
Sequence Listing—U.S. Appl. No. 13/550,210, filed Jul. 16, 2012 (9 pages), Exhibit No. 1205 filed in Interferences 106,007 and 106,008 on Feb. 17, 2015.
Sequence of Exon 46 of Dystrophin Gene, 1 page.
Sequence of Exon 51 of Dystrophin Gene, 1 page.
Shabanpoor et al., "Bi-specific splice-switching PMO oligonucleotides conjugated via a single peptide active in a mouse model of Duchenne muscular dystrophy," Nucleic Acids Res., pp. 1-11 (Dec. 2014), Exhibit No. 1114 filed in interferences 106,007 and 106,008 on Feb. 17, 2015.
Shapiro, Marvin B. et al., "RNA splice junctions of different classes of eukaryotes: sequence statistics and functional implications in gene expression," Nucleic Acids Research, vol. 15(17):7155-7174 (1987).
Sherratt, Tim G. et al., "Exon Skipping and Translation in Patients with Frameshift Deletions in the Dystrophin Gene," Am. J. Hum. Genet., vol. 53:1007-1015 (1993).
Shiga, Nobuyuki et al., "Disruption of the Splicing Enhancer Sequence within Exon 27 of the Dystrophin Gene by a Nonsense Mutation Induced Partial Skipping of the Exon and Is Responsible for Becker Muscular Dystrophy," J. Clin. Invest., vol. 100(9):2204-2210 (1997).
Shimizu, Miho et al., "Oligo(2'-O-methyl)ribonucleotides Effective probes for duplex DNA," FEBS Letters, vol. 302 (2)155-158 (1992) (Exhibit No. 1035 filed in interferences 106008, 106007 on Nov. 18, 2014).
*Siemens Healthcare Diagnostics, Inc.* v. *Enzo Life Sciences, Inc.*, 2013 WL 4411227, *11 [Parallel cite: U.S.D.C., D. Mass., Civil No. 10-40124-FDS], Decided Aug. 14, 2013 (12 pages); [Cited as: 2013 WL 4411227], Exhibit No. 1210 filed in Interferences 106,007 and 106,008 on Feb. 17, 2015.
Sierakowska, Halina et al., "Repair of thalassemic human beta-globin mRNA in mammalian cells by antisense oligonucleotides," Proc. Natl. Acad. Sci. USA, vol. 93:12840-12844 (1996).
Sontheimer et al., "Metal ion catalysis during group II intron self-splicing: parallels with the spliceosome," Genes & Development, vol. 13, pp. 1729-1741 (1999), Exhibit No. 1195 filed in Interferences 106,007 and 106,008 on Feb. 17, 2015.
Sontheimer et al., "Three Novel Functional Variants of Human U5 Small Nuclear RNA," vol. 12, No. 2, pp. 734-746 (Feb. 1992), Exhibit No. 1194 filed in Interferences 106,007 and 106,008 on Feb. 17, 2015.
Sontheimer, Erik J. et al., "Metal ion catalysis during splicing of premessenger RNA," Nature, vol. 388:801-805 :(1997) (Exhibit No. 1036 filed in interferences 106008, 106007 on Nov. 18, 2014).
Sontheimer, Erik J. et al., "The U5 and U6 Small Nuclear RNAs as Active Site Components of the Spliceosome," Science, vol. 262:1989-1997 (1993) (Exhibit No. 1058 filed in interferences 106008, 106007 on Nov. 18, 2014).
Standard Operating Procedure FPLC Desalting, pp. 6, Exhibit No. 1144 filed in Interferences 106,007 and 106,008 on Feb. 16, 2015.
Stanton, Robert et al., "Chemical Modification Study of Antisense Gapmers", Nucleic Acid Therapeutics, vol. 22(5): 344-359 (2012).
Statement on a Nonproprietary Name Adopted by the USAN Council, Eteplirsen, Chemical Structure, 2010, pp. 1-5.
Stein, CA, "Delivery of antisense oligonucleotides to cells: a consideration of some of the barriers," Monographic supplement series: Oligos & Peptides—Chimica Oggi—Chemistry Today, vol. 32(2):4-7 (2014) (Exhibit No. 2022 filed in interferences 106008, 106013, 106007 on Nov. 18, 2014).

(56) References Cited

OTHER PUBLICATIONS

Stein, Cy A. et al., "Therapeutic Oligonucleotides: The Road Not Taken," Clin. Cancer Res., vol. 17(20):6369-6372 (2011) (Exhibit No. 2026 filed in interferences 106008, 106013, 106007 on Nov. 18, 2014).

Stein, David et al., "A Specificity Comparison of Four Antisense Types: Morpholino, 2'-O-Methyl RNA, DNA, and PHosphorothioate DNA," Antisense & Nucleic Acid Drug Development, vol. 7:151-157 (1997).

Strober JB, "Therapeutics in Duchenne muscular dystrophy," NeuroRX 2006; 3:225-34.

Summary of Professional Experience (Dr. Erik J. Sontheimer), pp. 4, Exhibit No. 1223 filed in Interferences 106,007 and 106,008 on Feb. 17, 2015.

Summerton, James et al., "Morpholino and Phosphorothioate Antisense Oligomers Compared in Cell-Free and In-Cell Systems," Antisense & Nucleic Acid Drug Development, vol. 7:63-70 (1997).

Summerton, James et al., "Morpholino Antisense Oligomers: Design, Preparation, and Properties," Antisense & Nucleic Acid Drug Development, vol. 7:187-195 (1997).

Summerton, James, "Morpholino antisense oligomers: the case for an Rnase H-independent structural type," Biochimica et Biophysica Acta, vol. 1489:141-158 (1999) (Exhibit No. 1038 filed in interferences 106008, 106013, 106007 on Nov. 18, 2014).

Supplementary European Search Report for Application No. 10829367.1, 8 pages, dated May 22, 2013.

Suter et al., "Double-target antisense U7 snRNAs promote efficient skipping of an aberrant exon in three human Beta-thalassemic mutations," 8:13 Human Molecular Genetics 2415-2423 (1999) (Exhibit No. 1083 filed in Interferences 106008, 106007 on Dec. 23, 2014).

T Hoen, Peter A.C. et al., "Generation and Characterization of Transgenic Mice with the Full-length Human DMD Gene," The Journal of Biological Chemistry, vol. 283(9):5899-5907 (2008) Exhibit No. 2030 filed in interferences 106008, 106013, 106007 on Nov. 18, 2014).

Table 1: Primer and Product Details for Exon 51 and 53 Reports on AONs of 20 to 50 Nucleotides dd Jan. 7, 2015, pp. 1, Exhibit No. 1177 filed in Interferences 106,007 and 106,008 on Feb. 16, 2015.

Takeshima et al., "Oligonucleotides against a splicing enhancer sequence led to dystrophin production in muscle cells from a Duchenne muscular dystrophy patient," Brain & Dev., vol. 23, pp. 788-790 (2001), Exhibit No. 1196 filed in Interferences 106,007 and 106,008 on Feb. 17, 2015.

Takeshima, Yasuhiro et al., "Modulation of in Vitro Splicing of the Upstream Intron by Modifying an Intra-Exon Sequence Which Is Deleted from the Dystrophin Gene in Dystrophin Kobe," J. Clin. Invest, vol. 95:515-520 (1995).

Tanaka, Kenji et al., "Polypurine Sequences within a Downstream Exon Function as a Splicing Enhancer," Molecular and Cellular Biology, vol. 14(2):1347-1354 (1994).

*Telios Pharms., Inc. v. Merck KgaA*, No. 96-1307, 1998 WL 35272018 (S.D. Cal. Nov. 18, 1998), 11 pages (Exhibit No. 2153 filed in interference 106013 on Oct. 29, 2015).

Thanh, Le Htiet et al., "Characterization of Revertant Muscle Fibers in Duchenne Muscular Dystrophy, Using Exon-Specific Monoclonal Antibodies against Dystrophin," Am. J. Hum. Genet., vol. 56:725-731 (1995).

*The Regents of the University of California v. Dako North America, Inc.*, U.S.D.C., N.D. California, No. C05-03955 MHP, Apr. 22, 2009 (2009 WL 1083446 (N.D.Cal.), Exhibit No. 1206 filed in Interferences 106,007 and 106,008 on Feb. 17, 2015.

Tian, Xiaobing et al., "Imaging Oncogene Expression," Ann. N.Y. Acad. Sci., vol. 1002:165-188 (2003) (Exhibit No. 2029 filed in interferences 106008, 106013, 106007 on Nov. 18, 2014).

Excerpts of SEC Form 8-K, dated Nov. 23, 2014, for BioMarin Pharmaceutical Inc., (University of Western Australia Exhibit 2129, filed Apr. 3, 2015 in Interferences 106007, 106008, and 106013, pp. 1-9).

Exon 46 Sequence of Dystrophin, Document D18 as filed in Opposition of European Patent EP1619249, filed Jun. 23, 2009, 1 page.

Exon 51 Internal Sequence Schematic, pp. 1, Exhibit No. 1224 filed in Interferences 106,007 and 106,008 on Feb. 17, 2015.

Exon 53 Internal Sequence Schematic, pp. 1, Exhibit No. 1225 filed in Interferences 106,007 and 106,008 on Feb. 17, 2015.

Extended European Search Report, EP 15190341.6, dated Apr. 28, 2016, 9 pages.

Fairclough et al., "Therapy for Duchenne muscular dystrophy: renewed optimism from genetic approaches," Nature Reviews, vol. 14, pp. 373-378 (Jun. 2013), Exhibit No. 1112 filed in interferences 106,007 and 106,008 on Feb. 17, 2015.

Fall, Abbie M. et al., "Induction of revertant fibres in the mdx mouse using antisense oligonucleotides," Genetics Vaccines and Therapy, vol. 4:3, doi:10.1186/1479-0556-4-3, 12 pages (2006).

FDA Briefing Document, "Peripheral and Central Nervous System," Drugs Advisory Committee Meeting, NDA 206488 Eteplirsen, Food and Drug Administration, pp. 1-73, Jan. 22, 2016.

FDA Briefing Information for the Apr. 25, 2016 Meeting of the Peripheral and Central Nervous System Drugs Advisory Committee, Eteplirsen, NDA 206488, 115 pages.

FDA News Release, "FDA grants accelerated approval to first drug for Duchenne muscular dystrophy," Sep. 19, 2016, 3 pages.

Federal Register, vol. 58, No. 183, pp. 49432-49434, Sep. 23, 1993 (6 pages); [Cited as: 58 FR 49432-01, 1993 WL 371451 (F.R.)], Exhibit No. 1221 filed in Interferences 106,007 and 106,008 on Feb. 17, 2015.

Federal Register, vol. 69, No. 155, pp. 49960-50020 dated Aug. 12, 2004 (62 pages), Exhibit No. 1220 filed in Interferences 106,007 and 106,008 on Feb. 17, 2015.

Feener, C. et al., "Alternative splicing of human dystrophin mRNA generates isoforms at the carboxy terminus," Nature, vol. 338:509-511 (1989).

File Excerpt from AZL U.S. Appl. No. 11/233,495: Amendment After Non-Final Office Action, as-filed Nov. 1, 2010 (Exhibit No. 1085 filed in interferences 106008, 106007 on Dec. 23, 2014).

File Excerpt from AZL U.S. Appl. No. 11/233,495: Claims examined in Non-Final Office Action, dated Dec. 1, 2008 (Exhibit No. 1079 filed in interferences 106008, 106007 on Dec. 23, 2014).

File Excerpt from AZL U.S. Appl. No. 11/233,495: Final Office Action dated Aug. 31, 2010 (Exhibit No. 1086 filed in interferences 106008, 106007 on Dec. 23, 2014).

File Excerpt from U.S. Appl. No. 11/233,495: Non-Final Office Action dated Dec. 1, 2008 and Final Office Action dated Jun. 25, 2009 (Exhibit No. 1078 filed in interferences 106008, 106007 on Dec. 23, 2014).

File Excerpt from U.S. Appl. No. 12/198,007: AZL's Preliminary Amendment and Response, as-filed Nov. 7, 2008 (Exhibit No. 1075 filed in interferences 106008, 106007 on Dec. 23, 2014).

File Excerpt from U.S. Appl. No. 12/976,381: AZL's First Preliminary Amendment, as-filed Dec. 22, 2010 (Exhibit No. 1076 filed in interferences 106008, 106007 on Dec. 23, 2014).

File Excerpts from Prosecution History of U.S. Appl. No. 13/270,992 (UWA's U.S. Pat. No. 8,486,907), pp. 122, Exhibit No. 1006 filed in Interference 106,013 on Feb. 17, 2015.

File Excerpts from U.S. Appl. No. 11/233,495: Response to Non-Final Office Action, as filed Jul. 26, 2011 (14 pages), Exhibit No. 1222 filed in Interferences 106,007 and 106,008 on Feb. 17, 2015.

File Excerpts from U.S. Appl. No. 13/270,992 (UWA's U.S. Pat. No. 8,486,907): NFOA, dated Jul. 30, 2012; Applicant-Initiated Interview Summary, dated Nov. 8, 2012; Amendment, as filed Jan. 30, 2013; NOA, dated Apr. 4, 2013, Exhibit No. 1118 (122 pages) filed in interferences 106,007 and 106,008 on Feb. 17, 2015.

Flanagan, W. Michael, et al., "A cytosine analog that confers enhanced potency to antisense oligonucleotides," Proc. Nat'l Acad. Sci. USA, vol. 96, pp. 3513-3518 (Mar. 1999), Exhibit No. 1211 filed in Interferences 106,007 and 106,008 on Feb. 17, 2015.

Flanigan et al. (2003) "Rapid Direct Sequence Analysis of the Dystrophin Gene," Am. J. Hum. Genet. 72:931-939, dated Feb. 17, 2015 (Exhibit No. 2120 filed in interferences 106,007 and 106,008 on Feb. 17, 2015.

(56) References Cited

OTHER PUBLICATIONS

Flanigan, Kevin M. et al., "Pharmacokinetics and safety of single doses of drisapersen in non-ambulant subjects with Duchenne muscular dystrophy: Results of a double-blind randomized clinical trial," Neuromuscular Disorders, vol. 24:16-24 (2014) (Exhibit No. 2038 filed in interferences 106008, 106013, 106007 on Nov. 18, 2014).
Fletcher S., et al, Morpholino oligomer-mediated exon skipping averts the onset of dystrophic pathology in the mdx mouse. Mol Ther 2007;15:1587-1592.
Fletcher, Sue et al., "Dystrophin Isoform Induction In Vivo by Antisense-mediated Alternative Splicing," Molecular Therapy, vol. 18(6):1218-1223 (2010).
Fletcher, Sue et al., "Targeted Exon Skipping to Address 'Leaky' Mutations in the Dystrophin Gene," Molecular Therapy—Nucleic Acids, vol. 1, e48, doi:10.1038/mtna.2012.40, 11 pages (2012).
Fletcher, Susan et al., "Dystrophin expression in the mdx mouse after localised and systemic administration of a morpholino antisense oligonucleotide," J. Gene Med., vol. 8:207-216 (2006).
Fletcher, Susan et al., "Gene therapy and molecular approaches to the treatment of hereditary muscular disorders," Curr. Opin. Neurol., vol. 13:553-560 (2000).
Foster, Helen et al., "Genetic Therapeutic Approaches for Duchenne Muscular Dystrophy," Human Gene Therapy, vol. 23:676-687 (2012).
Fourth Declaration of Erik Sontheimer, Ph.D. (Pursuant to Bd.R. 41.155(b)(2) and SO 155.1.3 and 155.1.4), dated Mar. 9, 2015, (University of Western Australia Exhibit 2138, filed Apr. 3, 2015 in Interferences 106007, 106008, and 106013, pp. 1-4).
Fragall, Clayton T. et al., "Mismatched single stranded antisense oligonucleotides can induce efficient dystrophin splice switching," BMC Medical Genetics, vol. 12:141, 8 pages (2011) (Exhibit No. 2019 filed in interferences 106008, 106013, 106007 on Nov. 18, 2014).
Fraley, Robert et al., "New generation of liposomes: the engineering of an efficient vehicle for intracellular delivery of nucleic acids," Trends Biochem., vol. 6:77-80 (1981).
Frazier, Kendall S. et al., "Species-specific Inflammatory Responses as a Primary Component for the Development of Glomerular Lesions in Mice and Monkeys Following Chronic Administration of a Second-generation Antisense Oligonucleotide," Toxicologica Pathology, 13 pages (2013).
Friedmann, Theodore, "Progress Toward Human Gene Therapy," Science, vol. 244(4910):1275-1281 (1989).
Gebski, Bianca L. et al., "Morpholino antisense oligonucleotide induced dystrophin exon 23 skipping in mdx mouse muscle," Human Molecular Genetics, vol. 12(15):1801-1811 (2003).
GenBank AF213437.1 Dated Jan. 17, 2002.
Generic Method for Average Mass Determination Using LC-UV-MS in the Negative Mode, pp. 15, Exhibit No. 1145 filed in Interferences 106,007 and 106,008 on Feb. 16, 2015.
Generic UPLC Purity Method for Oligonucleotides (19-to 25-mers), pp. 18, Exhibit No. 1156 filed in Interferences 106,007 and 106,008 on Feb. 16, 2015.
Gennaro, Alfonso R., (ed.), Remington's Pharmaceutical Sciences, 18th Edition, Mack Publishing, Co., Easton PA, 2020 pages (1990).
Giles, Richard V. et al., "Antisense Morpholino Oligonucleotide Analog Induces Missplicing of C-myc mRNA," Antisense & Nucleic Acid Drug Development, vol. 9:213-220 (1999).
GlaxoSmithKline Press Release, Issued in London, UK, dated Jun. 27, 2013 (5 pages), Exhibit No. 1202 filed in Interferences 106,007 and 106,008 on Feb. 17, 2015.
GlaxoSmithKline, "GSK and Prosensa announce start of Phase III study of investigational Duchenne Muscular Dystrophy medication," press release, 6 pages, dated Jan. 19, 2011 (Exhibit No. 2060 filed in interferences 106008, 106013, 106007 on Nov. 18, 2014).
GlaxoSmithKline, Prosensa regains rights to drisapersen from GSK and retains rights to all other programmes for the reatment of Duchenne muscular dystrophy (DMD), press release, 4 pages, dated Jan. 13, 2014 (Exhibit 2040 in Interferences 106007, 106008, and 106013 on Nov. 18, 2014).
Goemans, Nathalie M. et al., "Systemic Administration of PRO051 in Duchenne's Muscular Dystrophy," The New England Journal of Medicine, vol. 364:1513-1522 (2011) (Exhibit No. 2036 filed in interferences 106008, 106013, 106007 on Nov. 18, 2014).
Gordon et al., "Kinetic Characterization of the Second Step of Group II Intron Splicing: Role of Metal Ions and the Cleavage Site 2'-OH in Catalysis," Biochemistry, vol. 39, pp. 12939-12952 (2000), Exhibit No. 1188 filed in Interferences 106,007 and 106,008 on Feb. 17, 2015.
Gordon, Peter M. et al., "Metal ion catalysis during the exon-ligation step of nuclear pre-mRNA splicing: Extending the parallels between the spliceosome and group II introns," RNA, vol. 6:199-205 (2000) (Exhibit No. 1055 filed in interferences 106008, 106007 on Nov. 18, 2014).
Goyenvalle, Aurelie et al., "Prevention of Dystrophic Pathology in Severely Affected Dystrophin/Utrophin-deficient Mice by Morpholino-oligomer-mediated Exon-skipping," Molecular Therapy, vol. 18(1):198-205 (2010).
Hammond, Suzan M. et al., "Correlating In Vitro Splice Switching Activity With Systemic In Vivo Delivery Using Novel ZEN-modified Oligonucleotides," Molecular Therapy—Nucleic Acids, vol. 3:1, 11 pages (2014) (Exhibit No. 2011 filed in interferences 106008, 106013, 106007 on Nov. 18, 2014).
Mitrpant, Chalermchai et al., "Rational Design of Antisense Oligomers to Induce Dystrophin Exon Skipping," Molecular Therapy, vol. 17(8):1418-1426 (2009).
Monaco, Anthony P. et al., "An Explanation for the Phenotypic Differences between Patients Bearing Partial Deletions of the DMD Locus," Genomics, vol. 2:90-95 (1988).
Morcos, Paul A., "Gene switching: analyzing a broad range of mutations using steric block antisense oligonucleotides," Methods in Enzymology, vol. 313:174-189 (1999).
Moulton, H.M., "Compound and Method for Treating Myotonic Dystrophy," U.S. Appl. No. 12/493,140, 82 pages, filed Jun. 26, 2009.
Moulton, Hong M. et al., "Morpholinos and their peptide conjugates: Therapeutic promise and challenge for Duchenne muscular dystrophy," Biochimica et Biophysica Acta, vol. 1798:2296-2303 (2010).
Muntoni F, et al., "Dystrophin and mutations: one gene, several proteins, multiple phenotypes," Lancet Neurol. 2003;2:731-40.
Muntoni, Francesco et al., "128th ENMC International Workshop on 'Preclinical optimization and Phase I/II Clinical Trials Using Antisense Oligonucleotides in Duchenne Muscular Dystrophy' Oct. 22-24, 2004, Naarden, The Netherlands," Neuromuscular Disorders, vol. 15:450-457 (2005) (Exhibit No. 2025 filed in interferences 106008, 106013, 106007 on Nov. 18, 2014).
Muntoni, Francesco et al., "149th ENMC International Workshop and 1st TREAT-NMD Workshop on: 'Planning Phase I/II Clinical trials using Systemically Delivered Antisense Oligonucleotides in Duchenne Muscular Dystrophy,'" Neuromuscular Disorders, vol. 18:268-275 (2008).
Confirmatory Study of Eteplirsen in DMD Patients, An Open-Label, Multi-Center, 48-Week Study With a Concurrent Untreated Control Arm to Evaluate the Efficacy and Safety of Eteplirsen in Duchenne Muscular Dystrophy, Clinical Trials.gov, Clinical Trial Identifier NCT02255552, May 26, 2015, 3 pages.
Nelson, David L. et al., "Nucleotides and Nucleic Acids," Lehninger Principles of Biochemistry, 3rd Edition, Chapter 10, pp. 325-328 and glossary p. G-11, Worth Publishers, New York (2000).
Nguyen TM, et. Al., "Use of Epitope libraries to identify exon-specific monoclonal antibodies for characterization of altered dystrophins in muscular dystrophy," Am J Hum Genet 1993;52:1057-66.
Oberbauer, "Renal uptake of an 18-mer phosphorothioate oligonucleotide," Kidney Int'l, vol. 48, pp. 1226-1232 (1995), Exhibit No. 1191 filed in Interferences 106,007 and 106,008 on Feb. 17, 2015.

(56) References Cited

OTHER PUBLICATIONS

Oligonucleotide Cleavage and Deprotection Laboratory Notebook Entry, pp. 1, Exhibit No. 1138 filed in Interferences 106,007 and 106,008 on Feb. 16, 2015.
Oligonucleotide diagrams, 5 pages (Exhibit No. 1053 filed in interferences 106008, 106007 on Nov. 18, 2014).
Partial European Search Report for Application No. 10004274.6, 6 pages, dated Oct. 2, 2012.
Partial European Search Report for Application No. 12162995.0, 6 pages, dated Oct. 2, 2012.
Patentee's Response to European Patent Application No. 05076770.6, dated Jul. 28, 2006, 4 pages.
*Patrick O. Brown and Tidear D. Shalon* v. *Stephen P.A. Fodor, Dennis W. Solas and William J. Dower*: Interference Merits Panel, Interference No. 104,358, 24 pages, dated Aug. 9, 1999 (Exhibit No. 2113 filed in interferences 106008, 106013, 106007 on Nov. 18, 2014).
PCT Application as-filed for application No. PCT/NL03/00214, 64 pages, dated Sep. 21, 2005 (Exhibit No. 2042 filed in interferences 106008, 106013, 106007 on Nov. 18, 2014).
PD-10 Desalting Columns, pp. 12, Exhibit No. 1141 filed in Interferences 106,007 and 106,008 on Feb. 16, 2015.
Popplewell, et al., Design of Phosphorodiamidate Morpholino Oligomers (PMOs) for the Induction of Exon Skipping of the Human DMD Gene, DSGT Poster, 2008, 1 page.
Popplewell, Linda et al., "Design of phosphorodiamidate morpholino oligmers (PMOs) for the induction of exon skipping of the human DMD gene," Human Gene Therapy 19(10): ESGCT 2008 Poster Presentations, p. 1174, Poster No. P203.
Popplewell, Linda J. et al., "Comparative analysis of antisense oligonucleotide sequences targeting exon 53 of the human DMD gene: Implications for future clinical trials," Neuromuscular Disorders, vol. 20(2):102-110 (2010) 9 pages (Exhibit No. 2031 filed in interferences 106008, 106013, 106007 on Nov. 18, 2014).
Popplewell, Linda J. et al., "Design of Antisense Oligonucleotides for Exon Skipping of the Human Dystrophin Gene," Human Gene Therapy 19(4): BSGT 2008 Poster Presentation, p. 407, Poster No. P-35.
Popplewell, Linda J. et al., "Design of Phosphorodiamidate Morpholino Oligomers (PMOs) for the Induction of Exon Skipping of the Human DMD Gene," Molecular Therapy, vol. 17(3):554-561 (2009).
Popplewell, Linda J. et al., "Targeted Skipping of Exon 53 of the Human DMD Gene Recommendation of the Highly Efficient Antisense Oligonucleotide for Clinical Trial," Human Gene Therapy 20(4): BSGT 2009 Poster Presentations, p. 399, Poster No. P10.
Poster Abstract Listing for the Tenth Annual Meeting of the RNA Society, held at the Banff Centre for Conferences, in Banff, Alberta, Canada, from May 24-29, 2005, (University of Western Australia Exhibit 2137, filed Apr. 3, 2015 in Interferences 106007, 106008, and 106013, pp. 1-11).
Pramono, "Induction of Exon Skipping of the Dystrophin Transcript in Lymphoblastoid Cells by Transfecting an Antisense Oligodeoxynucleotide Complementary to an Exon Recognition Sequence," Biochem. and Biophy. Res. Comm., vol. 226, pp. 445-449 (1996), Exhibit No. 1192 filed in Interferences 106,007 and 106,008 on Feb. 17, 2015.
Preliminary Amendment for U.S. Appl. No. 12/976,381, 4 pages, dated Dec. 22, 2010 (Exhibit No. 2066 filed in interferences 106008, 106013, 106007 on Nov. 18, 2014).
Preliminary Amendment for U.S. Appl. No. 12/198,007, 3 pages, dated Nov. 7, 2008 (Exhibit No. 2067 filed in interferences 106008, 106013, 106007 on Nov. 18, 2014).
Prescribing Information for EXONDYS 51 (eteplirsen) Injection, dated Sep. 2016, 10 pages.
Program Schedule for the Tenth Annual Meeting of the RNA Society, held at the Banff Centre for Conferences, in Banff, Alberta, Canada, from May 24-29, 2005, (University of Western Australia Exhibit 2136, filed Apr. 3, 2015 in Interferences 106007, 106008, and 106013, pp. 1-4).
Proliferation and Differentiation of Myoblast Cultures, pp. 2, Exhibit No. 1169 filed in Interferences 106,007 and 106,008 on Feb. 16, 2015.
Prosensa Press Release, dated Oct. 10, 2014 (2 pages), Exhibit No. 1203 filed in Interferences 106,007 and 106,008 on Feb. 17, 2015.
Prosensa, "GSK and Prosensa Announce Primary Endpoint Not Met in Phase III Study of Drisapersen in Patients With Duchenne Muscular Dystrophy," press release, 4 pages, dated Sep. 20, 2013 (Exhibit No. 2039 filed in interferences 106008, 106013, 106007 on Nov. 18, 2014).
Raz et al. v. Davis et al., Board of Patent Appeals and Inteferences, Patent and Trademark Office, Int. No. 105,712, Tech. Ctr. 1600, Sep. 29, 2011 (24 pages) (2011 WL 4568986 (Bd.Pat.App. & Interf.), Exhibit No. 1209 filed in Interferences 106,007 and 106,008 on Feb. 17, 2015.
Reese, Colin B. et al., "Reaction Between 1-Arenesulphonyl-3-Nitro-1,2,4-Triazoles and Nucleoside Base Residues. Elucidation of the Nature of Side-Reactions During Oligonucleotide Synthesis," Tetrahedron Letters, vol. 21:2265-2268 (1980).
Reese, Colin B. et al., "The Protection of Thymine and Guanine Residues in Oligodeoxyribonucleotide Synthesis," J. Chem. Soc. Perkin Trans. 1, pp. 1263-1271 (1984).
Reexamination Certificate—U.S. Appl. No. 90/011,320, issued Mar. 27, 2012 (Exhibit No. 1072 filed in interferences 106008, 106007 on Dec. 23, 2014).
Reply to EPO Communication dated Jun. 26, 2014 in European Serial No. 13160,338, (University of Western Australia Exhibit 2145, filed Apr. 3, 2015 in Interferences 106007, 106008, and 106013, pp. 1-4).
Reply to EPO Communication dated Oct. 21, 2014 in European Application Serial No. 12198517, (University of Western Australia Exhibit 2148, filed Apr. 3, 2015 in Interferences 106007, 106008, and 106013, pp. 1-7).
Reply to EPO Communication dated Oct. 23, 2014 in European Application Serial No. 12198485, (University of Western Australia Exhibit 2147, filed Apr. 3, 2015 in Interferences 106007, 106008, and 106013, pp. 1-8).
Response to Office Action and Amendments to the Claims for U.S. Appl. No. 13/550,210, 10 pages, dated May 12, 2014 (Exhibit No. 2064 filed in interferences 106008, 106013, 106007 on Nov. 18, 2014).
Rhodes et al., "BioMarin Bulks Up," BioCentury, pp. 6-8 (Dec. 2014), Exhibit No. 1193 filed in Interferences 106,007 and 106,008 on Feb. 17, 2015.
RNA Isolation Using RNA-BEE, pp. 1, Exhibit No. 1175 filed in Interferences 106,007 and 106,008 on Feb. 16, 2015.
Roberts, Roland G. et al., "Exon Structure of the Human Dystrophin Gene," Genomics, vol. 16:536-538 (1993).
Roest et al., "Application of In Vitro Myo-Differentiation of Non-Muscle Cells to Enhance Gene Expression and Facilitate Analysis of Muscle Proteins," Neuromuscul. Disord., vol. 6, No. 3, pp. 195-202 (May 1996), Exhibit No. 1124 filed in interferences 106,007 and 106,008 on Feb. 17, 2015.
Rosso, Mario G. et al., "An *Arabidopsis thaliana* T-DNA mutagenized population (GABI-Kat) for flanking sequence tag-based reverse genetics," Plant Molecular Biology, vol. 53:247-259 (2003).
Saito, T. et al., "First-in-Human Study of NS-065/NCNP-01; the Morpholino Based Antisense Oligonucleotide for Exon 53 Skipping in Duchenne Muscular Dystrophy," ASGCT meeting, May 13, 2015, Abstract [136] 1 page.
Saito, T. et al., "First-in-Human Study of NS-065/NCNP-01; the Morpholino Based Antisense Oligonucleotide for Exon 53 Skipping in Duchenne Muscular Dystrophy," ASGCT meeting, May 13, 2015, pp. 1-11.
Classification Excerpts from USPC System, 21 pages, (Academisch Ziekenhuis Leiden Exhibit 1234, filed May 5, 2015 in Interference 106007 and 106008).
Collins, C.A. et al., "Duchenne's muscular dystrophy: animal models used to investigate pathogenesis and develop therapeutic strategies," Int. J. Exp. Pathol., vol. 84(4):165-172 (2003).
Confirmation of Dystrophin Exon 48 to 50 Deletion in Cell Line 8036 Laboratory Notebook Entry, pp. 3, Exhibit No. 1167 filed in Interferences 106,007 and 106,008 on Feb. 16, 2015.

(56) References Cited

OTHER PUBLICATIONS

Confirmation of Dystrophin Exon 52 Deletion in Cell Line R1809 Laboratory; Notebook Entry, pp. 3, Exhibit No. 1168 filed in Interferences 106,007 and 106,008 on Feb. 16, 2015.
Confirmatory Study of Eteplirsen in DMD Patients, An Open-Label, Multi-Center, 48-Week Study With a Concurrent Untreated Control Arm to Evaluate the Efficacy and Safety of Eteplirsen in Duchenne Muscular Dystrophy ,Clinical Trials.gov, Clinical Trial Identifier NCT02255552, Oct. 1, 2014, 3 pages.
*Coolidge* v. *Efendic*, 2008 WL 2080735, Int. No. 105,457 (BPAI May 16, 2008), 42 pages, (Academisch Ziekenhuis Leiden Exhibit 1235, filed May 5, 2015 in Interference 106007 and 106008).
Corey, David R. et al., Morpholino antisense oligonucleotides: tools for investigating vertebrate development, Genome Biology, vol. 2(5):1015.1-1015.3 (2001) (Exhibit No. 1026 filed in interferences 106008, 106007 on Nov. 18, 2014).
Corrected Priority Statement filed by UWA in Int. No. 106,008 (as PN 219),pp. 5, Exhibit No. 1002 filed in Interference 106,013 on Feb. 17, 2015.
Cortes et al., "Mutations in the conserved loop of human U5 snRNA generate use of novel cryptic 5' splice sites in vivo," EMBO J., vol. 12, No. 13, pp. 5181-5189 (1993), Exhibit No. 1187 filed in Interferences 106,007 and 106,008 on Feb. 17, 2015.
Crooke, Stanley T., Antisense Drug Technology, Principles, Strategies, and Applications, Marcel Dekker, Inc., New York, Chapters 15 and 16, pp. 375-389, 391-469 (2001) (Exhibit No. 2075 filed in interferences 106008, 106013, 106007 on Nov. 18, 2014).
Curriculum Vitae of Judith van Deutekom, pp. 6, Exhibit No. 1126 filed in interferences 106,007 and 106,008 on Feb. 17, 2015.
Curriculum Vitae, Erik Joseph Sontheimer, 18 pages, dated Sep. 29, 2014 (Exhibit No. 1013 filed in interferences 106008, 106007 on Nov. 18, 2014).
CV, Professor Matthew J.A. Wood, 3 pages (Exhibit No. 2003 filed in interferences 106008, 106007 on Nov. 18, 2014).
Davis, Richard J. et al., "Fusion of PAX7 to Fkhr by the Variant t(1;13)(p36;q14) Translocation in Alveolar Rhabdomyosarcoma," Cancer Research, vol. 54:2869-2872 (1994) (Exhibit No. 1027 filed in interferences 106008, 106007 on Nov. 18, 2014).
De Angelis, Femanda Gabriella et al., "Chimeric snRNA molecules carrying antisense sequences against the splice junctions of exon 51 of the dystrophic pre-mRNA induce exon skipping and restoration of a dystrophin synthesis in 48-50 DMD cells," PNAS, vol. 99(14):9456-9461 (2002).
Decision on Appeal, *Ex Parte Martin Gleave and Hideaki Miyake*, Appeal No. 2005-2447, U.S. Appl. No. 09/619,908 (Jan. 31, 2006) (2009 WL 6927761 (Bd.Pat.App.& Interf.), pp. 12, Exhibit No. 1207 filed in Interferences 106,007 and 106,008 on Feb. 17, 2015.
Decision on Request for ReHearing, *Ex Parte Roderick John Scott*, Appeal No. 2008-004077, U.S. Appl. No. 10/058,825 (Jan. 6, 2010) (2010 WL 191079 (Bd.Pat.App. & Interf.),pp. 21, Exhibit No. 1208 filed in Interferences 106,007 and 106,008 on Feb. 17, 2015.
Declaration of Judith C.T. van Deutekom Under 37 C.F.R. § 1.132, filed on Jan. 27, 2012, in U.S. Appl. No. 90/011,320, regarding U.S. Pat. No. 7,534,879, (University of Western Australia Exhibit 2133, filed Apr. 3, 2015 in Interferences 106007, 106008, and 106013, pp. 1-10).
Declaration of Judith van Deutekom, pp. 45, Exhibit No. 1125 filed in interferences 106,007 and 106,008 on 7ebruary 17, 2015.
Dellorusso, Christiana et al., "Functional correction of adult mdx mouse muscle using gutted adenoviral vectors expressing full-length dystrophin," PNAS, vol. 99(20):12979-12984 (2002).
Deposition Transcript of Erik J. Sontheimer, Ph.D. of Jan. 21, 2015 (99 pages), Exhibit No. 1215 filed in Interferences 106,007 and 106,008 on Feb. 17, 2015.
Deposition Transcript of Matthew J. A. Wood, M.D., D. Phil., Jan. 22, 2015, including Errata Sheet, pp. 198, Exhibit No. 1007 filed in Interference 106,013 on Feb. 17, 2015.
Deposition Transcript of Matthew J. A. Wood, M.D., D. Phil., pp. 196, Exhibit No. 1122 filed in interferences 106,007 and 106,008 on Feb. 17, 2015.

Desalting of Oligonucleotides, pp. 2, Exhibit No. 1132 filed in Interferences 106,007 and 106,008 on Feb. 17, 2015.
Dirksen, Wessel P. et al., "Mapping the SF2/ASF Binding Sites in the Bovine Growth Hormone Exonic Splicing Enhancer," The Journal of Biological Chemistry, vol. 275(37):29170-29177 (2000).
Dominski, Zbigniew et al., "Identification and Characterization by Antisense Oligonucleotides of Exon and Intron Sequences Required for Splicing," Molecular and Cellular Biology, vol. 14(11):7445-7454 (1994).
Dominski, Zbigniew et al., "Restoration of correct splicing in thalassemic pre-mRNA by antisense oligonucleotides," Proc. Natl. Acad. Sci. USA, vol. 90:8673-8677 (1993).
Doran, Philip et al., "Proteomic profiling of antisense-induced exon skipping reveals reversal of pathobiochemical abnormalities in dystrophic mdx diaphragm," Proteomics, vol. 9:671-685, DOI 10.1002/pmic.200800441 (2009).
Douglas, Andrew G.L. et al., "Splicing therapy for neuromuscular disease," Molecular and Cellular Neuroscience, vol. 56:169-185 (2013) (Exhibit No. 2005 filed in interferences 106008, 106013, 106007 on Nov. 18, 2014).
Doyle, Donald F., et al. (2001) "Inhibition of Gene Expression Inside Cells by PeptideNucleic Acids: Effect of mRNA Target Sequence, Mismatched Bases, and PNA Length," Biochemistry 40:53-64, (Exhibit No. 2123 filed in interferences 106,007 and 106,008 on Feb. 17, 2015.
Dr. Wood Errata Sheet—Jan. 22, 2015, pp. 2, Exhibit No. 1227 filed in Interferences 106,007 and 106,008 on Feb. 17, 2015.
Dunckley, Matthew G. et al., "Modification of splicing in the dystrophin gene in cultured Mdx muscle cells by antisense oligoribonucleotides," Human Molecular Genetics, vol. 5(1):1083-1090 (1995).
Dunckley, Matthew G. et al., "Modulation of Splicing in the DMD Gene by Antisense Oligoribonucleotides," Nucleosides & Nucleotides, vol. 16(7-9):1665-1668 (1997).
Eckstein, F., "Nucleoside Phosphorothioates," Ann. Rev. Biochem., vol. 54:367-402 (1985) (Exhibit No. 1028 filed in interferences 106008, 106007 on Nov. 18, 2014).
Elayadi, Anissa N. et al., "Application of PNA and LNA oligomers to chemotherapy," Current Opinion in Investigational Drugs, vol. 2(4):558-561 (2001).
Email from Danny Huntington to Interference Trial Section, dated Sep. 21, 2014, pp. 2, Exhibit No. 3001 filed in Interference 106,007, 106,008, and 106,013 on Sep. 26, 2014.
Email From Sharon Crane to Interference Trial Section, dated Nov. 13, 2014, pp. 2, Exhibit No. 3002 filed in Interference 106,007, 106,008, and 106,013 on dated Nov. 14, 2014.
Emery, A.E. H., "Population frequencies of inherited neuromuscular diseases—a world survey," Neuromuscul Disord 1991;1:19-29.
Errata sheet for the Jan. 22, 2015 deposition of Matthew J. A. Wood, M.D., D. Phil., 2 pages, (Exhibit No. 2128 filed in interferences 106,007 and 106,008 on Feb. 17, 2015.
Errata sheet for the Mar. 12, 2015 deposition of Erik J. Sontheimer, Ph.D., (University of Western Australia Exhibit 2149, filed Apr. 3, 2015 in Interferences 106007, 106008, and 106013, p. 1).
Errata to the Sarepta Briefing Information for the Apr. 25, 2016 Meeting of the Peripheral and Central Nervous System Drugs Advisory Committee, Eteplirsen Errata Document, NDA 206488, 5 pages.
Errington, Stephen J. et al., "Target selection for antisense oligonucleotide induced exon skipping in the dystrophin gene," The Journal of Gene Medicine, vol. 5:518-527 (2003).
European Office Action for Application No. 09752572.9, 5 pages, dated Feb. 29, 2012.
European Response, Application No. 10004274.6, 7 pages, dated Nov. 5, 2013 (Exhibit No. 1060 filed in interferences 106008, 106007 on Nov. 18, 2014).
European Response, Application No. 12198517.0, 7 pages, dated Oct. 21, 2014 (Exhibit No. 2084 filed in interferences 106008, 106013, 106007 on Nov. 18, 2014).
European Search Report for Application No. 10004274.6, 12 pages, dated Jan. 2, 2013.
European Search Report, EP15168694.6, dated Jul. 23, 2015, pp. 1-8.

(56) References Cited

OTHER PUBLICATIONS

Excerpts from Prosecution History of U.S. Appl. No. 13/741,150: Notice of Allowance dated Mar. 16, 2015; List of References cited by Applicant and Considered by Examiner; Notice of Allowance and Fees due dated Sep. 18, 2014; Amendment in Response to Non-Final Office Action dated Jul. 11, 2014, (Academisch Ziekenhuis Leiden Exhibit 1229, filed Apr. 3, 2015 in Interference 106007 and 106008, pp. 1-133).

Excerpts from Prosecution History of U.S. Appl. No. 13/826,880: Notice of Allowance dated Jan. 26, 2015 and Amendment in Response to Non-Final Office Action dated Oct. 15, 2014, (Academisch Ziekenhuis Leiden Exhibit 1228, filed Apr. 3, 2015 in Interference 106007 and 106008, pp. 1-16).

Excerpts from Yeo (Ed.), "Systems Biology of RNA Binding Proteins," Adv. Exp. Med. Biol., Chapter 9, 56 pages (2014), (Academisch Ziekenhuis Leiden Exhibit 1232, filed Apr. 3, 2015 in Interference 106007 and 106008, pp. 1-56).

Laboratory Notebook Entry (Exon 51 Experiments): RT-PCR Analysis of 8036 Cells, pp. 2, Exhibit No. 1179 filed in Interferences 106,007 and 106,008 on Feb. 16, 2015.

Laboratory Notebook Entry (Exon 51 Experiments): RT-PCR Analysis of KM155.C25 Cells, pp. 2, Exhibit No. 1178 filed in Interferences 106,007 and 106,008 on Feb. 16, 2015.

Laboratory Notebook Entry (Exon 51 Experiments): Transfection of 8036 Cells, pp. 1, Exhibit No. 1172 filed in Interferences 106,007 and 106,008 on Feb. 16, 2015.

Laboratory Notebook Entry (Exon 51 Experiments): Transfection of KM155.C25 Cells, pp. 1, Exhibit No. 1171 filed in Interferences 106,007 and 106,008 on Feb. 16, 2015.

Laboratory Notebook Entry (Exon 53 Experiments): RT-PCR Analysis of KM155.C25 Cells, pp. 2, Exhibit No. 1180 filed in Interferences 106,007 and 106,008 on Feb. 16, 2015.

Laboratory Notebook Entry (Exon 53 Experiments): RT-PCR Analysis of R1809 Cells, pp. 2, Exhibit No. 1181 filed in Interferences 106,007 and 106,008 on Feb. 16, 2015.

Laboratory Notebook Entry (Exon 53 Experiments): Transfection of KM155.C25 Cells, pp. 1, Exhibit No. 1173 filed in Interferences 106,007 and 106,008 on Feb. 16, 2015.

Laboratory Notebook Entry (Exon 53 Experiments): Transfection of R1809 Cells, pp. 1, Exhibit No. 1174 filed in Interferences 106,007 and 106,008 on Feb. 16, 2015.

Claims from U.S. Appl. No. 11/233,495, 6 pages, dated Sep. 21, 2005 (Exhibit No. 2068 filed in interferences 106008, 106013, 106007 on Nov. 18, 2014).

Laboratory Notebook Entry: General RNA recovery, pp. 2, Exhibit No. 1176 filed in interferences 106,007 and 106,008 on Feb. 16, 2015.

Laboratory Notebook Entry: Lab-on-a-Chip Analysis, pp. 3, Exhibit No. 1184 filed in Interferences 106,007 and 106,008 on Feb. 16, 2015.

Larsen et al., "Antisense properties of peptide nucleic acid," Biochim. Et Biophys. Acta, vol. 1489, pp. 159-166 (1999), Exhibit No. 1190 filed in Interferences 106,007 and 106,008 on Feb. 17, 2015.

Letter from the FDA to Sarepta Therapeutics, Inc., Re: Accelerated Approval for the use of Exondys 51 (eteplirsen), FDA Reference ID: 3987286, dated Sep. 19, 2016, 11 pages.

Letter to the U.S. Food and Drug Administration, (Dr. Billy Dunn, M.D. Director Division of Neurology Products, Office of Drug Evaluation 1, Center for Drug Evaluation and Research), for the Peripheral and Central Nervous System Advisory Committee Meeting (AdComm) supporting approval of eteplirsen, dated Feb. 24, 2016, 4 pages.

Letter to the U.S. Food and Drug Administration, (Dr. Janet Woodcock, M.D. Director, CDER), from the Congress of The United States regarding Duchenne muscular dystrophy, dated Feb. 17, 2016, 7 pages.

List of Publications for Matthew J. A. Wood, M.D., D. Phil., 11 pages, (Exhibit No. 2124 filed in interferences 106,007 and 106,008 on Feb. 17, 2015.

Liu, Hong-Xiang et al., "Identification of functional exonic splicing enhancer motifs recognized by individual SR proteins," Genes & Development, vol. 12:1998-2012 (1998).

Lu et al, "Massive Idiosyncratic Exon Skipping Corrects the Nonsense Mutation in Dystrophic Mouse Muscle and Produces Functional Revertant Fibers by Clonal Expansion," The Journal of Cell Biology, vol. 148(5): 985-995, Mar. 6, 2000 ("Lu et al.") (Exhibit No. 1082 filed in interferences 106008, 106007 on Dec. 23, 2014).

Lu, Qi Long et al., "Functional amounts of dystrophin produced by skipping the mutated exon in the mdx dystrophic mouse," Nature Medicine, vol. 9(8):1009-1014 (2003).

Lu, Qi-long et al., "What Can We Learn From Clinical Trials of Exon Skipping for DMD?" Molecular Therapy—Nucleic Acids, vol. 3:e152, doi:10.1038/mtna.2014.6, 4 pages (2014).

Lyophilisation of Oligonucleotides, pp. 2, Exhibit No. 1133 filed in Interferences 106,007 and 106,008 on Feb. 17, 2015.

Mann, Christopher J. et al., "Antisense-induced exon skipping and synthesis of dystrophin in the mdx mouse," PNAS, vol. 98(1):42-47 (2001).

Mann, Christopher J. et al., "Improved antisense oligonucleotide induced exon skipping in the mdx mouse model of muscular dystrophy," The Journal of Gene Medicine, vol. 4:644-654 (2002).

Mannino, Raphael J. et al., "Liposome Mediated Gene Transfer," BioTechniques, vol. 6(7):682-690 (1988).

Manual of Patent Examining Procedure 2308.02 (6th ed., rev. 3, Jul. 1997), (University of Western Australia Exhibit 2143, filed Apr. 3, 2015 in Interferences 106007, 106008, and 106013, pp. 1-2).

Manzur A, et al.,. "Glucocorticoid corticosteroids for Duchenne muscular dystrophy," Cochrane Database Syst Rev. 2004;(2):CD003725.

Marshall, N.B. et al., "Arginine-rich cell-penetrating peptides facilitate delivery of antisense oligomers into murine leukocytes and alter pre-mRNA splicing," Journal of Immunological Methods, vol. 325:114-126 (2007).

Mathews et al., "Expanded Sequence Dependence of Thermodynamic Parameters Improves Prediction of RNA Secondary Structure," J. Mol. Biol. 288:911-940 (1999), (University of Western Australia Exhibit 2131, filed Apr. 3, 2015 in Interferences 106007, 106008, and 106013, pp. 1-31).

Mathews et al., "Expanded Sequence Dependence of Thermodynamic Parameters Improves Prediction of RNA Secondary Structure," J. Mol. Biol., vol. 288, pp. 911-940 (1999), Exhibit No. 1212 filed in Interferences 106,007 and 106,008 on Feb. 17, 2015.

Matsuo, Masafumi et al., "Exon Skipping during Splicing of Dystrophin mRNA Precursor due to an Intraexon Deletion in the Dystrophin Gene of Duchenne Muscular Dystrophy Kobe," J. Clin. Invest., vol. 87:2127-2131 (1991).

Matsuo, Masafumi et al., "Treatment of Duchenne Muscular Dystrophy with Oligonucleotides against an Exonic Splicing Enhancer Sequence," Basic Appl. Myol., vol. 13(6):281-285 (2003).

Matsuo, Masafumi, "Duchenne and Becker Muscular Dystrophy: From Gene Diagnosis to Molecular Therapy," IUBMB Life, vol. 53:147-152 (2002).

Matsuo, Masafumi, "Duchenne/Becker muscular dystrophy: from molecular diagnosis to gene therapy," Brain & Development, vol. 18:167-172 (1996).

Matteucci, Mark, "Structural modifications toward improved antisense oligonucleotides," Perspectives in Drug Discovery and Design, vol. 4:1-16 (1996).

Mazzone E, et al. "Functional changes in Duchenne muscular dystrophy: a 12-month longitudinal cohort study," Neurology 2011;77(3):250-6.

McCarville, M. Beth et al., "Rhabdomyosarcoma in Pediatric Patients: The Good, the Bad, and the Unusual," AJR, vol. 176:1563-1569 (2001) (Exhibit No. 1034 filed in interferences 106008, 106007 on Nov. 18, 2014).

McClorey, G. et al., "Antisense oligonucleotide-induced exon skipping restores dystrophin expression in vitro in a canine model of DMD," Gene Therapy, vol. 13:1373-1381 (2006).

McClorey, G. et al., "Induced dystrophin exon skipping in human muscle explants," Neuromuscular Disorders, vol. 16:583-590 (2006).

(56) References Cited

OTHER PUBLICATIONS

McClorey, Graham et al., "Splicing intervention for Duchenne muscular dystrophy," Current Opinion in Pharmacology, vol. 5:529-534 (2005).
McDonald CM, et al., "Profiles of Neuromuscular Diseases, Duchenne muscular dystrophy," Am J Phys Med Rehabil 1995;74:S70-S92.
McDonald CM, et al., "The 6-minute walk test as a new outcome measure in Duchenne muscular dystrophy," Muscle Nerve 2010;41:500-10.
McDonald CM, et al., "The 6-minute walk test in Duchenne/Becker muscular dystrophy: longitudinal observations," Muscle Nerve 2010;42: 966-74.
Mendell JR et al., "Evidence-based path to newborn screening for Duchenne muscular Dystrophy," Ann Neurol 2012;71:304-13.
Mendell JR, et al., "Dystrophin immunity revealed by gene therapy in Duchenne muscular dystrophy," N Engl J Med 2010;363:1429-37.
Mendell JR, et al., "Randomized, double-blind six-month trial of prednisone in Duchenne's muscular dystrophy," N Engl J Med 1989;320:1592-97.
Mendell, Jerry R. et al., "Eteplirsen for the Treatment of Duchenne Muscular Dystrophy," Ann. Neural., vol. 74:637-647 (2013) (Exhibit No. 2058 filed in interferences 106008, 106013, 106007 on Nov. 18, 2014).
Mendell, Jerry R. et al., "Eteplirsen in Duchenne Muscular Dystrophy (DMD): 144 Week Update on Six-Minute Walk Test (6MWT) and Safety," slideshow, presented at the 19th International Congress of the World Muscle Society, 17 pages (2014) (Exhibit No. 2059 filed in interferences 106008, 106013, 106007 on Nov. 18, 2014).
Mendell, Jerry R. et al., "Gene therapy for muscular dystrophy: Lessons learned and path forward," Neuroscience Letters, vol. 527:90-99 (2012).
Merlini L, et al., "Early corticosteroid treatment in 4 Duchenne muscular dystrophy patients: 14-year follow-up," Muscle Nerve 2012;45:796-802.
Mfold illustrations for Exon 51 and Exon 53 with varying amounts of intron sequence, (University of Western Australia Exhibit 2132, filed Apr. 3, 2015 in Interferences 106007, 106008, and 106013, pp. 1-2).
*University of Western Australia* v. *Academisch Ziekenhuis Leiden*, UWA Exhibit List as of Nov. 18, 2014, 7 pages, Patent Interference No. 106,008, dated Nov. 18, 2014 (Doc 216).
*University of Western Australia* v. *Academisch Ziekenhuis Leiden*, UWA Exhibit list, 7 pages, Patent Interference No. 106,007, dated Nov. 18, 2014 (Doc 213).
*University of Western Australia* v. *Academisch Ziekenhuis Leiden*, UWA Exhibit list, 7 pages, Patent Interference No. 106,013, dated Nov. 18, 2014 (Doc 134).
*University of Western Australia* v. *Academisch Ziekenhuis Leiden*, UWA Exhibit List, 7 pages, Patent Interference Nos. 106,008, dated Dec. 12, 2014 (Doc 221).
*University of Western Australia* v. *Academisch Ziekenhuis Leiden*, UWA Exhibit List, 8 pages, Patent Interference No. 106,007, dated Dec. 12, 2014 (Doc 217).
*University of Western Australia* v. *Academisch Ziekenhuis Leiden*, UWA List of Proposed Motions, Patent Interference No. 106,007, 7 pages, dated Sep. 10, 2014 (Doc 17).
*University of Western Australia* v. *Academisch Ziekenhuis Leiden*, UWA List of Proposed Motions, Patent Interference No. 106,008, 6 pages, dated Sep. 10, 2014 (Doc 16).
*University of Western Australia* v. *Academisch Ziekenhuis Leiden*, UWA Miscellaneous Motion 1 (for authorization to file terminal disclaimer), 5 pages, Patent Interference No. 106,008, dated Oct. 17, 2014 (Doc 22).
*University of Western Australia* v. *Academisch Ziekenhuis Leiden*, UWA Motion 1 (For Judgment Under 35 U.S.C., section 112(a)), 40 pages, Patent Interference No. 106,007, dated Nov. 18, 2014 (Doc 210).
*University of Western Australia* v. *Academisch Ziekenhuis Leiden*, UWA Motion 1 (For Judgment Under 35 § 112(a)) Patent Interference No. 106,008 (Doc 213), 38 Pages, on Nov. 18, 2014.
*University of Western Australia* v. *Academisch Ziekenhuis Leiden*, UWA Motion 1 (To Maintain Interference between UWA U.S. Pat. No. 8,486,907 and AZL U.S. Appl. No. 14/198,992), 45 pages, Patent Interference No. 106,013, dated Nov. 18, 2014 (Doc 133).
*University of Western Australia* v. *Academisch Ziekenhuis Leiden*, UWA Motion 2 (For Judgment Under 35 U.S.C. section 112(b)), 32 pages, Patent Interference No. 106,008, dated Nov. 18, 2014 (Doc 214).
*University of Western Australia* v. *Academisch Ziekenhuis Leiden*, UWA Motion 2 (For Judgment Under 35 U.S.C. section 112(b)), 34 pages, Patent Interference No. 106,007, dated Nov. 18, 2014 (Doc 211).
*University of Western Australia* v. *Academisch Ziekenhuis Leiden*, UWA Motion 3 (For judgment that Claims 11-12, 14-15, and 17-29 of U.S. Appl. No. 13/550,210 are barred under 35 U.S.C. section 135(b)), 25 Pages, Patent Interference No. 106,008, dated Nov. 18, 2014 (Doc 215).
*University of Western Australia* v. *Academisch Ziekenhuis Leiden*, UWA Notice of Filing Priority Statement, 2 pages, Patent Interference No. 106,008, dated Nov. 18, 2014 (Doc 218).
*University of Western Australia* v. *Academisch Ziekenhuis Leiden*, UWA Notice of Recent Authority, filed in Patent Interference No. 106,007, Jul. 2, 2015, pp. 1-16 (Doc 469).
*University of Western Australia* v. *Academisch Ziekenhuis Leiden*, UWA Notice of Recent Authority, filed in Patent Interference No. 106,007, Sep. 2, 2015, pp. 1-18 (Doc 470).
*University of Western Australia* v. *Academisch Ziekenhuis Leiden*, UWA Notice of Recent Authority, filed in Patent Interference No. 106,008, Jul. 2, 2015, pp. 1-16 (Doc 477).
*University of Western Australia* v. *Academisch Ziekenhuis Leiden*, UWA Notice of Recent Authority, filed in Patent Interference No. 106,008, Sep. 2, 2015, pp. 1-18 (Doc 478).
*University of Western Australia* v. *Academisch Ziekenhuis Leiden*, UWA Notice of Related Proceedings, Patent Interference No. 106,007, 3 pages, dated Aug. 1, 2014 (Doc 11).
*University of Western Australia* v. *Academisch Ziekenhuis Leiden*, UWA Notice of Related Proceedings, Patent Interference No. 106,008, 5 pages, dated Aug. 7, 2014 (Doc 11).
*University of Western Australia* v. *Academisch Ziekenhuis Leiden*, UWA Notice of Related Proceedings, Patent Interference No. 106,013, 3 pages, dated Oct. 14, 2014 (Doc 6).
U.S. Pat. No. 7,960,541 (Wilton et al.), pp. 84, Exhibit No. 1002 filed in interferences 106,007 and 106,008 on Nov. 18, 2014.
U.S. Pat. No. 8,450,474 (Wilton et al.), pp. 95, Exhibit No. 1087 filed in interferences 106,007 and 106,008 on Feb. 13, 2015.
U.S. Pat. No. 8,455,634 (Wilton et al.) pp. 95, Exhibit No. 1088 filed in interferences 106,007 and 106,008 on Feb. 13, 2015.
U.S. Pat. No. 8,455,635 (Wilton et al.), pp. 96, Exhibit No. 1089 filed in interferences 106,007 and 106,008 on Feb. 13, 2015.
U.S. Pat. No. 8,455,636 (Wilton et al.), pp. 92, Exhibit No. 1003 filed in interferences 106,007 and 106,008 on Nov. 18, 2014.
U.S. Pat. No. 8,476,423 (Wilton et al.), pp. 95, Exhibit No. 1111 filed in interferences 106,007 and 106,008 on Feb. 13, 2015.
U.S. Pat. No. 8,501,703 (Bennett et al.), pp. 16, Exhibit No. 1090 filed in interferences 106,007 and 106,008 on Feb. 13, 2015.
U.S. Pat. No. 8,501,704 (Mourich et al.), pp. 39, Exhibit No. 1091 filed in interferences 106,007 and 106,008 on Feb. 13, 2015.
U.S. Pat. No. 8,524,676 (Stein et al.), pp. 28, Exhibit No. 1092 filed in interferences 106,007 and 106,008 on Feb. 13, 2015.
U.S. Pat. No. 8,524,880 (Wilton et al.), pp. 89, Exhibit No. 1093 filed in interferences 106,007 and 106,008 on Feb. 13, 2015.
U.S. Pat. No. 8,536,147 (Weller et al.), pp. 95, Exhibit No. 1094 filed in interferences 106,007 and 106,008 on Feb. 17, 2015,Doc 251.
U.S. Pat. No. 8,592,386 (Mourich et al.), pp. 46, Exhibit No. 1095 filed in interferences 106,007 and 106,008 on Feb. 13, 2015.
U.S. Pat. No. 8,618,270 (Iversen et al.), pp. 28, Exhibit No. 1096 filed in interferences 106,007 and 106,008 on Feb. 13, 2015.
U.S. Pat. No. 8,637,483 (Wilton et al.), pp. 157, Exhibit No. 1097 filed in interferences 106,007 and 106,008 on Feb. 13, 2015.

(56) References Cited

OTHER PUBLICATIONS

U.S. Pat. No. 8,697,858 (Iversen), pp. 95, Exhibit No. 1098 filed in interferences 106,007 and 106,008 on Feb. 13, 2015.
U.S. Pat. No. 8,703,735 (Iversen et al.) pp. 73, Exhibit No. 1099 filed in interferences 106,007 and 106,008 on Feb. 13, 2015.
U.S. Pat. No. 8,741,863 (Moulton et al.), pp. 68, Exhibit No. 1100 filed in interferences 106,007 and 106,008 on Feb. 13, 2015.
U.S. Pat. No. 8,759,307 (Stein et al.), pp. 35, Exhibit No. 1101 filed in interferences 106,007 and 106,008 on Feb. 13, 2015.
U.S. Pat. No. 8,779,128 (Hanson et al.), pp. 104, Exhibit No. 1102 filed in interferences 106,007 and 106,008 on Feb. 13, 2015.
U.S. Pat. No. 8,785,407 (Stein et al.), pp. 35, Exhibit No. 1103 filed in interferences 106,007 and 106,008 on Feb. 13, 2015.
U.S. Pat. No. 8,785,410 (Iversen et al.), pp. 20, Exhibit No. 1104 filed in interferences 106,007 and 106,008 on Feb. 13, 2015.
U.S. Pat. No. 8,835,402 (Kole et al.), pp. 27, Exhibit No. 1105 filed in interferences 106,007 and 106,008 on Feb. 13, 2015.
U.S. Pat. No. 8,865,883 (Sazani et al.), pp. 199, Exhibit No. 1106 filed in interferences 106,007 and 106,008 on Feb. 13, 2015.
U.S. Pat. No. 8,871,918 (Sazani et al.), pp. 195, Exhibit No. 1107 filed in interferences 106,007 and 106,008 on Feb. 13, 2015.
U.S. Pat. No. 8,877,725 (Iversen et al.), pp. 34, Exhibit No. 1108 filed in interferences 106,007 and 106,008 on Feb. 13, 2015.
U.S. Pat. No. 8,895,722 (Iversen et al.), pp. 29, Exhibit No. 1109 filed in interferences 106,007 and 106,008 on Feb. 13, 2015.
U.S. Pat. No. 8,906,872 (Iversen et al.), pp. 69, Exhibit No. 1110 filed in interferences 106,007 and 106,008 on Feb. 13, 2015.
US Abandonment for U.S. Appl. No. 13/902,376, 1 page, dated Jun. 12, 2014 (Exhibit No. 1047 filed in interferences 106008, 106007 on Nov. 18, 2014).
U.S. Appl. No. 11/570,691, filed Jan. 15, 2008, Stephen Donald Wilton.
U.S. Appl. No. 12/837,356, filed Jul. 15, 2010, Stephen Donald Wilton.
U.S. Appl. No. 12/837,359, filed Jul. 15, 2010, Stephen Donald Wilton.
U.S. Appl. No. 12/860,078, filed Aug. 20, 2010, Stehen Donald Wilton.
U.S. Appl. No. 13/168,857, filed Jun. 24, 2011, Stephen Donald Wilton.
U.S. Appl. No. 13/168,863, filed Jun. 24, 2011, Stephen Donald Wilton.
U.S. Appl. No. 13/270,500, filed Oct. 11, 2011, Stephen Donald Wilton.
U.S. Appl. No. 13/270,531, filed Oct. 11, 2011, Stephen Donald Wilton.
U.S. Appl. No. 13/270,744, filed Oct. 11, 2011, Stephen Donald Wilton.
U.S. Appl. No. 13/270,937, filed Oct. 11, 2011, Stephen Donald Wilton.
U.S. Appl. No. 13/270,992, filed Oct. 11, 2011, Stephen Donald Wilton.
U.S. Appl. No. 13/271,080, filed Oct. 11, 2011, Stephen Donald Wilton.
U.S. Appl. No. 13/727,415, filed Dec. 26, 2012, Stephen Donald Wilton.
U.S. Appl. No. 13/741,150, filed Jan. 14, 2013, Stephen Donald Wilton.
U.S. Appl. No. 13/826,613, filed Mar. 14, 2013, Stephen Donald Wilton.
U.S. Appl. No. 13/826,880, filed Mar. 14, 2013, Stephen Donald Wilton.
U.S. Appl. No. 13/902,376, filed May 24, 2013, Stephen Donald Wilton.
U.S. Appl. No. 13/963,578, filed Aug. 9, 2013, Stephen Donald Wilton.
U.S. Appl. No. 14/086,859, filed Nov. 21, 2013, Stephen Donald Wilton.
U.S. Appl. No. 14/178,059, filed Feb. 11, 2014, Stephen Donald Wilton.
U.S. Appl. No. 14/223,634, filed Mar. 24, 2014, Stephen Donald Wilton.
U.S. Appl. No. 14/273,318, filed May 8, 2014, Stephen Donald Wilton.
U.S. Appl. No. 14/273,379, filed May 8, 2014, Stephen Donald Wilton.
U.S. Appl. No. 14/316,603, filed Jun. 26, 2014, Stephen Donald Wilton.
U.S. Appl. No. 14/316,609, filed Jun. 26, 2014, Stephen Donald Wilton.
U.S. Appl. No. 14/317,952, filed Jun. 27, 2014, Stephen Donald Wilton.
U.S. Appl. No. 14/740,097, filed Jun. 15, 2015, Stephen Donald Wilton.
U.S. Appl. No. 14/852,090, filed Sep. 11, 2015, Stephen Donald Wilton.
U.S. Appl. No. 14/852,149, filed Sep. 11, 2015, Stephen Donald Wilton.
U.S. Appl. No. 14/857,555, filed Sep. 17, 2015, Stephen Donald Wilton.
U.S. Appl. No. 14/857,561, filed Stephen Donald Wilton.
U.S. Appl. No. 14/858,250, filed Sep. 18, 2015, Stephen Donald Wilton.
U.S. Appl. No. 15/274,719, filed Sep. 23, 2016, Stephen Donald Wilton.
U.S. Appl. No. 15/274,772, filed Sep. 23, 2016, Stephen Donald Wilton.
U.S. Appl. No. 15/349,535, filed Nov. 11, 2016, Stephen Donald Wilton.
U.S. Appl. No. 12/605,276, filed Oct. 23, 2009, Peter Sazani.
U.S. Appl. No. 13/829,545, filed Mar. 14, 2013, Peter Sazani.
U.S. Appl. No. 13/830,253, filed Mar. 14, 2013, Peter Sazani.
U.S. Appl. No. 14/523,610, filed Oct. 24, 2014, Peter Sazani.
U.S. Appl. No. 14/852,257, filed Sep. 11, 2015, Peter Sazani.
U.S. Appl. No. 14/852,264, filed Sep. 11, 2015, Peter Sazani.
U.S. Appl. No. 14/857,569, filed Sep. 17, 2015, Peter Sazani.
U.S. Appl. No. 14/857,590, filed Sep. 17, 2015, Peter Sazani.
U.S. Appl. No. 14/858,416, filed Sep. 18, 2015, Peter Sazani.
U.S. Appl. No. 14/743,856, filed Jun. 18, 2015, R.K. Bestwick.
U.S. Appl. No. 14/213,629, filed Mar. 14, 2014, E.M. Kaye.
U.S. Appl. No. 14/214,567, filed Mar. 14, 2014, E.M. Kaye.
U.S. Appl. No. 14/213,607, filed Mar. 14, 2014, R.K. Bestwick.
U.S. Appl. No. 14/214,480, filed Mar. 14, 2014, R.K. Bestwick.
U.S. Appl. No. 14/942,629, filed Nov. 16, 2015, R.K. Bestwick.
U.S. Appl. No. 13/509,331, filed Jul. 9, 2012, S.D. Wilton.
U.S. Appl. No. 14/108,137, filed Dec. 16, 2013, S.D. Wilton.
U.S. Appl. No. 14/944,886, filed Nov. 18, 2015, S.D. Wilton.
U.S. Appl. No. 14/213,641, filed Mar. 14, 2014, R.K. Bestwick.
U.S. Appl. No. 14/776,533, filed Sep. 14, 2015, R.K. Bestwick.
U.S. Appl. No. 11/570, Aug. 16, 2010.
U.S. Appl. No. 11/570,691, Mar. 15, 2010.
U.S. Appl. No. 11/570,691, May 26, 2009.
U.S. Appl. No. 12/837,356, May 3, 2013.
U.S. Appl. No. 12/837,356, Apr. 3, 2013.
U.S. Appl. No. 12/837,356, Aug. 2, 2012.
U.S. Appl. No. 12/837,359, Mar. 12, 2012.
U.S. Appl. No. 12/837,359, Oct. 5, 2011.
U.S. Appl. No. 12/837,359, Mar. 30, 2011.
U.S. Appl. No. 12/837,359, Dec. 22, 2010.
U.S. Appl. No. 12/860,078, Feb. 14, 2011.
U.S. Appl. No. 13/168,857, Jul. 12, 2012.
U.S. Appl. No. 13/168,863, Mar. 8, 2013.
U.S. Appl. No. 13/168,863, Oct. 11, 2012.
U.S. Appl. No. 13/168,863, Aug. 8, 2012.
U.S. Appl. No. 13/270,500, Mar. 15, 2013.
U.S. Appl. No. 13/270,500, Jul. 30, 2012.
U.S. Appl. No. 13/270,500, Mar. 14, 2012.
U.S. Appl. No. 13/270,531, Jun. 28, 2012.
U.S. Appl. No. 13/270,531, Mar. 14, 2012.
U.S. Appl. No. 13/270,744, Apr. 3, 2013.
U.S. Appl. No. 13/270,744, Aug. 6, 2012.
U.S. Appl. No. 13/270,744, Mar. 14, 2012.
U.S. Appl. No. 13/270,937, Feb. 25, 2013.

(56) References Cited

OTHER PUBLICATIONS

U.S. Appl. No. 13/270,937, Jun. 14, 2012.
U.S. Appl. No. 13/270,937, Mar. 14, 2012.
U.S. Appl. No. 13/270,992, Apr. 4, 2013.
U.S. Appl. No. 13/270,992, Jul. 30, 2012.
U.S. Appl. No. 13/270,992, Mar. 16, 2012.
U.S. Appl. No. 13/271,080, Mar. 26, 2013.
U.S. Appl. No. 13/271,080, Jul. 30, 2012.
U.S. Appl. No. 13/271,080, Mar. 14, 2012.
U.S. Appl. No. 13/727,415, Feb. 6, 2013.
U.S. Appl. No. 13/741,150, Mar. 16, 2015.
U.S. Appl. No. 13/741,150, Sep. 18, 2014.
U.S. Appl. No. 13/741,150, Apr. 11, 2014.
U.S. Appl. No. 13/741,150, Sep. 24, 2013.
U.S. Appl. No. 13/826,613, Jul. 22, 2014.
U.S. Appl. No. 13/826,613, Jan. 7, 2014.
U.S. Appl. No. 13/826,613, Jul. 17, 2013.
U.S. Appl. No. 13/826,880, Jun. 22, 2015.
U.S. Appl. No. 13/826,880, Jan. 26, 2015.
U.S. Appl. No. 13/826,880, Apr. 15, 2014.
U.S. Appl. No. 13/826,880, Sep. 11, 2013.
U.S. Appl. No. 13/902,376, Jun. 5, 2014.
U.S. Appl. No. 13/902,376, Jan. 7, 2014.
U.S. Appl. No. 13/902,376, Jul. 18, 2013.
U.S. Appl. No. 13/963,578, Sep. 24, 2013.
U.S. Appl. No. 14/086,859, Jun. 30, 2014.
U.S. Appl. No. 14/086,859, Jan. 27, 2014.
U.S. Appl. No. 14/178,059, Mar. 31, 2014.
U.S. Appl. No. 14/223,634, Apr. 15, 2015.
U.S. Appl. No. 14/273,318, Oct. 20, 2014.
U.S. Appl. No. 14/273,318, Jul. 3, 2014.
U.S. Appl. No. 14/273,379, Jul. 7, 2014.
U.S. Appl. No. 14/316,603, Mar. 10, 2015.
U.S. Appl. No. 14/316,603, Sep. 26, 2014.
U.S. Appl. No. 14/316,609, Mar. 16, 2015.
U.S. Appl. No. 14/316,609, Oct. 21, 2014.
U.S. Appl. No. 14/317,952, Mar. 18, 2015.
U.S. Appl. No. 14/317,952, Nov. 7, 2014.
U.S. Appl. No. 14/740,097, Nov. 14, 2016.
U.S. Appl. No. 14/740,097, Apr. 8, 2016.
U.S. Appl. No. 14/740,097, Nov. 6, 2015.
U.S. Appl. No. 14/852,090, Apr. 15, 2016.
U.S. Appl. No. 14/852,090, Jan. 6, 2016.
U.S. Appl. No. 14/852,090, Oct. 15, 2015.
U.S. Appl. No. 14/852,149, Nov. 24, 2015.
U.S. Appl. No. 14/857,555, Apr. 12, 2016.
U.S. Appl. No. 14/857,555, Nov. 6, 2015.
U.S. Appl. No. 14/857,561, Apr. 18, 2016.
U.S. Appl. No. 14/857,561, Mar. 15, 2016.
U.S. Appl. No. 14/857,561, Feb. 17, 2016.
U.S. Appl. No. 14/857,561, Jan. 8, 2016.
U.S. Appl. No. 14/857,561, Oct. 23, 2015.
U.S. Appl. No. 14/858,250, Nov. 6, 2015.
U.S. Appl. No. 12/605,276, Jun. 18, 2014.
U.S. Appl. No. 12/605,276, Oct. 18, 2013.
U.S. Appl. No. 12/605,276, Dec. 23, 2011.
U.S. Appl. No. 12/605,276, Aug. 24, 2011.
U.S. Appl. No. 12/605,276, Feb. 11, 2011.
U.S. Appl. No. 13/829,545, Jun. 6, 2014.
U.S. Appl. No. 13/830,253, Jun. 11, 2014.
U.S. Appl. No. 13/830,253, Nov. 26, 2013.
U.S. Appl. No. 14/523,610, May 11, 2016.
U.S. Appl. No. 14/852,257, Oct. 27, 2015.
U.S. Appl. No. 14/852,257, Oct. 6, 2015.
U.S. Appl. No. 14/852,264, Apr. 21, 2016.
U.S. Appl. No. 14/852,264, Oct. 21, 2015.
U.S. Appl. No. 14/857,569, May 6, 2016.
U.S. Appl. No. 14/857,569, Nov. 19, 2015.
U.S. Appl. No. 14/857,590, May 16, 2016.
U.S. Appl. No. 14/857,590, Nov. 19, 2015.
U.S. Appl. No. 14/858,416, May 4, 2016.
U.S. Appl. No. 14/858,416, Oct. 27, 2015.
U.S. Appl. No. 14/214,567, Jul. 7, 2016.
U.S. Appl. No. 14/214,567, Dec. 3, 2015.
U.S. Appl. No. 14/214,567, Jun. 24, 2015.
U.S. Appl. No. 14/213,607, Sep. 15, 2015.
U.S. Appl. No. 14/213,607, Apr. 1, 2015.
U.S. Appl. No. 14/213,607, Sep. 18, 2014.
U.S. Appl. No. 14/214,480, Aug. 2, 2016.
U.S. Appl. No. 14/214,480, Oct. 19, 2015.
U.S. Appl. No. 14/214,480, Apr. 17, 2015.
U.S. Appl. No. 14/214,480, Sep. 19, 2014.
U.S. Appl. No. 14/942,629, Aug. 16, 2016.
U.S. Appl. No. 13/509,331, Sep. 16, 2013.
U.S. Appl. No. 13/509,331, Jan. 28, 2013.
U.S. Appl. No. 14/108,137, Apr. 29, 2015.
U.S. Appl. No. 14/108,137, Oct. 9, 2015.
U.S. Appl. No. 14/108,137, Oct. 3, 2014.
U.S. Appl. No. 14/944,886, Apr. 27, 2017.
U.S. Appl. No. 14/944,886, Sep. 30, 2016.
U.S. Appl. No. 14/213,641, Aug. 1, 2016.
U.S. Appl. No. 14/213,641, Oct. 16, 2015.
U.S. Appl. No. 14/213,641, Mar. 31, 2015.
U.S. Appl. No. 14/213,641, Sep. 18, 2014.
U.S. Appl. No. 14/213,629, May 23, 2016.
U.S. Appl. No. 14/213,629, Aug. 21, 2015.
U.S. Appl. No. 14/213,629, Dec. 29, 2014.
U.S. Appl. No. 14/743,856, Aug. 1, 2016.
U.S. Appl. No. 14/776,533, Feb. 28, 2017.
U.S. Appl. No. 14/776,533, Aug. 3, 2016.
U.S. Appl. No. 15/274,719, Dec. 16, 2016.
U.S. Appl. No. 15/274,772, Dec. 30, 2016.
U.S. Appl. No. 15/274,772, Sep. 18, 2017.
*University of Western Australia* v. *Academisch Ziekenhuis Leiden*, Miscellaneous Order under 37 CFR 41.104(a), 4 pages, Patent Interference Nos. 106,007 and 106,008, dated Dec. 15, 2014.
*University of Western Australia* v. *Academisch Ziekenhuis Leiden*, Order—Authorizing Motions, Patent Interference No. 106,007, 3 pages, dated Sep. 26, 2014 (Doc 20).
*University of Western Australia* v. *Academisch Ziekenhuis Leiden*, Order—Authorizing Motions, Patent Interference No. 106,007, 6 pages, dated Sep. 23, 2014 (Doc 19).
*University of Western Australia* v. *Academisch Ziekenhuis Leiden*, Order—Authorizing Motions, Patent Interference No. 106,008, 6 pages, dated Sep. 23, 2014 (Doc 18).
*University of Western Australia* v. *Academisch Ziekenhuis Leiden*, Order—Miscelaneous, 2 pages, Patent Interference Nos. 106,007, 106,008, 106,013, dated Nov. 14, 2014.
*University of Western Australia* v. *Academisch Ziekenhuis Leiden*, Order to Show Cause—37 CFR§ 41.104(a), filed in Patent Interference No. 106,013, Jun. 22, 2015, pp. 1-3 (Doc 193).
*University of Western Australia* v. *Academisch Ziekenhuis Leiden*, Redeclaration, Patent Interference No. 106,008, 2 pages, dated Sep. 23, 2014 (Doc 19).
*University of Western Australia* v. *Academisch Ziekenhuis Leiden*, Second Declaration of Matthew J. A. Wood, M.D., D. Phil., Patent Interference Nos. 106,007 and 106,008, 78 pages, dated Feb. 17, 2015 (Exhibit No. 2116 filed in interferences 106,007 and 106,008,on Feb. 17, 2015.
*University of Western Australia* v. *Academisch Ziekenhuis Leiden*, Statement Concerning Initial Settlement Discussions, 3 pages, Patent Interference No. 106,013, (Doc 136), dated Dec. 30, 2014.
*University of Western Australia* v. *Academisch Ziekenhuis Leiden*, Statement Concerning Settlement Discussions, 3 pages, Patent Interference No. 106,007, (Doc 242), dated Dec. 30, 2014.
*University of Western Australia* v. *Academisch Ziekenhuis Leiden*, Statement Concerning Settlement Discussions, 3 pages, Patent Interference No. 106,008, (Doc 246), dated Dec. 30, 2014.
*University of Western Australia* v. *Academisch Ziekenhuis Leiden*, Statement Concerning Subsequent Settlement Discussions, filed in Patent Interference No. 106,013, Aug. 24, 2015, pp. 1-3 (Doc 195).

(56) References Cited

OTHER PUBLICATIONS

*University of Western Australia* v. *Academisch Ziekenhuis Leiden*, University of Western Austalia Response to Order to Show Cause, filed in Patent Interference No. 106,013, Jul. 20, 2015, pp. 1-28 (Doc 194).
*University of Western Australia* v. *Academisch Ziekenhuis Leiden*, University of Western Australia Exhibit List as of Apr. 10, 2015, filed in Patent Interference No. 106,007, Apr. 10, 2015, pp. 1-10 (Doc 456).
*University of Western Australia* v. *Academisch Ziekenhuis Leiden*, University of Western Australia Exhibit List as of Apr. 10, 2015, filed in Patent Interference No. 106,008, Apr. 10, 2015, pp. 1-10 (Doc 464).
*University of Western Australia* v. *Academisch Ziekenhuis Leiden*, University of Western Australia Exhibit List as of Apr. 3, 2015, filed in Interference 106007, Apr. 3, 2015, pp. 1-10 (Doc 431).
*University of Western Australia* v. *Academisch Ziekenhuis Leiden*, University of Western Australia Exhibit List as of Apr. 3, 2015, filed in Interference 106008, Apr. 3, 2015, pp. 1-10 (Doc 439).
*University of Western Australia* v. *Academisch Ziekenhuis Leiden*, University of Western Australia Exhibit List as of Apr. 3, 2015, filed in Interference 106013, Apr. 3, 2015, pp. 1-10 (Doc 153).
*University of Western Australia* v. *Academisch Ziekenhuis Leiden*, University of Western Australia Exhibit List as of Oct. 29, 2015, filed in Patent Interference No. 106,013, Oct. 29, 2015, pp. 1-10 (Doc 199).
*University of Western Australia* v. *Academisch Ziekenhuis Leiden*, University of Western Australia Miscellaneous Motion 4 (to exclude evidence), filed in Patent Interference No. 106,007, Apr. 10, 2015, pp. 1-21 (Doc 455).
*University of Western Australia* v. *Academisch Ziekenhuis Leiden*, University of Western Australia Miscellaneous Motion 4 (to exclude evidence), filed in Patent Interference No. 106,008, Apr. 10, 2015, pp. 1-21 (Doc 463).
*University of Western Australia* v. *Academisch Ziekenhuis Leiden*, University of Western Australia Opposition 1 (Regarding Patentability Under 35 U.S.C. § 102/103), 38 pages, Patent Interference No. 106,007, (Doc 393), dated Feb. 17, 2015.
*University of Western Australia* v. *Academisch Ziekenhuis Leiden*, University of Western Australia Opposition 1 (Regarding Patentability Under 35 U.S.C. § 102/103), 39 pages, Patent Interference No. 106,008, (Doc 402), dated Feb. 17, 2015.
*University of Western Australia* v. *Academisch Ziekenhuis Leiden*, University of Western Australia Opposition 2 (To Retain UWA's Benefit of AU 2004903474), 31 pages, Patent Interference No. 106,008, (Doc 403), dated Feb. 17, 2015.
*University of Western Australia* v. *Academisch Ziekenhuis Leiden*, University of Western Australia Opposition 2 (To Retain UWA's Benefit of AU 2004903474), 37 pages, Patent Interference No. 106,007, (Doc 394), dated Feb. 17, 2015.
*University of Western Australia* v. Academisch Ziekenhuis Leiden, University of Western Australia Opposition 3 (Regarding Patentability Under 35 U.S.C. § 101), 22 pages, Patent Interference No. 106,007, (Doc 395), dated Feb. 17, 2015.
*University of Western Australia* v. *Academisch Ziekenhuis Leiden*, University of Western Australia Opposition 3 (Regarding Patentability Under 35 U.S.C. § 101), 22 pages, Patent Interference No. 106,008, (Doc 404), dated Feb. 17, 2015.
*University of Western Australia* v. *Academisch Ziekenhuis Leiden*, University of Western Australia Opposition 4 (To deny entry of Azl's Proposed New Claims 104 and 105), 36 pages, Patent Interference No. 106,007, (Doc 397), dated Feb. 17, 2015.
*University of Western Australia* v. *Academisch Ziekenhuis Leiden*, University of Western Australia Opposition 4 (To deny entry of AZL's Proposed New Claims 30 and 31), 36 pages, Patent Interference No. 106,008, (Doc 405), dated Feb. 17, 2015.
*University of Western Australia* v. *Academisch Ziekenhuis Leiden*, University of Western Australia Reply 1 (to AZL Opposition 1), filed Apr. 3, 2015 in Interference 106007, pp. 1-28 (Doc 428).

*University of Western Australia* v. *Academisch Ziekenhuis Leiden*, University of Western Australia Reply 1 (to AZL Opposition 1), filed Apr. 3, 2015 in Interference 106008, pp. 1-28, (Doc 436).
*University of Western Australia* v. *Academisch Ziekenhuis Leiden*, University of Western Australia Reply 1 (to Maintain be Interference) filed Apr. 3, 2015 in Interference 106013, pp. 1-17 (Doc 152).
*University of Western Australia* v. *Academisch Ziekenhuis Leiden*, University of Western Australia Reply 2 (to AZL Opposition 2) filed Apr. 3, 2015 in Interference 106007, pp. 1-22 (Doc 429).
*University of Western Australia* v. *Academisch Ziekenhuis Leiden*, University of Western Australia Reply 2 (to AZL Opposition 2) filed Apr. 3, 2015 in Interference 106008, pp. 1-22 (Doc 437).
*University of Western Australia* v. *Academisch Ziekenhuis Leiden*, University of Western Australia Reply 3 (for Judgment under 35 U.S.C. §135(b)) filed Apr. 3, 2015 in Interference 106008, pp. 1-19 (Doc 438).
*University of Western Australia* v. *Academisch Ziekenhuis Leiden*, University of Western Australia Reply 3 (to Institute an Interference) filed Apr. 3, 2015 in Interference 106007, pp. 1-17 (Doc 430).
*University of Western Australia* v. *Academisch Ziekenhuis Leiden*, University of Western Australia Reply 4 (To Exclude Evidence), filed in Patent Interference No. 106,007, May 12, 2015, pp. 1-13 (Doc 467).
*University of Western Australia* v. *Academisch Ziekenhuis Leiden*, University of Western Australia Reply 4 (To Exclude Evidence), filed in Patent Interference No. 106,008, May 12, 2015, pp. 1-13 (Doc 475).
*University of Western Australia* v. *Academisch Ziekenhuis Leiden*, University of Western Australia Request for Oral Argument, filed in Patent Interference No. 106,007, Apr. 10, 2015, pp. 1-4 (Doc 457).
*University of Western Australia* v. *Academisch Ziekenhuis Leiden*, University of Western Australia Request for Oral Argument, filed in Patent Interference No. 106,008, Apr. 10, 2015, pp. 1-4 (Doc 465).
*University of Western Australia* v. *Academisch Ziekenhuis Leiden*, University of Western Australia Request for Oral Argument, filed in Patent Interference No. 106,013, Apr. 10, 2015, pp. 1-3 (Doc 190).
*University of Western Australia* v. *Academisch Ziekenhuis Leiden*, University of Western Australia Request for Rehearing, filed in Patent Interference No. 106,013, Oct. 29, 2015, pp. 1-20 (Doc 198).
*University of Western Australia* v. *Academisch Ziekenhuis Leiden*, University of Western Australia Revised Designation of Lead and Backup Counsel, 4 pages, Patent Interference No. 106,007, (Doc 415), dated Mar. 10, 2015.
*University of Western Australia* v. *Academisch Ziekenhuis Leiden*, University of Western Australia Revised Designation of Lead and Backup Counsel, 4 pages, Patent Interference No. 106,013, (Doc 150 ), dated Mar. 10, 2015.
*University of Western Australia* v. *Academisch Ziekenhuis Leiden*, University of Western Australia Revised Designation of Lead and Backup Counsel, 5 pages, Patent Interference No. 106,008, (Doc 423 ), dated Mar. 10, 2015.
*University of Western Australia* v. *Academisch Ziekenhuis Leiden*, University of Western Australia, Exhibit List as of Feb. 17, 2015, 8 pages, Patent Interference No. 106,007, (Doc No. 398) dated Feb. 17, 2015.
*University of Western Australia* v. *Academisch Ziekenhuis Leiden*, University of Western Australia, Exhibit List as of Feb. 17, 2015, 8 pages, Patent Interference No. 106,008, (Doc No. 406) dated Feb. 17, 2015.
*University of Western Australia* v. *Academisch Ziekenhuis Leiden*, UWA Clean Involved Claims and Sequence, Patent Interference No. 106,007, 8 pages, dated Aug. 1, 2014 (Doc 12).
*University of Western Australia* v. *Academisch Ziekenhuis Leiden*, UWA Clean Involved Claims and Sequence, Patent Interference No. 106,013, 7 pages, dated Oct. 14, 2014 (Doc 7).
*University of Western Australia* v. *Academisch Ziekenhuis Leiden*, UWA Clean Involved Claims and Sequences, Patent Interference No. 106,008, 8 pages, dated Aug. 7, 2014 (Doc 12).
AON PS1966 Mass Spectrometry Data, pp. 8, Exhibit No. 1154 filed in Interferences 106,007 and 106,008 on Feb. 16, 2015.
AON PS1966 UPLC Data, pp. 2, Exhibit No. 1165 filed in Interferences 106,007 and 106,008 on Feb. 16, 2015.

(56) References Cited

OTHER PUBLICATIONS

AON PS1967 Mass Spectrometry Data, pp. 7, Exhibit No. 1155 filed in Interferences 106,007 and 106,008 on Feb. 16, 2015.
AON PS1967 UPLC Data, pp. 2, Exhibit No. 1166 filed in Interferences 106,007 and 106,008 on Feb. 16, 2015.
AON PS229 (h53AON1) HPLC Chromatograph pp. 2, Exhibit No. 1140 filed in Interferences 106,007 and 106,008 on Feb. 16, 2015.
AON PS229 (h53AON1) HPLC Method Report, pp. 3, Exhibit No. 1139 filed in Interferences 106,007 and 106,008 on Feb. 16, 2015.
AON PS229 (h53AON1) Mass Spectrometry Data, pp. 3, Exhibit No. 1142 filed in Interferences 106,007 and 106,008 on Feb. 16, 2015.
AON PS229 (h53AON1) Synthesis Laboratory Notebook Entry, pp. 1, Exhibit No. 1137 filed in Interferences 106,007 and 106,008 on Feb. 16, 2015.
AON PS229L (h53A0N229L) Certificate of Analysis, pp. 1, Exhibit No. 1129 filed in Interferences 106,007 and 106,008 on Feb. 17, 2015.
AON PS43 (h51AON1) Certificate of Analysis, pp. 1, Exhibit No. 1134 filed in Interferences 106,007 and 106,008 on Feb. 16, 2015.
AON PS43 (h51AON1) HPLC Chromatogram, pp. 1, Exhibit No. 1131 filed in Interferences 106,007 and 106,008 on Feb. 17, 2015.
AON PS43 (h51AON1) HPLC Method Report, pp. 4, Exhibit No. 1130 filed in Interferences 106,007 and 106,008 on Feb. 17, 2015.
AON PS43 (h51AON1) Mass Spectrometry Data, pp. 3, Exhibit No. 1135 filed in Interferences 106,007 and 106,008 on Feb. 16, 2015.
AON PS43 (h51AON1) UPLC-UV Data, pp. 2, Exhibit No. 1136 filed in Interferences 106,007 and 106,008 on Feb. 16, 2015.
AONs PS1958, PS1959, PS1960, P51961, PlS1962, PS1963, PS1964, PS1965, PS1966, and PS1967 HPLC Method Report, pp. 3, Exhibit No. 1143 filed in Interferences 106,007 and 106,008 on Feb. 16, 2015.
Applicant-Initiated Interview Summary dated Apr. 8, 2013 in U.S. Appl. No. 13/094,548, (University of Western Australia Exhibit 2144, filed Apr. 3, 2015 in Interferences 106007, 106008, and 106013, pp. 1-11).
Arechavala-Gomeza V, et al., "Immunohistological intensity measurements as a tool to assess sarcolemma-associated protein expression," Neuropathol Appl Neurobiol 2010;36: 265-74.
Arechavala-Gomeza, V. et al., "Comparative Analysis of Antisense Oligonucleotide Sequences for Targeted Skipping of Exon 51 During Dystrophin Pre-mRNA Splicing in Human Muscle," Human Gene Therapy, vol. 18:798-810 (2007).
Arora, Vikram et al., "c-Myc Antisense Limits Rat Liver Regeneration and Indicates Role for c-Myc in Regulating Cytochrome P-450 3A Activity," The Journal of Pharmacology and Experimental Therapeutics, vol. 292(3):921-928 (2000).
*Asetek Danmark A/S v. CMI USA*, Inc., 2014 WL 5990699, N.D. Cal. 2014, 8 pages, (Academisch Ziekenhuis Leiden Exhibit 1237, filed May 5, 2015 in Interference 106007 and 106008).
Asvadi, Parisa et al., "Expression and functional analysis of recombinant scFv and diabody fragments with specificity for human RhD," Journal of Molecular Recognition, vol. 15:321-330 (2002).
Australian Application No. 2004903474, 36 pages, dated Jul. 22, 2005 (Exhibit No. 1004 filed in interferences 106008, 106007 on Nov. 18, 2014).
AVI BioPharma, Inc., "Exon 51 Sequence of Dystrophin," Document D19 as filed in Opposition of European Patent EP1619249, filed Jun. 23, 2009, 7 pages.
AZL's PCT/NL03/00214 (the as-filed AZL PCT Application) Exhibit No. 1006, filed in Interference No. 106,007, 64 pages, Dec. 23, 2014.
AZL's U.S. Appl. No. 14/295,311 and claims, as-filed Jun. 3, 2014 ("The '311 Application") (Exhibit No. 1077 filed in interferences 106008, 106007 on Dec. 23, 2014).
Azofeifa J, et al., "X-chromosome methylation in manifesting and healthy carriers of dystrophinopathies: concordance of activation ratios among first degree female relatives and skewed inactivation as cause of the affected phenotypes," Hum Genet 1995;96:167-176.

Beaucage, S.L. et al., "Deoxynucleoside Phosphoramidites—A New Class of Key Intermediates for Deoxypolynucleotide Synthesis," Tetrahedron Letters, vol. 22(20):1859-1862 (1981).
Bellare, Priya et al., "A role for ubiquitin in the spliceosome assembly pathway," Nature Structural & Molecular Biology, vol. 15(5):444-451 (2008) (Exhibit No. 1057 filed in interferences 106008, 106007 on Nov. 18, 2014).
Bellare, Priya et al., "Ubiquitin binding by a variant Jab1/MPN domain in the essential pre-mRNA splicing factor Prp8p," RNA, vol. 12:292-302 (2006) (Exhibit No. 1056 filed in interferences 106008,106007 on Nov. 18, 2014).
Bennett, C. Frank et al., "RNA Targeting Therapeutics: Molecular Mechanisms of Antisense Oligonucleotides as a Therapeutic Platform," Annu. Rev. Pharmacol. Toxicol., vol. 50:259-293 (2010) (Exhibit No. 1025 filed in interferences 106008, 106007 on Nov. 18, 2014).
Berge, Stephen M. et al., "Pharmaceutical Salts," Journal of Pharmaceutical Sciences, vol. 66(1):1-18 (1977).
Bestas et al., "Design and Application of Bispecific Splice Switching Oligonucleotides," Nuc. Acid Therap., vol. 24, No. 1, pp. 13-24 (2014), Exhibit No. 1120 filed in interferences 106,007 and 106,008 on Feb. 17, 2015.
Braasch, Dwaine A. et al., "Locked nucleic acid (LNA): fine-tuning the recognition of DNA and RNA," Chemistry & Biology, vol. 8:1-7 (2001) (Exhibit No. 2009 filed in interferences 106008, 106013, 106007 on Nov. 18, 2014).
Braasch, Dwaine A. et al., "Novel Antisense and Peptide Nucleic Acid Strategies for Controlling Gene Expression," Biochemistry, vol. 41(14):4503-4510 (2002) (Exhibit No. 2006 filed in interferences 106008, 106013, 106007 on Nov. 18, 2014).
Bremmer-Bout, Mattie et al., "Targeted Exon Skipping in Transgenic hDMD Mice: A Model for Direct Preclinical Screening of Human-Specific Antisense Oligonucleotides," Molecular Therapy, vol. 10(2):232-240 (2004) (Exhibit No. 2024 filed in interferences 106008, 106013, 106007 on Nov. 18, 2014).
Brooke MH, et al., "Clinical investigation in Duchenne dystrophy: 2. Determination of the "power" of therapeutic trials based on the natural history," Muscle Nerve. 1983;6:91-103.
Brown, Susan C. et al., "Dystrophic phenotype induced in vitro by antibody blockade of muscle alpha-dystroglycan-laminin interaction," Journal of Cell Science, vol. 112:209-216 (1999).
Bushby K, et al. "Diagnosis and management of Duchenne muscular dystrophy, part 1: diagnosis, and pharmacological and psychosocial management," Lancet Neural 2010;9:77-93.
Bushby KM, et al., "The clinical, genetic and dystrophin characteristics of Becker muscular dystrophy," II. Correlation of phenotype with genetic and protein abnormalities. J Neural 1993;240: 105-112.
Bushby KM, et al., "The clinical, genetic and dystrophin characteristics of Becker muscular dystrophy," I. Natural history. J Neurol 1993;240:98-104.
Canonic°, A.E. et al., "Expression of a CMV Promoter Drive Human alpha-1 Antitrypsin Gene in Cultured Lung Endothelial Cells and in the Lungs of Rabbits," Clinical Research, vol. 39(2):219A (1991).
Cirak, Sebahattin et al., "Exon skipping and dystrophin restoration in patients with Duchenne muscular dystrophy after systemic phosphorodiamidate morpholino oligomer treatment: an open-label, phase 2, dose-escalation study," Lancet, vol. 378(9791):595-605 (2011).
Claim Chart U.S. Appl. No. 11/233,495, pp. 57, Exhibit No. 1216 filed in Interferences 106,007 and 106,008 on Feb. 17, 2015.
Claim Chart U.S. Appl. No. 13/550,210, pp. 45, Exhibit No. 1217 filed in Interferences 106,007 and 106,008 on Feb. 17, 2015.
Claim Chart, U.S. Pat. No. 7,807,816, 14 pages (Exhibit No. 1063 filed in interferences 106008, 106007 on Nov. 18, 2014).
Claim Chart, U.S. Pat. No. 7,960,541, 17 pages (Exhibit No. 1064 filed in interferences 106008, 106007 on Nov. 18, 2014).
Claim Chart, U.S. Pat. No. 8,455,636, 32 pages (Exhibit No. 1062 filed in interferences 106008, 106007 on Nov. 18, 2014).
Claim Comparison Chart—Claims 11 and 29 in U.S. Appl. No. 13/550,210, pp. 1, Exhibit No. 1226 filed in Interferences 106,007 and 106,008 on Feb. 17, 2015.

(56) References Cited

OTHER PUBLICATIONS

*Claim Comparison Chart U.S. Appl. No. 13/550,210 vs U.S. Appl. No. 11/233,495*, pp. 12, Exhibit No. 1218 filed in Interferences 106,007 and 106,008 on Feb. 17, 2015.
*Claim Comparison Chart U.S. Appl. No. 13/550,210 vs U.S. Appl. No. 12/198,007*, pp. 1, Exhibit No. 1219 filed in Interferences 106,007 and 106,008 on Feb. 17, 2015.
Transcript of 2nd Deposition of Erik J. Sontheimer, Ph.D., dated Mar. 12, 2015, (Academisch Ziekenhuis Leiden Exhibit 1231, filed Apr. 3, 2015 in Interference 106007 and 106008, pp. 1-185).
Transcript of 2nd Deposition of Matthew J.A. Wood, M.D., D. Phil, dated Mar. 5, 2015, (Academisch Ziekenhuis Leiden Exhibit 1230, filed Apr. 3, 2015 in Interference 106007 and 106008, pp. 1-117).
Transcript of Dec. 12, 2014 Teleconference with Administrative Patent Judge Schafer (rough draft) (previously filed in Int. No. 106,008 as Ex. 2114), pp. 28 Exhibit No. 1001 filed in Interference 106,013 on Feb. 17, 2015.
Transcript of the Jan. 21, 2015 deposition of Erik Sontheimer, Ph.D., Patent Interference Nos. 106,007 and 106,008, 98 pages, dated Jan. 21, 2015 (Exhibit No. 2122 filed in interferences 106,007 and 106,008 on Feb. 17, 2015.
Transcript of the Mar. 11, 2015 deposition of Judith van Deutekom, Ph.D., (University of Western Australia Exhibit 2141, filed Apr. 3, 2015 in Interferences 106007, 106008, and 106013, pp. 1-168).
Transcript of the Mar. 12, 2015 deposition of Erik J. Sontheimer, Ph.D., (University of Western Australia Exhibit 2142, filed Apr. 3, 2015 in Interferences 106007, 106008, and 106013, pp. 1-183).
Transcript of the Mar. 5, 2015 deposition of Matthew J. A. Wood, M.D., D. Phil., (University of Western Australia Exhibit 2146, filed Apr. 3, 2015 in Interferences 106007, 106008, and 106013, pp. 1-115).
Transfection of AON, pp. 1, Exhibit No. 1170 filed in Interferences 106,007 and 106,008 on Feb. 16, 2015.
U.S. Food and Drug Administration Presentation at Peripheral and Central Nervous System Drugs Advisory Committee, Apr. 25, 2016, 178 pages.
U.S. Food and Drug Administration Statement, dated Dec. 30, 2014 (2 pages), Exhibit No. 1204 filed in Interferences 106,007 and 106,008 on Feb. 17, 2015.
U.S. Appl. No. 12/198,007, filed Aug. 25, 2008 ("The '007 Application") (Exhibit No. 1073 filed in interferences 106008, 106007 on Dec. 23, 2014).
U.S. Appl. No. 12/976,381, filed Dec. 22, 2010 ("the '381 Application") (Exhibit No. 1074 filed in interferences 106008, 106007 on Dec. 23, 2014).
U.S. Patent Application Publication No. 2001/0056077 ("Matsuo") (Exhibit No. 1080 filed in interferences 106008, 106007 on Dec. 23, 2014).
U.S. Patent Application Publication No. 2002/0049173 ("Bennett et al.") (Exhibit No. 1081 filed in interferences 106008, 106007 on Dec. 23, 2014).
U.S. Pat. No. 5,190,931 ("the '931 Patent") (Exhibit No. 1069 filed in interferences 106008, 106007 on Dec. 23, 2014).
U.S. Pat. No. 7,001,761 (the "Xiao" Patent) (Exhibit No. 1070 filed in interferences 106008, 106007 on Dec. 23, 2014).
University of Western Australia Objections to Opposition Evidence, served on Feb. 24, 2015 filed in Interference No. 106,007, Exhibit 2150, filed Apr. 10, 2015 in Interference Nos. 106007 and 106008, pp. 1-15.
University of Western Australia Objections to Opposition Evidence, served on Feb. 24, 2015, filed in Interference No. 106,008, Exhibit 2151, filed Apr. 10, 2015, in Interference Nos. 106007and 106008, pp. 1-15.
*University of Western Australia v. Academisch Ziekenhuis Leiden*, Decision—Motions—37 C.F.R. § 41.125(a), filed in Patent Interference No. 106008, Sep. 20, 2016, pp. 1-20 (Doc 480).
*University of Western Australia v. Academisch Ziekenhuis Leiden*, Decision—Motions—37 CFR § 41.125(a) (Substitute), filed in Patent Interference No. 106007, May 12, 2016, pp. 1-53 (Doc 476).

*University of Western Australia v. Academisch Ziekenhuis Leiden*, Judgment—Motions—37 C.F.R. § 41.127 filed in Patent Interference No. 106008, Sep. 20, 2016, pp. 1-3 (Doc 481).
*University of Western Australia v. Academisch Ziekenhuis Leiden*, Judgment—Motions—37 CFR § 41.127, filed in Patent Interference No. 106007, Apr. 29, 2016, pp. 1-3 (Doc 474).
European Response, Application No. 13160338.3, 4 pages, dated Jun. 26, 2014 (Exhibit No. 2085 filed in interferences 106008, 106013, 106007 on Nov. 18, 2014).
*University of Western Australia v. Academisch Ziekenhuis Leiden*, Redeclaration—37 CFR 41.203(c), filed in Patent Interference No. 106007, Apr. 29, 2016, pp. 1-2 (Doc 473).
*University of Western Australia v. Academisch Ziekenhuis Leiden*, Withdrawal and Reissue of Decision on Motions, filed in Patent Interference No. 106007, May 12, 2016, pp. 1-2 (Doc 475).
*University of Western Australia v. Academisch Ziekenhuis Leiden*, Academisch Ziekenhuis Leiden List of Exhibits (as of Apr. 3, 2015), filed in Patent Interference No. 106,007, Apr. 3, 2015, pp. 1-18, (Doc 423).
*University of Western Australia v. Academisch Ziekenhuis Leiden*, Academisch Ziekenhuis Leiden List of Exhibits (as of Apr. 3, 2015), filed in Patent Interference No. 106,008, Apr. 3, 2015, pp. 1-18 (Doc 435).
*University of Western Australia v. Academisch Ziekenhuis Leiden*, Academisch Ziekenhuis Leiden List of Exhibits, 18 pages, Patent Interference No. 106,007, (Doc 391), dated Feb. 17, 2015.
*University of Western Australia v. Academisch Ziekenhuis Leiden*, Academisch Ziekenhuis Leiden List of Exhibits, 18 pages, Patent Interference No. 106,008, (Doc 398), dated Feb. 17, 2015.
*University of Western Australia v. Academisch Ziekenhuis Leiden*, Academisch Ziekenhuis Leiden List of Exhibits, 3 pages, Patent Interference No. 106,013, (Doc 147), dated Feb. 17, 2015.
*University of Western Australia v. Academisch Ziekenhuis Leiden*, Academisch Ziekenhuis Leiden Notice of Service of Supplemental Evidence, 3 pages, Patent Interference No. 106,007 (Doc 414), dated Mar. 9, 2015.
*University of Western Australia v. Academisch Ziekenhuis Leiden*, Academisch Ziekenhuis Leiden Notice of Service of Supplemental Evidence, 3 pages, Patent Interference No. 106,008 (Doc 422), dated Mar. 9, 2015.
*University of Western Australia v. Academisch Ziekenhuis Leiden*, Academisch Ziekenhuis Leiden Opposition 1 (35 U.S.C. § 112(a)), 83 pages, Patent Interference No. 106,008, (Doc 400), dated Feb. 17, 2015.
*University of Western Australia v. Academisch Ziekenhuis Leiden*, Academisch Ziekenhuis Leiden Opposition 1 (35 U.S.C. § 112(a)), 93 pages, Patent Interference No. 106,007, (Doc 392), dated Feb. 17, 2015.
*University of Western Australia v. Academisch Ziekenhuis Leiden*, Academisch Ziekenhuis Leiden Opposition 1 (Standing Order ¶ 203.1 and 37 C.F.R. § 41.202(a) and (e)), 20 pages, Patent Interference No. 106,013, (Doc 148), dated Feb. 17, 2015.
*University of Western Australia v. Academisch Ziekenhuis Leiden*, Academisch Ziekenhuis Leiden Opposition 2 (Indefiniteness), 31 pages, Patent Interference No. 106,007, (Doc 396), dated Feb. 17, 2015.
*University of Western Australia v. Academisch Ziekenhuis Leiden*, Academisch Ziekenhuis Leiden Opposition 2 (Indefiniteness), 32 pages, Patent Interference No. 106,008, (Doc 401), dated Feb. 17, 2015.
*University of Western Australia v. Academisch Ziekenhuis Leiden*, Academisch Ziekenhuis Leiden Opposition 3 (35 U.S.C. §135(b)), 44 pages, Patent Interference No. 106,008, (Doc 397), dated Feb. 17, 2015.
*University of Western Australia v. Academisch Ziekenhuis Leiden*, Academisch Ziekenhuis Leiden Opposition 3 (Standing Order § 203.1 and 37 C.F.R. § 41.202(a) and (e)), 20 pages, Patent Interference No. 106,007, (Doc 389), dated Feb. 17, 2015.
*University of Western Australia v. Academisch Ziekenhuis Leiden*, Academisch Ziekenhuis Leiden Reply 1 (For Judgment that UWA'a Claims are Unpatentable Under 35 U.S.C. §§ 102 and 103), dated Apr. 3, 2015, filed in Patent Interference No. 106008, pp. 1-17 (Doc 431).

(56) References Cited

OTHER PUBLICATIONS

*University of Western Australia* v. *Academisch Ziekenhuis Leiden,* Academisch Ziekenhuis Leiden Reply 1 (For Judgment that Uwa's Claims are Unpatentable Under 35 U.S.C. §§ 102 and 103), dated Apr. 3, 2015, filed in Patent Interference No. 106007, pp. 1-17 (Doc 424).
*University of Western Australia* v. *Academisch Ziekenhuis Leiden,* Academisch Ziekenhuis Leiden Reply 2 (To Deny the Benefit of AU 2004903474), dated Apr. 3, 2015, filed in Patent Interference No. 106007, pp. 1-11(Doc 425).
*University of Western Australia* v. *Academisch Ziekenhuis Leiden,* Academisch Ziekenhuis Leiden Reply 2 (To Deny the Benefit of AU 2004903474), dated Apr. 3, 2015, filed in Patent Interference No. 106008, pp. 1-12 (Doc 432).
*University of Western Australia* v. *Academisch Ziekenhuis Leiden,* Academisch Ziekenhuis Leiden Reply 3 (For Judgment of Unpatentability based on Myriad) dated Apr. 3, 2015, filed in Patent Interference No. 106007, pp. 1-12 (Doc 426).
*University of Western Australia* v. *Academisch Ziekenhuis Leiden,* Academisch Ziekenhuis Leiden Reply 3 (For Judgment of Unpatentability based on Myriad) dated Apr. 3, 2015, filed in Patent Interference No. 106008, pp. 1-13 (Doc 433).
*University of Western Australia* v. *Academisch Ziekenhuis Leiden,* Academisch Ziekenhuis Leiden Reply 4 (In Support of Responsive Motion 4 to Add Two New Claims) dated Apr. 3, 2015, filed in Patent Interference No. 106007, pp. 1-17 (Doc 427).
*University of Western Australia* v. *Academisch Ziekenhuis Leiden,* Academisch Ziekenhuis Leiden Reply 4 (In Support of Responsive Motion 4 to Add Two New Claims) dated Apr. 3, 2015, filed in Patent Interference No. 106008 pp. 1-17 (Doc 434).
*University of Western Australia* v. *Academisch Ziekenhuis Leiden,* Academisch Ziekenhuis Leiden Request for Oral Argument, filed in Patent Interference No. 106,007, Apr. 10, 2015, pp. 1-3 (Doc 454).
*University of Western Australia* v. *Academisch Ziekenhuis Leiden,* Academisch Ziekenhuis Leiden Request for Oral Argument, filed in Patent Interference No. 106,008, Apr. 10, 2015, pp. 1-3 (Doc 462).
*University of Western Australia* v. *Academisch Ziekenhuis Leiden,* Academisch Ziekenhuis Leiden Responsive Motion I (To Add Two New Claims), 57 pages, Patent Interference No. 106,008, (Doc 245), dated Dec. 23, 2014.
U.S. Amendment After Non-Final Action for U.S. Appl. No. 11/233,495, 31 pages, dated Jun. 24, 2010 (Exhibit No. 2073 filed in interferences 106008, 106013, 106007 on Nov. 18, 2014).
U.S. Amendment for U.S. Appl. No. 11/233,495, 15 pages, dated Apr. 1, 2009 (Exhibit No. 2071 filed in interferences 106008, 106013, 106007 on Nov. 18, 2014).
U.S. Amendment for U.S. Appl. No. 11/233,495, 19 pages, dated Oct. 31, 2007 (Exhibit No. 2070 filed in interferences 106008, 106013, 106007 on Nov. 18, 2014).
U.S. Amendment for U.S. Appl. No. 11/233,495, 19 pages, dated Sep. 16, 2009 (Exhibit No. 2072 filed in interferences 106008, 106013, 106007 on Nov. 18, 2014).
U.S. Amendment for U.S. Appl. No. 11/233,495, 9 pages, dated Oct. 31, 2007 (Exhibit No. 2070 filed in interferences 106008, 106013, 106007 on Nov. 18, 2014).
U.S. Amendment for U.S. Appl. No. 11/570,691, 9 pages, dated Jun. 15, 2010 (Exhibit No. 1043 filed in interferences 106008, 106007 on Nov. 18, 2014).
U.S. Amendment for U.S. Appl. No. 13/271,080, 30 pages, dated Jan. 30, 2013 (Exhibit No. 1049 filed in interferences 106008, 106007 on Nov. 18, 2014).
U.S. Amendment for U.S. Appl. No. 13/902,376, 36 pages, dated Mar. 21, 2014 (Exhibit No. 1046 filed in interferences 106008, 106007 on Nov. 18, 2014).
U.S. Amendment in Response to Advisory Action for U.S. Appl. No. 11/233,495, 23 pages, dated Mar. 14, 2011 (Exhibit No. 2074 filed in interferences 106008, 106013, 106007 on Nov. 18, 2014).
U.S. Amendments to the Claims for U.S. Appl. No. 11/233,495, 4 pages, dated May 8, 2014 (Exhibit No. 2077 filed in interferences 106008, 106013, 106007 on Nov. 18, 2014).
U.S. Amendments to the Claims for U.S. Appl. No. 14/198,992, 3 pages, dated Jul. 16, 2014 (Exhibit No. 2079 filed in interferences 106008, 106013, 106007 on Nov. 18, 2014).
U.S. Applicant-Initiated Interview Summary and Notice of Allowance for U.S. Appl. No. 13/550,210, 9 pages dated May 9, 2014 (Exhibit No. 2076 filed in interferences 106008, 106013, 106007 on Nov. 18, 2014).
US application as-filed and Preliminary Amendment for U.S. Appl. No. 13/550,210, 59 pages dated Jul. 16, 2012 (Exhibit No. 2087 filed in interferences 106008, 106013, 106007 on Nov. 18, 2014).
US Application as-filed for U.S. Appl. No. 14/198,992, 52 pages, dated Mar. 6, 2014 (Exhibit No. 2086 filed in interferences 106008, 106013, 106007 on Nov. 18, 2014).
US Application as-filed, Application Data Sheet, and Preliminary Amendment for U.S. Appl. No. 12/837,359, 101 pages, dated Jul. 15, 2010 (Exhibit No. 2100 filed in interferences 106008, 106013, 106007 on Nov. 18, 2014).
US Application for Letters Patent for U.S. Appl. No. 11/233,495 as-filed and preliminary amendment, 77 pages, dated Sep. 21, 2005 (Exhibit No. 2095 filed in interferences 106008, 106013, 106007 on Nov. 18, 2014).
U.S. Appl. No. 11/233,495, 74 pages; excerpts of prosecution history for including: US Supplemental Amendment and Response dated May 8, 2014; Second Supplemental Response dated Jul. 5, 2013; Supplemental Amendment dated Jun. 26, 2013; Amendment after Non-final Action dated Nov. 1, 2010; Amendment under 35 USC 1.114 dated Sep. 16, 2009 (Exhibit No. 2054 filed in interferences 106008, 106013, 106007 on Nov. 18, 2014).
U.S. Appl. No. 14/198,992, 17 pages; excerpts of prosecution history including: Supplemental Amendment dated Jul. 16, 2014; Response to Non-Final Office Action dated Jul. 14, 2014 (Exhibit No. 2056 filed in interferences 106008, 106013, 106007 on Nov. 18, 2014).
U.S. Appl. No. 14/248,279, 29 pages; excerpts of prosecution history including: Amendment under 37 CFR 1.312 dated Sep. 19, 2014; Amendment in Response to Final Office Action dated Aug. 7, 2014; Declaration under 37 CFR 1.132 dated May 26, 2014; Declaration under 37 CFR 1.132 dated May 27, 2014; Response dated Jun. 3, 2014 (Exhibit No. 2057 filed in interferences 106008, 106013, 106007 on Nov. 18, 2014).
U.S. Appl. No. 13/550,210, 27 pages; excerpts of prosecution history including: Response and Amendment dated May 12, 2014; Response to Non-Final Office Action dated Jan. 21, 2014; Second Preliminary Amendment dated Jan. 3, 2013 (Exhibit No. 2055 filed in interferences 106008, 106013, 106007 on Nov. 18, 2014).
U.S. claim amendments for U.S. Appl. No. 13/550,210, 3 pages, dated May 12, 2014 (Exhibit No. 2078 filed in interferences 106008, 106013, 106007 on Nov. 18, 2014).
US Claims for Application No. U.S. Appl. No. 12/976,381, 1 page, dated Dec. 22, 2010 (Exhibit No. 2065 filed in interferences 106008, 106013, 106007 on Nov. 18, 2014).
US Declaration of Richard K. Bestwick, for U.S. Appl. No. 11/570,691, 5 pages, dated Jun. 15, 2010 (Exhibit No. 1044 filed in interferences 106008, 106007 on Nov. 18, 2014).
US E-mail from Patent Trial and Appeal Board to Danny Huntington, 2 pages, dated Oct. 9, 2014 (Exhibit No. 2002 filed in interferences 106008 on Oct. 17, 2014).
U.S. Non-Final Office Action for U.S. Appl. No. 11/570,691, 16 pages, dated Mar. 15, 2010 (Exhibit No. 1042 filed in interferences 106008, 106007 on Nov. 18, 2014).
U.S. Office Action for U.S. Appl. No. 13/271,080, 25 pages, dated Jul. 30, 2012 (Exhibit No. 1048 filed in interferences 106008, 106007 on Nov. 18, 2014).
U.S. Office Action for U.S. Appl. No. 13/550,210, 12 pages, dated Sep. 27, 2013 (Exhibit No. 2080 filed in interferences 106008, 106013, 106007 on Nov. 18, 2014).
U.S. Office Action for U.S. Appl. No. 13/902,376, 7 pages, dated Jan. 7, 2014 (Exhibit No. 1045 filed in interferences 106008, 106007 on Nov. 18, 2014).
U.S. Appl. No. 12/198,007 as-filed, 64 pages, dated Aug. 25, 2008 (Exhibit No. 2092 filed in interferences 106008, 106013, and 106007 on Nov. 18, 2014).

(56) References Cited

OTHER PUBLICATIONS

U.S. Preliminary Amendment and application as-filed for U.S. Appl. No. 12/976,381,64 pages, dated Dec. 22, 2010 (Exhibit No. 2089 filed in Interferences 106007, 106008, and 106013 on Nov. 18, 2014).
U.S. Preliminary Amendment for U.S. Appl. No. 11/233,495, 10 pages, dated Sep. 21, 2005 (Exhibit No. 2069 filed in interferences 106008, 106013, 106007 on Nov. 18, 2014).
US Preliminary Remarks for U.S. Appl. No. 14/198,992, 1 page, dated Mar. 6, 2014 (Exhibit No. 2097 filed in interferences 106008, 106013, 106007 on Nov. 18, 2014).
US Proposed Terminal Disclaimer for U.S. Appl. No. 12/860,078, 2 pages, dated Oct. 17, 2014 (Exhibit No. 2001 filed in interference 106008 on Oct. 17, 2014).
US Remarks for U.S. Appl. No. 14/248,279, 2 pages, dated Aug. 27, 2014 (Exhibit No. 2110 filed in interferences 106008, 106013, 106007 on Nov. 18, 2014).
U.S. Response and amendments for U.S. Appl. No. 13/550,210, 12 pages, dated Jan. 21, 2014 (Exhibit No. 2063 filed in interferences 106008, 106013, 106007 on Nov. 18, 2014).
US Revised Figure 4H, U.S. Appl. No. 13/271,080, 1 page (Exhibit No. 1050 filed in interferences 106008, 106007 on Nov. 18, 2014).
US Terminal Disclaimer for U.S. Appl. No. 14/198,992, 1 page, dated Jul. 15, 2014 (Exhibit No. 2096 filed in interferences 106008, 106013, 106007 on Nov. 18, 2014).
US Terminal Disclaimer for U.S. Appl. No. 14/248,279, 1 page, dated Aug. 7, 2014 (Exhibit No. 2109 filed in interferences 106008, 106013, 106007 on Nov. 18, 2014).
US Track One Request, Application as-filed, and Application Data Sheet for U.S. Appl. No. 14/248,279, 68 pages, dated Apr. 8, 2014 (Exhibit No. 2108 filed in interferences 106008, 106013, 106007 on Nov. 18, 2014).
US Transmittal, application as-filed, and Preliminary Amendment for U.S. Appl. No. 11/570,691, 102 pages, dated Dec. 15, 2006 (Exhibit No. 2103 filed in interferences 106008, 106013, 106007 on Nov. 18, 2014).
US Transmittal, application as-filed, and Preliminary Amendment for U.S. Appl. No. 13/270,992, 101 pages, dated Oct. 11, 2011 (Exhibit No. 2098 filed in interferences 106008, 106013, 106007 on Nov. 18, 2014).
US Transmittal, application as-filed, and Preliminary Amendment for U.S. Appl. No. 13/271,080, 115 pages, dated Oct. 11, 2011 (Exhibit No. 2111 filed in interferences 106008, 106013, 106007 on Nov. 18, 2014).
US Updated Filing Receipt for U.S. Appl. No. 13/550,210, 3 pages, dated Dec. 11, 2012 (Exhibit No. 2044 filed in interferences 106008, 106013, 106007 on Nov. 18, 2014).
USPTO "2014 Procedure for Subject Matter Eligibility Analysis of Claims Reciting or Involving . . . Natural Products" ("the March Guidance"), 19 pages, (Exhibit No. 2118 filed in interferences 106,007 and 106,008 on Feb. 17, 2015.
USPTO Written Description Training Materials, Revised Mar. 25, 2008, Example 12 (Exhibit No. 1068 filed in interferences 106008, 106007 on Dec. 23, 2014).
UWA Clean Claims and Sequence, as filed in Interference No. 106,007 on Aug. 1, 2014 (Paper 12), 8 pages, (Exhibit No. 2126 filed in interferences 106,007 and 106,008 on Feb. 17, 2015.
UWA Clean Claims and Sequence, as filed in Interference No. 106,007 on Aug. 7, 2014 (Paper 12), 8 pages, (Exhibit No. 2127 filed in interferences 106,007 and 106,008 on Feb. 17, 2015.
UWA Motion 1 (For Judgment Under 35 § 112(a)) from Int. No. 106,007 (PN 210), pp. 40, Exhibit No. 1005 filed in Interference 106,013 on Feb. 17, 2015.
UWA Motion 1 (For Judgment Under 35 § 112(a)) from Int. No. 106,008 (Doc 213), pp. 38, Exhibit No. 1004 filed in Interference 106,013 on Feb. 17, 2015.
UWA submission of teleconference transcript , 28 pages, dated Dec. 12, 2014 (Exhibit No. 2114 filed in interferences 106008 and 106007 on Dec. 12, 2014).

Valorization Memorandum published by the Dutch Federation of University Medical Centers in Mar. 2009, (University of Western Australia Exhibit 2140, filed Apr. 3, 2015 in Interferences 106007, 106008, and 106013, pp. 1-33).
Van Deutekom et al., "Antisense-induced exon skipping restores dystrophin expression in DMD patient derived muscle cells," Human Molecular Genetics vol. 10, No. 15: 1547-1554 (2001) (Exhibit No. 1084 filed in Interferences 106008, 106007 on Dec. 23, 2014).
Van Deutekom et al., "Local Dystrophin Restoration with Antisense Oligonucleotide PRO051," N. Engl. J. Med., vol. 357, No. 26, pp. 2677-2686 (Dec. 2007), Exhibit No. 1213 filed in Interferences 106,007 and 106,008 on Feb. 17, 2015.
Van Deutekom, Judith C. T. et al., "Advances in Duchenne Muscular Dystrophy Gene Therapy," Nature Reviews Genetics, vol. 4(10):774-783 (2003).
Van Ommen 2002 PCT (WO 02/24906 Al), 43 pages,(Exhibit No. 1071 filed in interferences 106008, 106007 on Dec. 23, 2014).
Van Putten M, et al., The Effects of Low Levels of Dystrophin on Mouse Muscle Function and Pathology. PLoS ONE 2012;7:e31937, 13 pages.
Van Vliet, Laura et al., "Assessment of the Feasibility of Exon 45-55 Multiexon Skipping for Duchenne Muscular Dystrophy", BMC Medical Genetics, vol. 9(1):105 (2008).
Verma, Sandeep et al., "Modified Oligonucleotides: Synthesis and Strategy for Users," Annu. Rev. Biochem., vol. 67:99-134 (1998) (Exhibit No. 1040 filed in interferences 106008, 106007 on Nov. 18, 2014).
*Vikase Corp. v. Am. Nat'l. Can Co.*, No. 93-7651, 1996 WL 377054 (N.D. III. Jul. 1, 1996), 3 pages (Exhibit No. 2152 filed in interference 106013 on Oct. 29, 2015).
Voit, Thomas et al., "Safety and efficacy of drisapersen for the treatment of Duchenne muscular dystrophy (DEMAND II): an exploratory randomised, placebo-controlled phase 2 study," Lancet Neurol., vol. 13:987-996 (2014) (Exhibit No. 2037 filed in interferences 106008, 106013, 106007 on Nov. 18, 2014).
Volloch, Vladimir et al., "Inhibition of Pre-mRNA Splicing by Antisense RNA in Vitro: Effect of RNA Containing Sequences Complementary to Exons," Biochemical and Biophysical Research Communications, vol. 179 (3):1593-1599 (1991).
Wahlestedt et al., "Potent and nontoxic antisense oligonucleotides containing locked nucleic acids," PNAS, vol. 97, No. 10, pp. 5633-5638 (May 2000), Exhibit No. 1201 filed in Interferences 106,007 and 106,008 on Feb. 17, 2015.
Wang et al., "In Vitro evaluation of novel antisense oligonucleotides is predictive of in vivo exon skipping activity for Duchenne muscular dystrophy," J. Gene Medicine, vol. 12, pp. 354-364 (Mar. 2010), Exhibit No. 1115 filed in interferences 106,007 and 106,008 on Feb. 17, 2015.
Wang, Chen-Yen et al., "pH-sensitive immunoliposomes mediate target-cell-specific delivery and controlled expression of a foreign gene in mouse," Proc. Natl. Acad. Sci. USA, vol. 84:7851-7855 (1987).
Watakabe, Akiya et al., "The role of exon sequences in splice site selection," Genes & Development, vol. 7:407-418 (1993).
Watanabe et al., "Plasma Protein Binding of an Antisense Oligonucleotide Targeting Human ICAM-1 (ISIS 2302)," Oligonucleotides, vol. 16, pp. 169-180 (2006), Exhibit No. 1197 filed in Interferences 106,007 and 106,008 on Feb. 17, 2015.
WHO Drug Information, International Nonproprietary Names for Pharmaceutical Substances (INN), Proposed INN: List 115, "Casimersen," vol. 30(2): 3 pages (2016).
WHO Drug Information, International Nonproprietary Names for Pharmaceutical Substances (INN), Proposed INN: List 115, "Golodirsen," vol. 30(2): 3 pages (2016).
Wijnaendts, L.C.D. et al., "Prognostic importance of DNA flow cytometric variables in rhabdomyosarcomas," J. Clin. Pathol., vol. 46:948-952 (1993) (Exhibit No. 1041 filed in interferences 106008, 106007 on Nov. 18, 2014).
Wilton et al. (2007) "Antisense Oligonucleotide-induced Exon Skipping Across the Human Dystrophin Gene Transcript," Molecular Therapy 15(7):1288-1296, 10 pages, (Exhibit No. 2121 filed in interferences 106,007 and 106,008 on Feb. 17, 2015.

(56) References Cited

OTHER PUBLICATIONS

Wilton, Stephen D. et al., "Antisense oligonucleotides in the treatment of Duchenne muscular dystrophy: where are we now?" Neuromuscular Disorders, vol. 15:399-402 (2005).
Wilton, Stephen D. et al., "Specific removal of the nonsense mutation from the mdx dystrophin mRNA using antisense oligonucleotides," Neuromuscular Disorders, vol. 9:330-338 (1999).
WO 2002/24906 A1 of AZL, (University of Western Australia Exhibit 2134, filed Apr. 3, 2015 in Interferences 106007, 106008, and 106013, pp. 1-43).
WO 2004/083432 (the published AZL PCT Application, "Van Ommen"), pp. 71, Exhibit No. 1003 filed in Interference 106,013 on Feb. 17, 2015.
WO 2013/112053 A1, (University of Western Australia Exhibit 2130, filed Apr. 3, 2015 in Interferences 106007, 106008, and 106013, pp. 1-177).
Wolff, Jon A. et al., "Direct Gene Transfer into Mouse Muscle in Vivo," Science, vol. 247(4949 Pt. 1):1465-1468 (1990).
Wong, Marisa L. et al., "Real-time PCR for mRNA quantitation," BioTechniques, vol. 39:75-85 (2005) (Exhibit No. 1066 filed in interferences 106008, 106007 on Nov. 18, 2014).
Wood, "Toward an Oligonucleotide Therapy for Duchenne Muscular Dystrophy: A Complex Development Challenge," Science Translational Medicine, vol. 2, No. 25, pp. 1-6 (Mar. 2010), Exhibit No. 1116 filed in interferences 106,007 and 106,008 on Feb. 17, 2015,Doc 335.
Written Opinion for Application No. PCT/AU2010/001520, 6 pages, dated Jan. 21, 2011.
Wu, B. et al., "Dose-dependent restoration of dystrophin expression in cardiac muscle of dystrophic mice by systemically delivered morpholino," Gene Therapy, vol. 17:132-140 (2010).
Wu, Bo et al., "Effective rescue of dystrophin improves cardiac function in dystrophin-deficient mice by a modified morpholino oligomer," PNAS, vol. 105(39)14814-14819 (2008).
Wu, Bo et al., "Targeted Skipping of Human Dystrophin Exons in Transgenic Mouse Model Systemically for Antisense Drug Development," PLoS One, vol. 6(5):e19906, 11 pages (2011).
Wu, George Y. et al., "Receptor-mediated Gene Delivery and Expression in Vivo," The Journal of Biological chemistry, vol. 263(29):14621-14624 (1988).
Wu, George Y. et al., "Receptor-mediated in Vitro Gene Transformation by a Soluble DNA Carrier System," The Journal of Biological Chemistry, vol. 262(10):4429-4432 (1987).
Wyatt et al. "Site-specific cross-linking of mammalian U5 snRNP to the 5' splice site before the first step of pre-mRNA splicing," Genes & Development, vol. 6, pp. 2542-2553 (1992), Exhibit No. 1198 filed in Interferences 106,007 and 106,008 on Feb. 17, 2015.
Yin et al., "A fusion peptide directs enhanced systemic dystrophin exon skipping and functional restoration in Dystrophin-deficient mdx mice," Human Mol. Gen., vol. 18, No. 22, pp. 4405-4414 (2009), Exhibit No. 1200 filed in Interferences 106,007 and 106,008 on Feb. 17, 2015.
Yin et al., "Cell Penetrating peptide-conjugated antisense cardiac dystrophin expression and function," Human Mol. Gen., vol. 17, No. 24, pp. 3909-3918 (2008), Exhibit No. 1199 filed in Interferences 106,007 and 106,008 on Feb. 17, 2015.
Yin et al., "Functional Rescue of Dystrophin-deficient mdx Mice by a ChimericPeptide-PMO," Mol. Therapy, vol. 18, No. 10, pp. 1822-1829 (Oct. 2010), Exhibit No. 1117 filed in interferences 106,007 and 106,008 on Feb. 17, 2015.
Yokota et al., "Efficacy of Systematic Morpholino Exon-Skipping in Duchenne Dystrophy Dogs," American Neurological Assoc., vol. 65, No. 6, pp. 667-676 (Jun. 2009), Exhibit No. 1214 filed in Interferences 106,007 and 106,008 on Feb. 17, 2015.
*Zoltek Corp. v. U.S.*, 95 Fed. Cl. 681 (2011), 23 pages, (Academisch Ziekenhuis Leiden Exhibit 1236, filed May 5, 2015 in Interference 106007 and 106008).
European Search Report for Application No. 12162995.0, 11 pages, dated Jan. 15, 2013.
Harel-Bellan, Annick et al., "Specific Inhibition of c-myc Protein Biosynthesis Using an Antisense Synthetic Deoxy-Oligonucleotide in Human T Lymphocytes," The Journal of Immunology, vol. 140(7):2431-2435 (1988).
Hudziak, Robert M. et al., "Resistance of Morpholino Phosphorodiamidate Oligomers to Enzymatic Degradation," Antisense & Nucleic Acid Drug Development, vol. 6:267-272 (1996).
*University of Western Australia v. Academisch Ziekenhuis Leiden*, Academisch Ziekenhuis Leiden's List of Exhibits as of May 5, 2015, filed in Patent Interference No. 106,007, May 5, 2015, pp. 1-18 (Doc 466).
*University of Western Australia v. Academisch Ziekenhuis Leiden*, Academisch Ziekenhuis Leiden's List of Exhibits as of May 5, 2015, filed in Patent Interference No. 106,008, May 5, 2015, pp. 1-18 (Doc 474).
*University of Western Australia v. Academisch Ziekenhuis Leiden*, All Exhibit List, 10 pages, Patent Interference No. 106,008, dated Dec. 23, 2014 (Doc 244).
*University of Western Australia v. Academisch Ziekenhuis Leiden*, UWA Motion 3 Requesting an additional Interference between UWA U.S. Patent No. 8,455,636 and AZL U.S. Appl. No. 14/248,279, 36 pages, Patent Interference No. 106,007, dated Nov. 18, 2014 (Doc 212).
*University of Western Australia v. Academisch Ziekenhuis Leiden*, Academisch Ziekenhuis Leiden Responsive Motion 4 (To Add Two New Claims), 65 pages, Patent Interference No. 106,007, (Doc 241), dated Dec. 23, 2014.
*University of Western Australia v. Academisch Ziekenhuis Leiden*, Academisch Ziekenhuis Leiden Statement Regarding Oral Argument, filed in Patent Interference No. 106,013, Apr. 10, 2015, pp. 1-3 (Doc 189).
*University of Western Australia v. Academisch Ziekenhuis Leiden*, Academisch Ziekenhuis Leiden's Opposition 4 (To Not Exclude Evidence), filed in Patent Interference No. 106,007, May 5, 2015, pp. 1-22 (Doc 465).
*University of Western Australia v. Academisch Ziekenhuis Leiden*, Academisch Ziekenhuis Leiden's Opposition 4 (To Not Exclude Evidence), filed in Patent Interference No. 106,008, May 5, 2015, pp. 1-21 (Doc 473).
*University of Western Australia v. Academisch Ziekenhuis Leiden*, Academisch Ziekenhuis Leiden's Second Supplemental Notice of Real Party in Interest, filed in Patent Interference No. 106,007, May 28, 2015, pp. 1-3, (Doc 468).
*University of Western Australia v. Academisch Ziekenhuis Leiden*, Academisch Ziekenhuis Leiden's Second Supplemental Notice of Real Party in Interest, filed in Patent Interference No. 106,008, May 28, 2015, pp. 1-3, (Doc 176).
*University of Western Australia v. Academisch Ziekenhuis Leiden*, Academisch Ziekenhuis Leiden's Second Supplemental Notice of Real Party in Interest, filed in Patent Interference No. 106013, May 28, 2015, pp. 1-3, (Doc 191).
*University of Western Australia v. Academisch Ziekenhuis Leiden*, Academish Ziekenhuis Leiden Supplemental Notice of Real Party in Interest, pp. 3, Doc 149, Patent Interference No. 106,013 dated Feb. 23, 2015.
*University of Western Australiav. Academisch Ziekenhuis Leiden*, Academish Ziekenhuis Leiden Supplemental Notice of Real Party in Interest, pp. 3, Doc 413, Patent Interference No. 106,0007 dated Feb. 23, 2015.
*University of Western Australia v. Academisch Ziekenhuis Leiden*, Academish Ziekenhuis Leiden Supplemental Notice of Real Party in Interest, pp. 3, Doc 421, Patent Interference No. 106,0008 dated Feb. 23, 2015.
*University of Western Australia v. Academisch Ziekenhuis Leiden*, Amendment and Response, U.S. Appl. No. 11/233,495, filed Jan. 22, 2014, 8 pages, (Exhibit No. 2117 filed in interferences 106,007 and 106, 006, on Feb. 17, 2015.
*University of Western Australia v. Academisch Ziekenhuis Leiden*, AZL Annotated Copy of Claims, Patent Interference No. 106,007, 15 pages, dated Aug. 15, 2014 (Doc 15).
*University of Western Australia v. Academisch Ziekenhuis Leiden*, AZL Annotated Copy of Claims, Patent Interference No. 106,008, 14 pages, dated Aug. 21, 2014 (Doc 14).

(56) References Cited

OTHER PUBLICATIONS

*University of Western Australia v. Academisch Ziekenhuis Leiden,* AZL Annotated Copy of Claims, Patent Interference No. 106,013, 14 pages, dated Oct. 27, 2014 (Doc 16).
*University of Western Australia v. Academisch Ziekenhuis Leiden,* AZL Clean Copy of Claims and Sequence, filed in Patent Interference No. 106,013, 5 pages, dated Oct. 15, 2014 (Doc 12).
*University of Western Australia v. Academisch Ziekenhuis Leiden,* AZL Corrected Notice of Related Proceedings, Patent Interference No. 106,007, 3 pages, dated Aug. 1, 2014 (Doc 13).
*University of Western Australia v. Academisch Ziekenhuis Leiden,* AZL Exhibit List, 10 pages, Patent Interference No. 106,007 dated Dec. 23, 2014 (Doc 240).
*University of Western Australia v. Academisch Ziekenhuis Leiden,* AZL List of Exhibits, 9 pages, Patent Interference No. 106,007, dated Nov. 18, 2014 (Doc 209).
*University of Western Australia v. Academisch Ziekenhuis Leiden,* Azl List of Exhibits, as of Nov. 18, 2014, 9 pages, Patent Interference No. 106,008, dated Nov. 18, 2014 (Doc 212).
*University of Western Australia v. Academisch Ziekenhuis Leiden,* AZL List of Proposed Motions, Patent Interference No. 106,007, 6 pages, dated Sep. 10, 2014 (Doc 16).
*University of Western Australia v. Academisch Ziekenhuis Leiden,* AZL List of Proposed Motions, Patent Interference No. 106,008, 8 pages, dated Sep. 10, 2014 (Doc 15).
*University of Western Australia v. Academisch Ziekenhuis Leiden,* AZL Motion 1 (For Judgment that Uwa's Claims are Unpatentable Under 35 U.S.C. sections 102 and 103), 69 pages, Patent Interference No. 106,007, dated Nov. 18, 2014 (Doc 181).
*University of Western Australia v. Academisch Ziekenhuis Leiden,* AZL Motion 1 (For Judgment that UWA's Claims are Unpatentable Under 35 U.S.C. sections 102 and 103), 69 pages, Patent Interference No. 106,008, dated Nov. 18, 2014 (Doc 184).
*University of Western Australia v. Academisch Ziekenhuis Leiden,* AZL Motion 2 (To Deny UWA the Benefit of AU 2004903474), 23 pages, Patent Interference No. 106,007, dated Nov. 18, 2014 (Doc 26).
*University of Western Australia v. Academisch Ziekenhuis Leiden,* AZL Motion 2 (To Deny UWA the Benefit of AU 2004903474), 24 pages, Patent Interference No. 106,008, dated Nov. 18, 2014 (Doc 29).
*University of Western Australia v. Academisch Ziekenhuis Leiden,* AZL Motion 3 (For Judgment of Unpatentability based on Myriad) 20 pages, Patent Interference No. 106,008, dated Nov. 18, 2014 (Doc 30).
*University of Western Australia v. Academisch Ziekenhuis Leiden,* AZL Motion 3 (For Judgment of Unpatentability based on Myriad), 19 pages, Patent Interference No. 106,007, dated Nov. 18, 2014 (Doc 27).
*University of Western Australia v. Academisch Ziekenhuis Leiden,* AZL Notice of Related Proceedings, Patent Interference No. 106,007, 3 pages, dated Jul. 31, 2014 (Doc 6).
*University of Western Australia v. Academisch Ziekenhuis Leiden,* AZL Notice of Related Proceedings, Patent Interference No. 106,008, 3 pages, dated Aug. 5, 2014 (Doc 7).
*University of Western Australiav. Academisch Ziekenhuis Leiden,* AZL Notice of Related Proceedings, Patent Interference No. 106,013, 3 pages, dated Oct. 15, 2014 (Doc 11).
*University of Western Australia v. Academisch Ziekenhuis Leiden,* Clean Claims and Sequences, 5 pages, dated Aug. 5, 2014 (Exhibit No. 2047 filed in interferences 106008, 106013, 106007 on Nov. 18, 2014).
*University of Western Australia v. Academisch Ziekenhuis Leiden,* Clean Claims and Sequences, 5 pages, dated Jul. 31, 2014 (Exhibit No. 2045 filed in interferences 106008, 106013, 106007 on Nov. 18, 2014).
*University of Western Australia v. Academisch Ziekenhuis Leiden,* Clean Claims and Sequences, 5 pages, dated Oct. 15, 2014 (Exhibit No. 2050 filed in interferences 106008, 106013, 106007 on Nov. 18, 2014).
*University of Western Australia v. Academisch Ziekenhuis Leiden,* Decision—Motions—37 CFR § 41.125(a), filed in Patent Interference No. 106007, Apr. 29, 2016, pp. 1-53 (Doc 472).
University of Western Australia v. Academisch Ziekenhuis Leiden, Decision—Motions—37 CFR§ 41.125(a), filed in Patent Interference No. 106,013, Jun. 22, 2015, pp. 1-12 (Doc 192).
*University of Western Australia v. Academisch Ziekenhuis Leiden,* Decision—Priority 37 CFR § 41.125 (a), 18 pages, Patent Interference No. 106,013, (Doc 196), dated Sep. 29, 2015.
*University of Western Australia v. Academisch Ziekenhuis Leiden,* Decision—Rehearing—37 CFR § 41.125(c), filed in Patent Interference No. 106,013, Dec. 29, 2015, pp. 1-12 (Doc 202).
*University of Western Australia v. Academisch Ziekenhuis Leiden,* Declaration of Erik Sontheimer dated Nov. 17, 2014, Exhibit 1012 filed in Patent Interference Nos. 106,007 and 106,008, 112 pages, filed Nov. 18, 2014.
*University of Western Australia v. Academisch Ziekenhuis Leiden,* Declaration of Interference, Patent Interference No. 106,007, 7 pages, dated Jul. 18, 2014 (Doc 1).
University of Western Australia v. Academisch Ziekenhuis Leiden, Declaration of Interference, Patent Interference No. 106,008, 7 pages, dated Jul. 24, 2014 (Doc 1).
*University of Western Australia v. Academisch Ziekenhuis Leiden,* Declaration of Interference, Patent Interference No. 106,013, 8 pages, dated Sep. 29, 2014 (Doc 1).
*University of Western Australia v. Academisch Ziekenhuis Leiden,* Declaration of Matthew J.A. Wood, Patent Interference Nos. 106,007, 106,008 and 106,013, 184 pages, dated Nov. 18, 2014 (Exhibit No. 2081 filed in interferences 106008, 106013, 106007 on Nov. 18, 2014).
*University of Western Australia v. Academisch Ziekenhuis Leiden,* Joint Stipulation regarding Time Periods 2, 3 and 4, 3 pages, Patent Interference No. 106,013, (Doc 135), dated Jan. 25, 2015.
*University of Western Australia v. Academisch Ziekenhuis Leiden,* Joint Stipulation regarding Time Periods 3-4, 4 pages, Patent Interference No. 106,007, (Doc 243), dated Jan. 29, 2015.
*University of Western Australia v. Academisch Ziekenhuis Leiden,* Joint Stipulation regarding Time Periods 3-4, 4 pages, Patent Interference No. 106,008, (Doc 247), dated Jan. 29, 2015.
*University of Western Australia v. Academisch Ziekenhuis Leiden,* Joint Stipulation regarding Time Periods 3-4, 4 pages, Patent Interference No. 106,013, (Doc 137), dated Jan. 29, 2015.
*University of Western Australia v. Academisch Ziekenhuis Leiden,* Joint Stipulation Regarding Time Periods 4-6, 4 pages, Patent Interference No. 106,007, dated Mar. 19, 2015 (Doc 416).
*University of Western Australia v. Academisch Ziekenhuis Leiden,* Joint Stipulation Regarding Time Periods 4-6, 4 pages, Patent Interference No. 106013, (Doc 151), dated Mar. 19, 2015.
*University of Western Australia v. Academisch Ziekenhuis Leiden,* Joint Stipulation Regarding Time Periods 4-6, 4 pages, Patent Interference No. 106,008, (Doc 424), dated Mar. 19, 2015.
*University of Western Australia v. Academisch Ziekenhuis Leiden,* Judgment-37 CFR § 41.127, 2 pages, Patent Interference No. 106,013, (Doc 197), dated Sep. 29, 2015.
European Decision of the Opposition Division, European Application No. 10004274.6, dated Dec. 19, 2017, 23 pages.
Extended European Search Report, EP 16172354.9, dated Jan. 23, 2017, 7 pages.
Extended European Search Report, EP 17159328.8, dated Sep. 5, 2017, 10 pages.
*University of Western Australia v. Academisch Ziekenhuis Leiden,* UWA Notice of Filing Priority Statement, 2 pages, Patent Interference No. 106,007, dated Nov. 18, 2014 (Doc 215).

FIGURE 1

```
bp        Acceptor                    ESE                            Donor
ucaugcacugagugaccucuuucucgcagGCGCUAGCUGGAGCA/////CCGUGCAGACUGACGgucucau
```

SEQ ID NO:213                                        SEQ ID NO:214

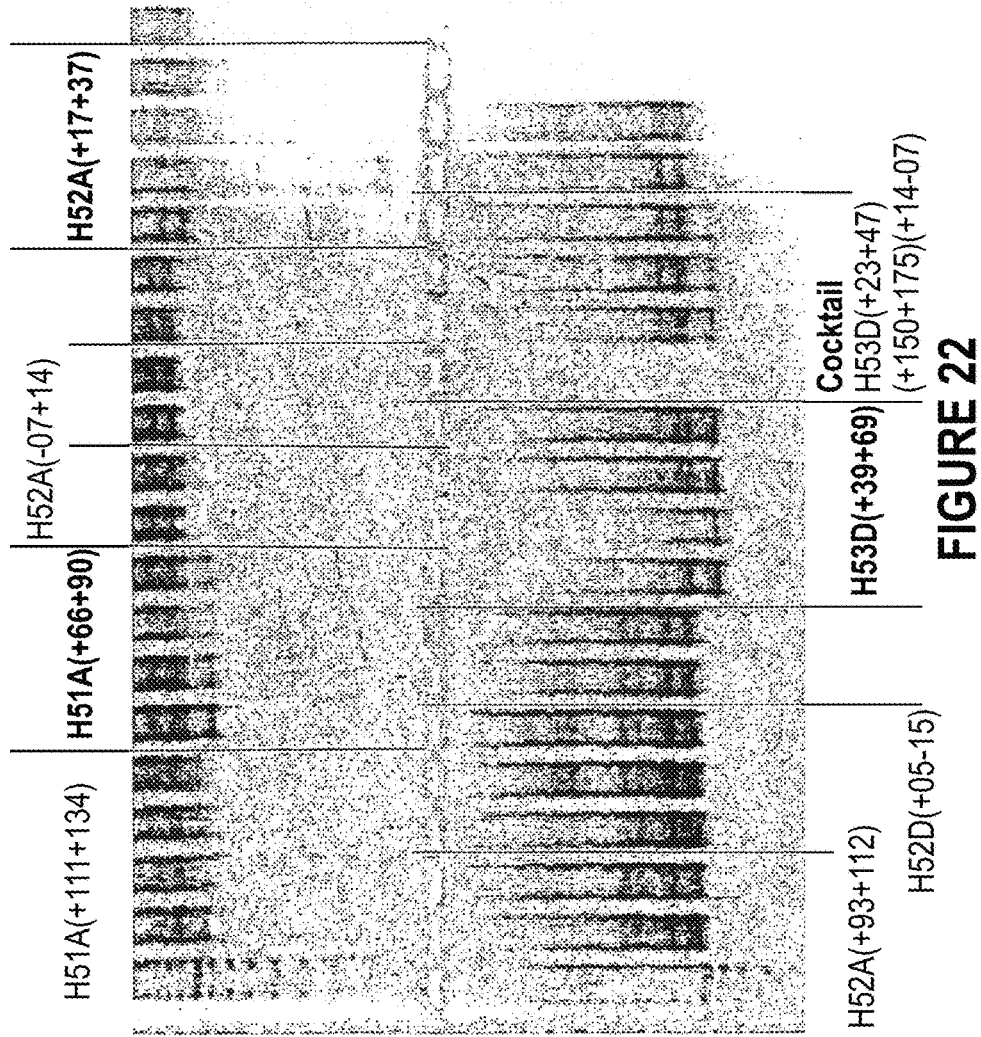

ANTISENSE OLIGONUCLEOTIDES FOR INDUCING EXON SKIPPING AND METHODS OF USE THEREOF

CROSS-REFERENCE TO RELATED APPLICATIONS

This application is a continuation of U.S. patent application Ser. No. 15/274,772, filed Sep. 23, 2016, now pending, which application is a continuation of U.S. patent application Ser. No. 14/740,097, filed Jun. 15, 2015, now issued as U.S. Pat. No. 9,605,262, which application is a continuation of U.S. patent application Ser. No. 13/741,150, filed Jan. 14, 2013, now abandoned, which application is a continuation of U.S. patent application Ser. No. 13/168,857, filed Jun. 24, 2011, now abandoned, which application is a continuation of U.S. patent application Ser. No. 12/837,359, filed Jul. 15, 2010, now issued as U.S. Pat. No. 8,232,384, which application is a continuation of U.S. patent application Ser. No. 11/570,691, filed Jan. 15, 2008, now issued as U.S. Pat. No. 7,807,816, which application is a 35 U.S.C. § 371 National Phase Application of PCT/AU2005/000943, filed Jun. 28, 2005, which claims priority to Australian Patent Application No. 2004903474, filed Jun. 28, 2004; which applications are each incorporated herein by reference in their entireties.

STATEMENT REGARDING SEQUENCE LISTING

The Sequence Listing associated with the application is provided in text format in lieu of a paper copy, and is hereby incorporated by reference into the specification. The name of the text file containing the Sequence Listing is AVN-008CN41_Sequence-Listing.txt. The text file is 62,086 Kilobytes, was created on Sep. 14, 2017 and is being submitted electronically via EFS-Web.

FIELD OF THE INVENTION

The present invention relates to novel antisense compounds and compositions suitable for facilitating exon skipping. It also provides methods for inducing exon skipping using the novel antisense compounds as well as therapeutic compositions adapted for use in the methods of the invention.

BACKGROUND ART

Significant effort is currently being expended researching methods for suppressing or compensating for disease-causing mutations in genes. Antisense technologies are being developed using a range of chemistries to affect gene expression at a variety of different levels (transcription, splicing, stability, translation). Much of that research has focused on the use of antisense compounds to correct or compensate for abnormal or disease-associated genes in a myriad of different conditions.

Antisense molecules are able to inhibit gene expression with exquisite specificity and because of this many research efforts concerning oligonucleotides as modulators of gene expression have focused on inhibiting the expression of targeted genes such as oncogenes or viral genes. The antisense oligonucleotides are directed either against RNA (sense strand) or against DNA where they form triplex structures inhibiting transcription by RNA polymerase II. To achieve a desired effect in specific gene down-regulation, the oligonucleotides must either promote the decay of the targeted mRNA or block translation of that mRNA, thereby effectively preventing de novo synthesis of the undesirable target protein.

Such techniques are not useful where the object is to up-regulate production of the native protein or compensate for mutations which induce premature termination of translation such as nonsense or frame-shifting mutations. Furthermore, in cases where a normally functional protein is prematurely terminated because of mutations therein, a means for restoring some functional protein production through antisense technology has been shown to be possible through intervention during the splicing processes (Sierakowska H, et al., (1996) *Proc Natl Acad Sci USA* 93, 12840-12844; Wilton S D, et al., (1999) *Neuromusc Disorders* 9, 330-338; van Deutekom J C et al., (2001) *Human Mol Genet* 10, 1547-1554). In these cases, the defective gene transcript should not be subjected to targeted degradation so the antisense oligonucleotide chemistry should not promote target mRNA decay.

In a variety of genetic diseases, the effects of mutations on the eventual expression of a gene can be modulated through a process of targeted exon skipping during the splicing process. The splicing process is directed by complex multi-particle machinery that brings adjacent exon-intron junctions in pre-mRNA into close proximity and performs cleavage of phosphodiester bonds at the ends of the introns with their subsequent reformation between exons that are to be spliced together. This complex and highly precise process is mediated by sequence motifs in the pre-mRNA that are relatively short semi-conserved RNA segments to which bind the various nuclear splicing factors that are then involved in the splicing reactions. By changing the way the splicing machinery reads or recognises the motifs involved in pre-mRNA processing, it is possible to create differentially spliced mRNA molecules. It has now been recognised that the majority of human genes are alternatively spliced during normal gene expression, although the mechanisms invoked have not been identified. Using antisense oligonucleotides, it has been shown that errors and deficiencies in a coded mRNA could be bypassed or removed from the mature gene transcripts.

In nature, the extent of genetic deletion or exon skipping in the splicing process is not fully understood, although many instances have been documented to occur, generally at very low levels (Sherrat T G, et al., (1993) *Am J Hum Genet* 53, 1007-1015). However, it is recognised that if exons associated with disease-causing mutations can be specifically deleted from some genes, a shortened protein product can sometimes be produced that has similar biological properties of the native protein or has sufficient biological activity to ameliorate the disease caused by mutations associated with the target exon (Lu Q L, et al., (2003) *Nature Medicine* 9, 1009-1014; Aartsma-Rus A et al., (2004) *Am J Hum Genet* 74: 83-92).

This process of targeted exon skipping is likely to be particularly useful in long genes where there are many exons and introns, where there is redundancy in the genetic constitution of the exons or where a protein is able to function without one or more particular exons (e.g. with the dystrophin gene, which consists of 79 exons; or possibly some collagen genes which encode for repeated blocks of sequence or the huge nebulin or titin genes which are comprised of ~80 and over 370 exons, respectively).

Efforts to redirect gene processing for the treatment of genetic diseases associated with truncations caused by mutations in various genes have focused on the use of antisense oligonucleotides that either: (1) fully or partially overlap with the elements involved in the splicing process; or (2) bind to the pre-mRNA at a position sufficiently close to the element to disrupt the binding and function of the splicing factors that would normally mediate a particular splicing reaction which occurs at that element (e.g., binds to the pre-mRNA at a position within 3, 6, or 9 nucleotides of the element to be blocked).

For example, modulation of mutant dystrophin pre-mRNA splicing with antisense oligoribonucleotides has been reported both in vitro and in vivo. In one type of dystrophin mutation reported in Japan, a 52-base pair deletion mutation causes exon 19 to be removed with the flanking introns during the splicing process (Matsuo et al., (1991) *J Clin Invest.*, 87:2127-2131). An in vitro minigene splicing system has been used to show that a 31-mer 2'-O-methyl oligoribonucleotide complementary to the 5' half of the deleted sequence in dystrophin Kobe exon 19 inhibited splicing of wild-type pre-mRNA (Takeshima et al. (1995), *J. Clin. Invest.*, 95, 515-520). The same oligonucleotide was used to induce exon skipping from the native dystrophin gene transcript in human cultured lymphoblastoid cells.

Dunckley et al., (1997) *Nucleosides & Nucleotides*, 16, 1665-1668 described in vitro constructs for analysis of splicing around exon 23 of mutated dystrophin in the mdx mouse mutant, a model for muscular dystrophy. Plans to analyse these constructs in vitro using 2' modified oligonucleotides targeted to splice sites within and adjacent to mouse dystrophin exon 23 were discussed, though no target sites or sequences were given.

2'-O-methyl oligoribonucleotides were subsequently reported to correct dystrophin deficiency in myoblasts from the mdx mouse from this group. An antisense oligonucleotide targeted to the 3' splice site of murine dystrophin intron 22 was reported to cause skipping of the mutant exon as well as several flanking exons and created a novel in-frame dystrophin transcript with a novel internal deletion. This mutated dystrophin was expressed in 1-2% of antisense treated mdx myotubes. Use of other oligonucleotide modifications such as 2'-O-methoxyethyl phosphodiesters are described (Dunckley et al. (1998) *Human Mol. Genetics*, 5, 1083-90).

Thus, antisense molecules may provide a tool in the treatment of genetic disorders such as Duchenne Muscular Dystrophy (DMD). However, attempts to induce exon skipping using antisense molecules have had mixed success. Studies on dystrophin exon 19, where successful skipping of that exon from the dystrophin pre-mRNA was achieved using a variety of antisense molecules directed at the flanking splice sites or motifs within the exon involved in exon definition as described by Errington et al. (2003) *J Gen Med* 5, 518-527".

In contrast to the apparent ease of exon 19 skipping, the first report of exon 23 skipping in the mdx mouse by Dunckley et al., (1998) is now considered to be reporting only a naturally occurring revertant transcript or artefact rather than any true antisense activity. In addition to not consistently generating transcripts missing exon 23, Dunckley et al., (1998) did not show any time course of induced exon skipping, or even titration of antisense oligonucleotides, to demonstrate dose dependent effects where the levels of exon skipping corresponded with increasing or decreasing amounts of antisense oligonucleotide. Furthermore, this work could not be replicated by other researchers.

The first example of specific and reproducible exon skipping in the mdx mouse model was reported by Wilton et al., (1999) *Neuromuscular Disorders* 9, 330-338. By directing an antisense molecule to the donor splice site, consistent and efficient exon 23 skipping was induced in the dystrophin mRNA within 6 hours of treatment of the cultured cells. Wilton et al, (1999), also describe targeting the acceptor region of the mouse dystrophin pre-mRNA with longer antisense oligonucleotides and being unable to repeat the published results of Dunckley et al., (1998). No exon skipping, either 23 alone or multiple removal of several flanking exons, could be reproducibly detected using a selection of antisense oligonucleotides directed at the acceptor splice site of intron 22.

While the first antisense oligonucleotide directed at the intron 23 donor splice site induced consistent exon skipping in primary cultured myoblasts, this compound was found to be much less efficient in immortalized cell cultures expressing higher levels of dystrophin. However, with refined targeting and antisense oligonucleotide design, the efficiency of specific exon removal was increased by almost an order of magnitude (see Mann C J et al., (2002) *J Gen Med* 4, 644-654).

Thus, there remains a need to provide antisense oligonucleotides capable of binding to and modifying the splicing of a target nucleotide sequence. Simply directing the antisense oligonucleotides to motifs presumed to be crucial for splicing is no guarantee of the efficacy of that compound in a therapeutic setting.

SUMMARY OF THE INVENTION

The present invention provides antisense molecule compounds and compositions suitable for binding to RNA motifs involved in the splicing of pre-mRNA that are able to induce specific and efficient exon skipping and a method for their use thereof.

The choice of target selection plays a crucial role in the efficiency of exon skipping and hence its subsequent application of a potential therapy. Simply designing antisense molecules to target regions of pre-mRNA presumed to be involved in splicing is no guarantee of inducing efficient and specific exon skipping. The most obvious or readily defined targets for splicing intervention are the donor and acceptor splice sites although there are less defined or conserved motifs including exonic splicing enhancers, silencing elements and branch points.

The acceptor and donor splice sites have consensus sequences of about 16 and 8 bases respectively (see FIG. 1 for schematic representation of motifs and domains involved in exon recognition, intron removal and the splicing process).

According to a first aspect, the invention provides antisense molecules capable of binding to a selected target to induce exon skipping.

For example, to induce exon skipping in exons 3 to 8, 10 to 16, 19 to 40, 42 to 44, 46, 47, and 50 to 53 in the Dystrophin gene transcript the antisense molecules are preferably selected from the group listed in Table 1A.

In a further example, it is possible to combine two or more antisense oligonucleotides of the present invention together to induce multiple exon skipping in exons 19-20, and 53. This is a similar concept to targeting of a single exon. A combination or "cocktail" of antisense oligonucleotides are directed at adjacent exons to induce efficient exon skipping.

In another example, to induce exon skipping in exons 19-20, 31, 34 and 53 it is possible to improve exon skipping of a single exon by joining together two or more antisense oligonucleotide molecules. This concept is termed by the inventor as a "weasel", an example of a cunningly designed antisense oligonucleotide. A similar concept has been described in Aartsma-Rus A et al., (2004) *Am J Hum Genet* 74: 83-92).

According to a second aspect, the present invention provides antisense molecules selected and or adapted to aid in the prophylactic or therapeutic treatment of a genetic disorder comprising at least an antisense molecule in a form suitable for delivery to a patient.

According to a third aspect, the invention provides a method for treating a patient suffering from a genetic disease wherein there is a mutation in a gene encoding a particular protein and the affect of the mutation can be abrogated by exon skipping, comprising the steps of: (a) selecting an antisense molecule in accordance with the methods described herein; and (b) administering the molecule to a patient in need of such treatment.

The invention also addresses the use of purified and isolated antisense oligonucleotides of the invention, for the manufacture of a medicament for treatment of a genetic disease.

The invention further provides a method of treating a condition characterised by Duchenne muscular dystrophy, which method comprises administering to a patient in need of treatment an effective amount of an appropriately designed antisense oligonucleotide of the invention, relevant to the particular genetic lesion in that patient. Further, the invention provides a method for prophylactically treating a patient to prevent or at least minimise Duchene muscular dystrophy, comprising the step of: administering to the patient an effective amount of an antisense oligonucleotide or a pharmaceutical composition comprising one or more of these biological molecules.

The invention also provides kits for treating a genetic disease, which kits comprise at least a antisense oligonucleotide of the present invention, packaged in a suitable container and instructions for its use.

Other aspects and advantages of the invention will become apparent to those skilled in the art from a review of the ensuing description, which proceeds with reference to the following figures.

BRIEF DESCRIPTION OF THE DRAWINGS

FIG. 1 Schematic representation of motifs and domains involved in exon recognition, intron removal and the splicing process (SEQ ID NOS: 213 and 214).

FIG. 22 Gel electrophoresis showing exon 51, exon 52 and exon 53 skipping using various antisense molecules directed at exons 51, 52 and 53, respectively. A "cocktail" of antisense molecules is also shown directed at exon 53.

BRIEF DESCRIPTION OF THE SEQUENCE LISTINGS

TABLE 1A

Figure 2:
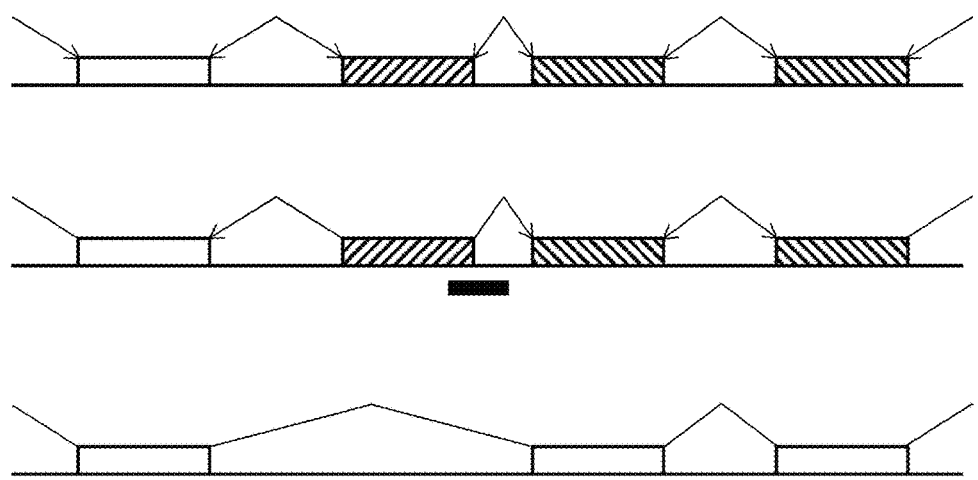
FIG. 2 Diagrammatic representation of the concept of antisense oligonucleotide induced exon skipping to by-pass disease-causing mutations (not drawn to scale). The hatched box represents an exon carrying a mutation that prevents the translation of the rest of the mRNA into a protein. The solid black bar represents an antisense oligonucleotide that prevents inclusion of that exon in the mature mRNA.

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA- like, U represents uracil. With other antisense chemistries such as peptide nucleic acids or morpholinos, these U bases may be shown as "T".

| SEQ ID | SEQUENCE | NUCLEOTIDE SEQUENCE (5'-3') |
|---|---|---|
| 1 | H8A(-06+18) | GAU AGG UGG UAU CAA CAU CUG UAA |
| 2 | H8A (-03+18) | GAU AGG UGG UAU CAA CAU CUG |
| 3 | H8A(-07+18) | GAU AGG UGG UAU CAA CAU CUG UAA G |
| 4 | H8A(-06+14) | GGU GGU AUC AAC AUC UGU AA |
| 5 | H8A(-10+10) | GUA UCA ACA UCU GUA AGC AC |
| 6 | H7A(+45+67) | UGC AUG UUC CAG UCG UUG UGU GG |
| 7 | H7A(+02+26) | CAC UAU UCC AGU CAA AUA GGU CUG G |
| 8 | H7D(+15-10) | AUU UAC CAA CCU UCA GGA UCG AGU A |
| 9 | H7A(-18+03) | GGC CUA AAA CAC AUA CAC AUA |
| 10 | C6A(-10+10) | CAU UUU UGA CCU ACA UGU GG |
| 11 | C6A(-14+06) | UUU GAC CUA CAU GUG GAA AG |
| 12 | C6A(-14+12) | UAC AUU UUU GAC CUA CAU GUG GAA AG |
| 13 | C6A(-13+09) | AUU UUU GAC CUA CAU GGG AAA G |
| 14 | CH6A(+69+91) | UAC GAG UUG AUU GUC GGA CCC AG |
| 15 | C6D(+12-13) | GUG GUC UCC UUA CCU AUG ACU GUG G |
| 16 | C6D(+06-11) | GGU CUC CUU ACC UAU GA |
| 17 | H6D(+04-21) | UGU CUC AGU AAU CUU CUU ACC UAU |
| 18 | H6D(+18-04) | UCU UAC CUA UGA CUA UGG AUG AGA |
| 19 | H4A(+13+32) | GCA UGA ACU CUU GUG GAU CC |
| 20 | H4D(+04-16) | CCA GGG UAC UAC UUA CAU UA |
| 21 | H4D(-24-44) | AUC GUG UGU CAC AGC AUC CAG |
| 22 | H4A(+11+40) | UGU UCA GGG CAU GAA CUC UUG UGG AUC CUU |
| 23 | H3A(+30+60) | UAG GAG GCG CCU CCC AUC CUG UAG GUC ACU G |
| 24 | H3A(+35+65) | AGG UCU AGG AGG CGC CUC CCA UCC UGU AGG U |
| 25 | H3A(+30+54) | GCG CCU CCC AUC CUG UAG GUC ACU G |
| 26 | H3D(+46-21) | CUU CGA GGA GGU CUA GGA GGC GCC UC |
| 27 | H3A(+30+50) | CUC CCA UCC UGU AGG UCA CUG |
| 28 | H3D(+19-03) | UAC CAG UUU UUG CCC UGU CAG G |
| 29 | H3A(-06+20) | UCA AUA UGC UGC UUC CCA AAC UGA AA |
| 30 | H3A(+37+61) | CUA GGA GGC GCC UCC CAU CCU GUA G |

TABLE 1A-continued

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptide nucleic acids or morpholinos, these U bases may be shown as "T".

| SEQ ID | SEQUENCE | NUCLEOTIDE SEQUENCE (5'-3') |
|---|---|---|
| 31 | H5A(+20+50) | UUA UGA UUU CCA UCU ACG AUG UCA GUA CUU C |
| 32 | H5D(+25-05) | CUU ACC UGC CAG UGG AGG AUU AUA UUC CAA A |
| 33 | H5D(+10-15) | CAU CAG GAU UCU UAC CUG CCA GUG G |
| 34 | H5A(+10+34) | CGA UGU CAG UAC UUC CAA UAU UCA C |
| 35 | H5D(-04-21) | ACC AUU CAU CAG GAU UCU |
| 36 | H5D(+16-02) | ACC UGC CAG UGG AGG AUU |
| 37 | H5A(-07+20) | CCA AUA UUC ACU AAA UCA ACC UGU UAA |
| 38 | H5D(+18-12) | CAG GAU UGU UAC CUG CCA GUG GAG GAU UAU |
| 39 | H5A(+05+35) | ACG AUG UCA GUA CUU CCA AUA UUC ACU AAA U |
| 40 | H5A(+15+45) | AUU UCC AUC UAC GAU GUC AGU ACU UCC AAU A |
| 41 | H10A(-05+16) | CAG GAG CUU CCA AAU GCU GCA |
| 42 | H10A(-05+24) | CUU GUC UUC AGG AGC UUC CAA AUG CUG CA |
| 43 | H10A(+98+119) | UCC UCA GCA GAA AGA AGC CAC G |
| 44 | H10A(+130+149) | UUA GAA AUC UCU CCU UGU GC |
| 45 | H10A(-33-14) | UAA AUU GGG UGU UAC ACA AU |
| 46 | H11D(+26+49) | CCC UGA GGC AUU CCC AUC UUG AAU |
| 47 | H11D(+11-09) | AGG ACU UAC UUG CUU UGU UU |
| 48 | H11A(+118+140) | CUU GAA UUU AGG AGA UUC AUC UG |
| 49 | H11A(+75+97) | CAU CUU CUG AUA AUU UUC CUG UU |
| 50 | H12A(+52+75) | UCU UCU GUU UUU GUU AGC CAG UCA |
| 51 | H12A(-10+10) | UCU AUG UAA ACU GAA AAU UU |
| 52 | H12A(+11+30) | UUC UGG AGA UCC AUU AAA AC |
| 53 | H13A(+77+100) | CAG CAG UUG CGU GAU CUC CAC UAG |
| 54 | H13A(+55+75) | UUC AUC AAC UAC CAC CAC CAU |
| 55 | H13D(+06-19) | CUA AGC AAA AUA AUC UGA CCU UAA G |
| 56 | H14A(+37+64) | CUU GUA AAA GAA CCC AGC GGU CUU CUG U |
| 57 | H14A(+14+35) | CAU CUA CAG AUG UUU GCC CAU C |
| 58 | H14A(+51+73) | GAA GGA UGU CUU GUA AAA GAA CC |
| 59 | H14D(-02+18) | ACC UGU UCU UCA GUA AGA CG |
| 60 | H14D(+14-10) | CAU GAC ACA CCU GUU CUU CAG UAA |
| 61 | H14A(+61+80) | CAU UUG AGA AGG AUG UCU UG |
| 62 | H14A(-12+12) | AUC UCC AAU ACU GGA GAA AGA |

TABLE 1A-continued

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptide nucleic acids or morpholinos, these U bases may be shown as "T".

| SEQ ID | SEQUENCE | NUCLEOTIDE SEQUENCE (5'-3') |
|---|---|---|
| 63 | H15A(-12+19) | GCC AUG CAC UAA AAA GGC ACU GCA AGA CAU U |
| 64 | H15A(+48+71) | UCU UUA AAG CCA GUU GUG UGA AUC |
| 65 | H15A(+08+28) | UUU CUG AAA GCC AUG CAC UAA |
| 66 | H15D(+17-08) | GUA CAU ACG GCC AGU UUU UGA AGA C |
| 67 | H16A(-12+19) | CUA GAU CCG CUU UUA AAA CCU GUU AAA ACA A |
| 68 | H16A(-06+25) | UCU UUU CUA GAU CCG CUU UUA AAA CCU GUU A |
| 69 | H16A(-06+19) | CUA GAU CCG CUU UUA AAA CCU GUU A |
| 70 | H16A(+87+109) | CCG UCU UCU GGG UCA CUG ACU UA |
| 71 | H16A(-07+19) | CUA GAU CCG CUU UUA AAA CCU GUU AA |
| 72 | H16A(-07+13) | CCG CUU UUA AAA CCU GUU AA |
| 73 | H16A(+12+37) | UGG AUU GCU UUU UCU UUU CUA GAU CC |
| 74 | H16A(+92+116) | CAU GCU UCC GUC UUC UGG GUC ACU G |
| 75 | H16A(+45+67) | G AUC UUG UUU GAG UGA AUA CAG U |
| 76 | H16A(+105+126) | GUU AUC CAG CCA UGC UUC CGU C |
| 77 | H16D(+05-20) | UGA UAA UUG GUA UCA CUA ACC UGU G |
| 78 | H16D(+12-11) | GUA UCA CUA ACC UGU GCU GUA C |
| 79 | H19A(+35+53) | CUG CUG GCA UCU UGC AGU U |
| 80 | H19A(+35+65) | GCC UGA GCU GAU CUG CUG GCA UCU UGC AGU U |
| 81 | H20A(+44+71) | CUG GCA GAA UUC GAU CCA CCG GCU GUU C |
| 82 | H20A(+147+168) | CAG CAG UAG UUG UCA UCU GCU C |
| 83 | H20A(+185+203) | UGA UGG GGU GGU GGG UUG G |
| 84 | H20A(-08+17) | AUC UGC AUU AAC ACC CUC UAG AAA G |
| 85 | H20A(+30+53) | CCG GCU GUU CAG UUG UUC UGA GGC |
| 86 | H20A(-11+17) | AUC UGC AUU AAC ACC CUC UAG AAA GAA A |
| 87 | H20D(+08-20) | GAA GGA GAA GAG AUU CUU ACC UUA CAA A |
| 88 | H20A(+44+63) | AUU CGA UCC ACC GGC UGU UC |
| 89 | H20A(+149+168 | CAG CAG UAG UUG UCA UCU GC |
| 90 | H21A(-06+16) | GCC GGU UGA CUU CAU CCU GUG C |
| 91 | H21A(+85+106) | CUG CAU CCA GGA ACA UGG GUC C |
| 92 | H21A(+85+108) | GUC UGC AUC CAG GAA CAU GGG UC |
| 93 | H21A(+08+31) | GUU GAA GAU CUG AUA GCC GGU UGA |
| 94 | H21D(+18-07) | UAC UUA CUG UCU GUA GCU CUU UCU |
| 95 | H22A(+22+45) | CAC UCA UGG UCU CCU GAU AGC GCA |

TABLE 1A-continued

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptide nucleic acids or morpholinos, these U bases may be shown as "T".

| SEQ ID | SEQUENCE | NUCLEOTIDE SEQUENCE (5'-3') |
|---|---|---|
| 96 | H22A(+125+106) | CUG CAA UUC CCC GAG UCU CUG C |
| 97 | H22A(+47+69) | ACU GCU GGA CCC AUG UCC UGA UG |
| 98 | H22A(+80+101) | CUA AGU UGA GGU AUG GAG AGU |
| 99 | H22D(+13-11) | UAU UCA CAG ACC UGC AAU UCC CC |
| 100 | H23A(+34+59) | ACA GUG GUG CUG AGA UAG UAU AGG CC |
| 101 | H23A(+18+39) | UAG GCC ACU UUG UUG CUC UUG C |
| 102 | H23A(+72+90) | UUC AGA GGG CGC UUU CUU C |
| 103 | H24A(+48+70) | GGG CAG GCC AUU CCU CCU UCA GA |
| 104 | H24A(-02+22) | UCU UCA GGG UUU GUA UGU GAU UCU |
| 105 | H25A(+9+36) | CUG GGC UGA AUU GUC UGA AUA UCA CUG |
| 106 | H25A(+131+156) | CUG UUG GCA CAU GUG AUC CCA CUG AG |
| 107 | H25D(+16-08) | GUC UAU ACC UGU UGG CAC AUG UGA |
| 108 | H26A(+132+156) | UGC UUU CUG UAA UUC AUC UGG AGU U |
| 109 | H26A(-07+19) | CCU CCU UUC UGG CAU AGA CCU UCC AC |
| 110 | H26A(+68+92) | UGU GUC AUC CAU UCG UGC AUC UCU G |
| 111 | H27A(+82+106) | UUA AGG CCU CUU GUG CUA CAG GUG G |
| 112 | H27A(-4+19) | GGG GCU CUU CUU UAG CUC UCU GA |
| 113 | H27D(+19-03) | GAC UUC CAA AGU CUU GCA UUU C |
| 114 | H28A(-05+19) | GCC AAC AUG CCC AAA CUU CCU AAG |
| 115 | H28A(+99+124) | CAG AGA UUU CCU CAG CUC CGC CAG GA |
| 116 | H28D(+16-05) | CUU ACA UCU AGC ACC UCA GAG |
| 117 | H29A(+57+81) | UCC GCC AUC UGU UAG GGU CUG UGC C |
| 118 | H29A(+18+42) | AUU UGG GUU AUC CUC UGA AUG UCG C |
| 119 | H29D(+17-05) | CAU ACC UCU UCA UGU AGU UCC C |
| 120 | H30A(+122+147) | CAU UUG AGC UGC GUC CAC CUU GUC UG |
| 121 | H30A(+25+50) | UCC UGG GCA GAC UGG AUG CUC UGU UC |
| 122 | H30D(+19-04) | UUG CCU GGG CUU CCU GAG GCA UU |
| 123 | H31D(+06-18) | UUC UGA AAU AAC AUA UAC CUG UGC |
| 124 | H31D(+03-22) | UAG UUU CUG AAA UAA CAU AUA CCU G |
| 125 | H31A(+05+25) | GAC UUG UCA AAU CAG AUU GGA |
| 126 | H31D(+04-20) | GUU UCU GAA AUA ACA UAU ACC UGU |
| 127 | H32D(+04-16) | CAC CAG AAA UAC AUA CCA CA |
| 128 | H32A(+151+170) | CAA UGA UUU AGC UGU GAC UG |
| 129 | H32A(+10+32) | CGA AAC UUC AUG GAG ACA UCU UG |

TABLE 1A-continued

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptide nucleic acids or morpholinos, these U bases may be shown as "T".

| SEQ ID | SEQUENCE | NUCLEOTIDE SEQUENCE (5'-3') |
|---|---|---|
| 130 | H32A(+49+73) | CUU GUA GAC GCU GCU CAA AAU UGG C |
| 131 | H33D(+09-11) | CAU GCA CAC ACC UUU GCU CC |
| 132 | H33A(+53+76) | UCU GUA CAA UCU GAC GUC CAG UCU |
| 133 | H33A(+30+56) | GUC UUU AUC ACC AUU UCC ACU UCA GAC |
| 134 | H33A(+64+88) | CCG UCU GCU UUU UCU GUA CAA UCU G |
| 135 | H34A(+83+104) | UCC AUA UCU GUA GCU GCC AGC C |
| 136 | H34A(+143+165) | CCA GGC AAC UUC AGA AUC CAA AU |
| 137 | H34A(-20+10) | UUU CUG UUA CCU GAA AAG AAU UAU AAU GAA |
| 138 | H34A(+46+70) | CAU UCA UUU CCU UUC GCA UCU UAC G |
| 139 | H34A(+95+120) | UGA UCU CUU UGU CAA UUC CAU AUC UG |
| 140 | H34D(+10-20) | UUC AGU GAU AUA GGU UUU ACC UUU CCC CAG |
| 141 | H34A(+72+96) | CUG UAG CUG CCA GCC AUU CUG UCA AG |
| 142 | H35A(+141+161) | UCU UCU GCU CGG GAG GUG ACA |
| 143 | H35A(+116+135) | CCA GUU ACU AUU CAG AAG AC |
| 144 | H35A(+24+43) | UCU UCA GGU GCA CCU UCU GU |
| 145 | H36A(+26+50) | UGU GAU GUG GUC CAC AUU CUG GUC A |
| 146 | H36A(-02+18) | CCA UGU GUU UCU GGU AUU CC |
| 147 | H37A(+26+50) | CGU GUA GAG UCC ACC UUU GGG CGU A |
| 148 | H37A(+82+105) | UAC UAA UUU CCU GCA GUG GUC ACC |
| 149 | H37A(+134+157) | UUC UGU GUG AAA UGG CUG CAA AUC |
| 150 | H38A(-01+19) | CCU UCA AAG GAA UGG AGG CC |
| 151 | H38A(+59+83) | UGC UGA AUU UCA GCC UCC AGU GGU U |
| 152 | H38A(+88+112) | UGA AGU CUU CCU CUU UCA GAU UCA C |
| 153 | H39A(+62+85) | CUG GCU UUC UCU CAU CUG UGA UUC |
| 154 | H39A(+39+58) | GUU GUA AGU UGU CUC CUC UU |
| 155 | H39A(+102+121) | UUG UCU GUA ACA GCU GCU GU |
| 156 | H39D(+10-10) | GCU CUA AUA CCU UGA GAG CA |
| 157 | H40A(-05+17) | CUU UGA GAC CUC AAA UCC UGU U |
| 158 | H40A(+129+153) | CUU UAU UUU CCU UUC AUC UCU GGG C |
| 159 | H42A(-04+23) | AUC GUU UCU UCA CGG ACA GUG UGC UGG |
| 160 | H42A(+86+109) | GGG CUU GUG AGA CAU GAG UGA UUU |
| 161 | H42D(+19-02) | A CCU UCA GAG GAC UCC UCU UGC |
| 162 | H43D(+10-15) | UAU GUG UUA CCU ACC UUU GUC GGU C |
| 163 | H43A(+101+120) | GGA GAG AGC UUC CUG UAG CU |

TABLE 1A-continued

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptide nucleic acids or morpholinos, these U bases may be shown as "T".

| SEQ ID | SEQUENCE | NUCLEOTIDE SEQUENCE (5'-3') |
|---|---|---|
| 164 | H43A(+78+100) | UCA CCC UUU CCA CAG GCG UUG CA |
| 165 | H44A(+85+104) | UUU GUG UCU UUC UGA GAA AC |
| 166 | H44D(+10-10) | AAA GAC UUA CCU UAA GAU AC |
| 167 | H44A(-06+14) | AUC UGU CAA AUC GCC UGC AG |
| 168 | H46D(+16-04) | UUA CCU UGA CUU GCU CAA GC |
| 169 | H46A(+90+109) | UCC AGG UUC AAG UGG GAU AC |
| 170 | H47A(+76+100) | GCU CUU CUG GGC UUA UGG GAG CAC U |
| 171 | H47D(+25-02) | ACC UUU AUC CAC UGG AGA UUU GUC UGC |
| 172 | H47A(-9+12) | UUC CAC CAG UAA CUG AAA CAG |
| 173 | H50A(+02+30) | CCA CUC AGA GCU CAG AUC UUC UAA CUU CC |
| 174 | H50A(+07+33) | CUU CCA CUC AGA GCU CAG AUC UUC UAA |
| 175 | H50D(+07-18) | GGG AUC CAG UAU ACU UAC AGG CUC C |
| 176 | H51A(-01+25) | ACC AGA GUA ACA GUC UGA GUA GGA GC |
| 177 | H51D(+16-07) | CUC AUA CCU UCU GCU UGA UGA UC |
| 178 | H51A(+111 +134) | UUC UGU CCA AGC CCG GUU GAA AUC |
| 179 | H51A(+61+90) | ACA UCA AGG AAG AUG GCA UUU CUA GUU UGG |
| 180 | H51A(+66+90) | ACA UCA AGG AAG AUG GCA UUU CUA G |
| 181 | H51A(+66+95) | CUC CAA CAU CAA GGA AGA UGG CAU UUC UAG |
| 182 | H51D(+08-17) | AUC AUU UUU UCU CAU ACC UUC UGC U |
| 183 | H51A/D(+08-17) & (-15+) | AUC AUU UUU UCU CAU ACC UUC UGC UAG GAG CUA AAA |
| 184 | H51A(+175+195) | CAC CCA CCA UCA CCC UCU GUG |
| 185 | H51A(+199+220) | AUC AUC UCG UUG AUA UCC UCA A |
| 186 | H52A(-07+14) | UCC UGC AUU GUU GCC UGU AAG |
| 187 | H52A(+12+41) | UCC AAC UGG GGA CGC CUC UGU UCC AAA UCC |
| 188 | H52A(+17+37) | ACU GGG GAC GCC UCU GUU CCA |
| 189 | H52A(+93+112) | CCG UAA UGA UUG UUC UAG CC |
| 190 | H52D(+05-15) | UGU UAA AAA ACU UAC UUC GA |
| 191 | H53A(+45+69) | CAU UCA ACU GUU GCC UCC GGU UCU G |

TABLE 1A-continued

Description of 2'-O-methyl phosphorothioate antisense oligonucleotides that have been used to date to study induced exon skipping during the processing of the dystrophin pre-mRNA. Since these 2'-O-methyl antisense oligonucleotides are more RNA-like, U represents uracil. With other antisense chemistries such as peptide nucleic acids or morpholinos, these U bases may be shown as "T".

| SEQ ID | SEQUENCE | NUCLEOTIDE SEQUENCE (5'-3') |
|---|---|---|
| 192 | H53A(+39+62) | CUG UUG CCU CCG GUU CUG AAG GUG |
| 193 | H53A(+39+69) | CAU UCA ACU GUU GCC UCC GGU UCU GAA GGU G |
| 194 | H53D(+14-07) | UAC UAA CCU UGG UUU CUG UGA |
| 195 | H53A(+23+47) | CUG AAG GUG UUC UUG UAC UUC AUC C |
| 196 | H53A(+150+176) | UGU AUA GGG ACC CUC CUU CCA UGA CUC |
| 197 | H53D(+20-05) | CUA ACC UUG GUU UCU GUG AUU UUC U |
| 198 | H53D(+09-18) | GGU AUC UUU GAU ACU AAC CUU GGU UUC |
| 199 | H53A(-12+10) | AUU CUU UCA CUU AGA AUA AAA G |
| 200 | H53A(-07+18) | GAU UCU GAA UUC UUU CAA CUA GAA U |
| 201 | H53A(+07+26) | AUC CCA CUG AUU CUG AAU UC |
| 202 | H53A(+124+145) | UUG GCU CUG GCC UGU CCU AAG A |
| 203 | H46A(+86+115) | CUC UUU UCC AGG UUC AAG UGG GAU ACU AGC |
| 204 | H46A(+107+137) | CAA GCU UUU CUU UUA GUU GCU GCU CUU UUC C |
| 205 | H46A(-10+20) | UAU UCU UUU GUU CUU CUA GCC UGG AGA AAG |
| 206 | H46A(+50+77) | CUG CUU CCU CCA ACC AUA AAA CAA AUU C |
| 207 | H45A(-06+20) | CCA AUG CCA UCC UGG AGU UCC UGU AA |
| 208 | H45A(+91 +110) | UCC UGU AGA AUA CUG GCA UC |
| 209 | H45A(+125+151) | UGC AGA CCU CCU GCC ACC GCA GAU UCA |
| 210 | H45D(+16 -04) | CUA CCU CUU UUU UCU GUC UG |
| 211 | H45A(+71+90) | UGU UUU UGA GGA UUG CUG AA |

TABLE 1B

Description of a cocktail of 2'-O-methyl phosphorothioate antisense oligonucleotides that have been used to date to study induced exon skipping during the processing of the dystrophin pre-mRNA.

| SEQ ID | SEQUENCE | NUCLEOTIDE SEQUENCE (5'-3') |
|---|---|---|
| 81 | H20A(+44+71) | CUG GCA GAA UUC GAU CCA CCG GCU GUU C |
| 82 | H20A(+147+168) | CAG CAG UAG UUG UCA UCU GCU C |
| 80 | H19A(+35+65) | GCC UGA GCU GAU CUG CUG GCA UCU UGC |
| 81 | H20A(+44+71) | CUG GCA GAA UUC GAU CCA CCG GCU GUU C |
| 82 | H20A(+147+168) | AGU U CAG CAG UAG UUG UCA UCU GCU C |

TABLE 1B-continued

Description of a cocktail of 2'-O-methyl phosphorothioate antisense oligonucleotides that have been used to date to study induced exon skipping during the processing of the dystrophin pre-mRNA.

| SEQ ID | SEQUENCE | NUCLEOTIDE SEQUENCE (5'-3') |
|---|---|---|
| 194 | H53D(+14-07) | UAC UAA CCU UGG UUU CUG UGA |
| 195 | H53A(+23+47) | CUG AAG GUG UUC UUG UAC UUC AUC C |
| 196 | H53A(+150+175) | UGU AUA GGG ACC CUC CUU CCA UGA CUC |

TABLE 1C

Description of a "weasel" of 2'-O-methyl phosphorothioate antisense oligonucleotides that have been used to date to study induced exon skipping during the processing of the dystrophin pre-mRNA.

| SEQ ID | SEQUENCE | NUCLEOTIDE SEQUENCE (5'-3') |
|---|---|---|
| 81 | H20A(+44+71)- | CUG GCA GAA UUC GAU CCA CCG GCU GUU C- |
| 82 | H20A(+147+168) | CAG CAG UAG UUG UCA UCU GCU C |
| 80 | H19A(+35+65)- | GCC UGA GCU GAU CUG CUG GCA UCU UGC AGU U |
| 88 | H20A(+44+63)- | -AUU CGA UCC ACC GGC UGU UC- |
| 79 | H20A(+149+168) | CUG CUG GCA UCU UGC AGU U |
| 80 | H19A(+35+65)- | GCC UGA GCU GAU CUG CUG GCA UCU UGC AGU U |
| 88 | H20A(+44+63) | -AUU CGA UCC ACC GGC UGU UC- |
| 80 | H19A(+35+65)- | GCC UGA GCU GAU CUG CUG GCA UCU UGC AGU U |
| 79 | H20A(+149+168) | -CUG CUG GCA UCU UGC AGU U |
| 138 | H34A(+46+70)- | CAU UCA UUU CCU UUC GCA UCU UAC G- |
| 139 | H34A(+94+120) | UGA UCU CUU UGU CAA UUC CAU AUC UG |
| 124 | H31D(+03-22)-UU- | UAG UUU CUG AAA UAA CAU AUA CCU G-UU- |
| 144 | H35A(+24+43) | UCU UCA GGU GCA CCU UCU GU |
| 195 | H53A(+23+47)-AA- | CUG AAG GUG UUC UUG UAC UUC AUC C-AA- |
| 196 | H53A(+150+175)-AA- | UGU AUA GGG ACC CUC CUU CCA UGA CUC-AA- |
| 194 | H53D(+14-07) | UAC UAA CCU UGG UUU CUG UGA |
| — 212 | Aimed at exons 19/20/20 | CAG CAG UAG UUG UCA UCU GCU CAA CUG GCA GAA UUC GAU CCA CCG GCU GUU CAA GCC UGA GCU GAU CUG CUC GCA UCU UGC AGU |

DETAILED DESCRIPTION OF THE INVENTION

General

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

Sequence identity numbers (SEQ ID NO:) containing nucleotide and amino acid sequence information included in this specification are collected at the end of the description and have been prepared using the programme PatentIn Version 3.0. Each nucleotide or amino acid sequence is identified in the sequence listing by the numeric indicator <210> followed by the sequence identifier (e.g. <210>1, <210>2, etc.). The length, type of sequence and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> followed by the sequence identifier (e.g. <400>1, <400>2, etc.).

An antisense molecules nomenclature system was proposed and published to distinguish between the different antisense molecules (see Mann et al., (2002) *J Gen Med* 4, 644-654). This nomenclature became especially relevant when testing several slightly different antisense molecules, all directed at the same target region, as shown below:

*H#A/D(x:y).*

The first letter designates the species (e.g. H: human, M: murine, C: canine) "#" designates target dystrophin exon number.

"A/D" indicates acceptor or donor splice site at the beginning and end of the exon, respectively.

(x y) represents the annealing coordinates where "−" or "+" indicate intronic or exonic sequences respectively. As an example, A(−6+18) would indicate the last 6 bases of the intron preceding the target exon and the first 18 bases of the target exon. The closest splice site would be the acceptor so these coordinates would be preceded with an "A". Describing annealing coordinates at the donor splice site could be D(+2−18) where the last 2 exonic bases and the first 18 intronic bases correspond to the annealing site of the antisense molecule. Entirely exonic annealing coordinates that would be represented by A(+65+85), that is the site between the 65th and 85th nucleotide from the start of that exon.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

As used necessarily herein the term "derived" and "derived from" shall be taken to indicate that a specific integer may be obtained from a particular source albeit not directly from that source.

Throughout this specification, unless the context requires o#herwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Description of the Preferred Embodiment

When antisense molecule(s) are targeted to nucleotide sequences involved in splicing in exons within pre-mRNA sequences, normal splicing of the exon may be inhibited causing the splicing machinery to by-pass the entire mutated exon from the mature mRNA. The concept of antisense oligonucleotide induced exon skipping is shown in FIG. 2. In many genes, deletion of an entire exon would lead to the production of a non-functional protein through the loss of important functional domains or the disruption of the reading frame. In some proteins, however, it is possible to shorten the protein by deleting one or more exons, without disrupting the reading frame, from within the protein without seriously altering the biological activity of the protein. Typically, such proteins have a structural role and or possess functional domains at their ends. The present invention describes antisense molecules capable of binding to specified dystrophin pre-mRNA targets and re-directing processing of that gene.

Antisense Molecules

According to a first aspect of the invention, there is provided antisense molecules capable of binding to a selected target to induce exon skipping. To induce exon skipping in exons of the Dystrophin gene transcript, the antisense molecules are preferably selected from the group of compounds shown in Table 1A. There is also provided a combination or "cocktail" of two or more antisense oligonucleotides capable of binding to a selected target to induce exon skipping. To induce exon skipping in exons of the Dystrophin gene transcript, the antisense molecules in a "cocktail" are preferably selected from the group of compounds shown in Table 1B. Alternatively, exon skipping may be induced by antisense oligonucleotides joined together "weasels" preferably selected from the group of compounds shown in Table 1C.

Designing antisense molecules to completely mask consensus splice sites may not necessarily generate any skipping of the targeted exon. Furthermore, the inventors have discovered that size or length of the antisense oligonucleotide itself is not always a primary factor when designing antisense molecules. With some targets such as exon 19, antisense oligonucleotides as short as 12 bases were able to induce exon skipping, albeit not as efficiently as longer (20-31 bases) oligonucleotides. In some other targets, such as murine dystrophin exon 23, antisense oligonucleotides only 17 residues long were able to induce more efficient skipping than another overlapping compound of 25 nucleotides.

The inventors have also discovered that there does not appear to be any standard motif that can be blocked or masked by antisense molecules to redirect splicing. In some exons, such as mouse dystrophin exon 23, the donor splice site was the most amenable to target to re-direct skipping of that exon. It should be noted that designing and testing a series of exon 23 specific antisense molecules to anneal to overlapping regions of the donor splice site showed considerable variation in the efficacy of induced exon skipping. As reported in Mann et al., (2002) there was a significant variation in the efficiency of bypassing the nonsense mutation depending upon antisense oligonucleotide annealing ("Improved antisense oligonucleotide induced exon skipping in the mdx mouse model of muscular dystrophy". *J Gen Med* 4: 644-654). Targeting the acceptor site of exon 23 or several internal domains was not found to induce any consistent exon 23 skipping.

In other exons targeted for removal, masking the donor splice site did not induce any exon skipping. However, by directing antisense molecules to the acceptor splice site (human exon 8 as discussed below), strong and sustained exon skipping was induced. It should be noted that removal of human exon 8 was tightly linked with the co-removal of exon 9. There is no strong sequence homology between the exon 8 antisense oligonucleotides and corresponding regions of exon 9 so it does not appear to be a matter of cross reaction. Rather the splicing of these two exons is inextricably linked. This is not an isolated instance as the same effect is observed in canine cells where targeting exon 8 for removal also resulted in the skipping of exon 9. Targeting exon 23 for removal in the mouse dystrophin pre-mRNA also results in the frequent removal of exon 22 as well. This effect occurs in a dose dependent manner and also indicates close coordinated processing of 2 adjacent exons.

In other targeted exons, antisense molecules directed at the donor or acceptor splice sites did not induce exon skipping while annealing antisense molecules to intra-exonic regions (i.e. exon splicing enhancers within human dystrophin exon 6) was most efficient at inducing exon skipping. Some exons, both mouse and human exon 19 for example, are readily skipped by targeting antisense molecules to a variety of motifs. That is, targeted exon skipping is induced after using antisense oligonucleotides to mask donor and acceptor splice sites or exon splicing enhancers.

To identify and select antisense oligonucleotides suitable for use in the modulation of exon skipping, a nucleic acid sequence whose function is to be modulated must first be identified. This may be, for example, a gene (or mRNA transcribed form the gene) whose expression is associated with a particular disorder or disease state, or a nucleic acid molecule from an infectious agent. Within the context of the present invention, preferred target site(s) are those involved in mRNA splicing (i.e. splice donor sites, splice acceptor sites, or exonic splicing enhancer elements). Splicing branch points and exon recognition sequences or splice enhancers are also potential target sites for modulation of mRNA splicing.

Preferably, the present invention aims to provide antisense molecules capable of binding to a selected target in the dystrophin pre-mRNA to induce efficient and consistent exon skipping. Duchenne muscular dystrophy arises from mutations that preclude the synthesis of a functional dystrophin gene product. These Duchenne muscular dystrophy gene defects are typically nonsense mutations or genomic rearrangements such as deletions, duplications or microdeletions or insertions that disrupt the reading frame. As the human dystrophin gene is a large and complex gene with the 79 exons being spliced together to generate a mature mRNA with an open reading frame of approximately 11,000 bases, there are many positions where these mutations can occur. Consequently, a comprehensive antisense oligonucleotide based therapy to address many of the different disease-causing mutations in the dystrophin gene will require that many exons can be targeted for removal during the splicing process.

Within the context of the present invention, preferred target site(s) are those involved in mRNA splicing (i.e. splice donor sites, splice acceptor sites or exonic splicing enhancer elements). Splicing branch points and exon recognition sequences or splice enhancers are also potential target sites for modulation of mRNA splicing.

The oligonucleotide and the DNA or RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the oligonucleotide and the DNA or RNA target. It is understood in the art that the sequence of an antisense molecule need not be 100% complementary to that of its target sequence to be specifically hybridisable. An antisense molecule is specifically hybridisable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

While the above method may be used to select antisense molecules capable of deleting any exon from within a protein that is capable of being shortened without affecting its biological function, the exon deletion should not lead to a reading frame shift in the shortened transcribed mRNA. Thus, if in a linear sequence of three exons the end of the first exon encodes two of three nucleotides in a codon and the next exon is deleted then the third exon in the linear sequence must start with a single nucleotide that is capable of completing the nucleotide triplet for a codon. If the third exon does not commence with a single nucleotide there will be a reading frame shift that would lead to the generation of truncated or a non-functional protein.

It will be appreciated that the codon arrangements at the end of exons in structural proteins may not always break at the end of a codon, consequently there may be a need to delete more than one exon from the pre-mRNA to ensure in-frame reading of the mRNA. In such circumstances, a plurality of antisense oligonucleotides may need to be selected by the method of the invention wherein each is directed to a different region responsible for inducing splicing in the exons that are to be deleted.

The length of an antisense molecule may vary so long as it is capable of binding selectively to the intended location within the pre-mRNA molecule. The length of such sequences can be determined in accordance with selection procedures described herein. Generally, the antisense molecule will be from about 10 nucleotides in length up to about 50 nucleotides in length. It will be appreciated however that any length of nucleotides within this range may be used in the method. Preferably, the length of the antisense molecule is between 17 to 30 nucleotides in length.

In order to determine which exons can be connected in a dystrophin gene, reference should be made to an exon boundary map. Connection of one exon with another is based on the exons possessing the same number at the 3' border as is present at the 5' border of the exon to which it is being connected. Therefore, if exon 7 were deleted, exon 6 must connect to either exons 12 or 18 to maintain the reading frame. Thus, antisense oligonucleotides would need to be selected which redirected splicing for exons 7 to 11 in the first instance or exons 7 to 17 in the second instance. Another and somewhat simpler approach to restore the reading frame around an exon 7 deletion would be to remove the two flanking exons. Induction of exons 6 and 8 skipping should result in an in-frame transcript with the splicing of exons 5 to 9. In practise however, targeting exon 8 for removal from the pre-mRNA results in the co-removal of exon 9 so the resultant transcript would have exon 5 joined to exon 10. The inclusion or exclusion of exon 9 does not alter the reading frame. Once the antisense molecules to be tested have been identified, they are prepared according to standard techniques known in the art. The most common method for producing antisense molecules is the methylation of the 2' hydroxyribose position and the incorporation of a phosphorothioate backbone produces molecules that superficially resemble RNA but that are much more resistant to nuclease degradation.

To avoid degradation of pre-mRNA during duplex formation with the antisense molecules, the antisense molecules used in the method may be adapted to minimise or prevent cleavage by endogenous RNase H. This property is highly preferred as the treatment of the RNA with the unmethylated oligonucleotides either intracellularly or in crude extracts that contain RNase H leads to degradation of the pre-mRNA: antisense oligonucleotide duplexes. Any form of modified antisense molecules that is capable of bypassing or not inducing such degradation may be used in the present method. An example of antisense molecules which when duplexed with RNA are not cleaved by cellular RNase H is 2'-O-methyl derivatives. 2'-O-methyl-oligoribonucleotides are very stable in a cellular environment and in animal tissues, and their duplexes with RNA have higher Tm values than their ribo- or deoxyribo-counterparts.

Antisense molecules that do not activate RNase H can be made in accordance with known techniques (see, e.g., U.S. Pat. No. 5,149,797). Such antisense molecules, which may be deoxyribonucleotide or ribonucleotide sequences, simply contain any structural modification which sterically hinders or prevents binding of RNase H to a duplex molecule containing the oligonucleotide as one member thereof, which structural modification does not substantially hinder or disrupt duplex formation. Because the portions of the oligonucleotide involved in duplex formation are substantially different from those portions involved in RNase H binding thereto, numerous antisense molecules that do not activate RNase H are available. For example, such antisense molecules may be oligonucleotides wherein at least one, or all, of the inter-nucleotide bridging phosphate residues are modified phosphates, such as methyl phosphonates, methyl phosphorothioates, phosphoromorpholidates, phosphoropiperazidates and phosphoramidates. For example, every other one of the internucleotide bridging phosphate residues may be modified as described. In another non-limiting example, such antisense molecules are molecules wherein at least one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described.

While antisense oligonucleotides are a preferred form of the antisense molecules, the present invention comprehends other oligomeric antisense molecules, including but not limited to oligonucleotide mimetics such as are described below.

Specific examples of preferred antisense compounds useful in this invention include oligonucleotides containing modified backbones or non-natural inter-nucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their inter-nucleoside backbone can also be considered to be oligonucleosides.

In other preferred oligonucleotide mimetics, both the sugar and the inter-nucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleo-bases are retained and are bound directly or indirectly to aza nitrogen atoms of the amide portion of the backbone.

Modified oligonucleotides may also contain one or more substituted sugar moieties. Oligonucleotides may also include nucleobase (often referred to in the art simply as "base") modifications or substitutions. Certain nucleo-bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Another modification of the oligonucleotides of the invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

It is not necessary far all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of this invention, are antisense molecules, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the increased resistance to nuclease degradation, increased cellular uptake, and an additional region for increased binding affinity for the target nucleic acid.

Methods of Manufacturing Antisense Molecules

The antisense molecules used in accordance with this invention may be conveniently and routinely made through the well-known technique of solid phase synthesis. Equipment for such synthesis is sold by several vendors including, for example, Applied Biosystems (Foster City, Calif.). One method for synthesising oligonucleotides on a modified solid support is described in U.S. Pat. No. 4,458,066.

Any other means for such synthesis known in the art may additionally or alternatively be employed. It is well known to use similar techniques to prepare oligonucleotides such as the phosphorothioates~and alkylated derivatives. In one such automated embodiment, diethyl-phosphoramidites are used as starting materials and may be synthesized as described by Beaucage, et al., (1981) *Tetrahedron Letters*, 22:1859-1862.

The antisense molecules of the invention are synthesised in vitro and do not include antisense compositions of biological origin, or genetic vector constructs designed to direct the in vivo synthesis of antisense molecules. The molecules of the invention may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

Therapeutic Agents

The present invention also can be used as a prophylactic or therapeutic, which may be utilised for the purpose of treatment of a genetic disease.

Accordingly, in one embodiment the present invention provides antisense molecules that bind to a selected target in the dystrophin pre-mRNA to induce efficient and consistent exon skipping described herein in a therapeutically effective amount admixed with a pharmaceutically acceptable carrier, diluent, or excipient.

The phrase "pharmaceutically acceptable" refers to molecular entities and compositions that are physiologically tolerable and do not typically produce an allergic or similarly untoward reaction, such as gastric upset and the like, when administered to a patient. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa., (1990).

In a more specific form of the invention there are provided pharmaceutical compositions comprising therapeutically effective amounts of an antisense molecule together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Martin, *Remington's Pharmaceutical Sciences*, 18th Ed. (1990, Mack Publishing Co., Easton, Pa. 18042) pages 1435-1712 that are herein incorporated by reference. The compositions may be prepared in liquid form, or may be in dried powder, such as lyophilised form.

It will be appreciated that pharmaceutical compositions provided according to the present invention may be administered by any means known in the art. Preferably, the pharmaceutical compositions for administration are administered by injection, orally, or by the pulmonary, or nasal route. The antisense molecules are more preferably delivered by intravenous, intra-arterial, intraperitoneal, intramuscular, or subcutaneous routes of administration.

Antisense Molecule Based Therapy

Also addressed by the present invention is the use of antisense molecules of the present invention, for manufacture of a medicament for modulation of a genetic disease.

The delivery of a therapeutically useful amount of antisense molecules may be achieved by methods previously published. For example, intracellular delivery of the antisense molecule may be via a composition comprising an admixture of the antisense molecule and an effective amount of a block copolymer. An example of this method is described in US patent application US 20040248833.

Other methods of delivery of antisense molecules to the nucleus are described in Mann C J et al., (2001) [*"Antisense-induced exon skipping and the synthesis of dystrophin in the mdx mouse"*. Proc., Natl. Acad. Science, 98(1) 42-47J and in Gebski et al., (2003). Human Molecular Genetics, 12(15): 1801-1811.

A method for introducing a nucleic acid molecule into a cell by way of an expression vector either as naked DNA or complexed to lipid carriers, is described in U.S. Pat. No. 6,806,084.

It may be desirable to deliver the antisense molecule in a colloidal dispersion system. Colloidal dispersion systems include macromolecule complexes, nanocapsules, microspheres, beads, and lipid-based systems including oil-in-water emulsions, micelles, mixed micelles, and liposomes or liposome formulations.

Liposomes are artificial membrane vesicles which are useful as delivery vehicles in vitro and in vivo. These formulations may have net cationic, anionic or neutral charge characteristics and are useful characteristics with in vitro, in vivo and ex vivo delivery methods. It has been shown that large unilamellar vesicles (LUV), which range in size from 0.2-4.0.PHI.m can encapsulate a substantial percentage of an aqueous buffer containing large macromolecules. RNA, and DNA can be encapsulated within the aqueous interior and be delivered to cells in a biologically active form (Fraley, et al., Trends Biochem. Sci., 6:77, 1981).

In order for a liposome to be an efficient gene transfer vehicle, the following characteristics should be present: (1) encapsulation of the antisense molecule of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Alternatively, the antisense construct may be combined with other pharmaceutically acceptable carriers or diluents to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration.

The routes of administration described are intended only as a guide since a skilled practitioner will be able to determine readily the optimum route of administration and any dosage for any particular animal and condition. Multiple approaches for introducing functional new genetic material into cells, both in vitro and in vivo have been attempted (Friedmann (1989) Science, 244:1275-1280).

These approaches include integration of the gene to be expressed into modified retroviruses (Friedmann (1989) supra; Rosenberg (1991) Cancer Research 51(18), suppl.: 5074S-5079S); integration into non-retrovirus vectors (Rosenfeld, et al. (1992) Cell, 68:143-155; Rosenfeld, et al. (1991) Science, 252:431-434); or delivery of a transgene linked to a heterologous promoter-enhancer element via liposomes (Friedmann (1989), supra; Brigham, et al. (1989) Am. J. Med. Sci., 298:278-281; Nabel, et al. (1990) Science, 249:1285-1288; Hazinski, et al. (1991) Am. J. Resp. Cell Molec. Biol., 4:206-209; and Wang and Huang (1987) Proc. Natl. Acad. Sci. (USA), 84:7851-7855); coupled to ligand-specific, cation-based transport systems (Wu and Wu (1988) J. Biol. Chem., 263:14621-14624) or the use of naked DNA, expression vectors (Nabel et al. (1990), supra); Wolff et al. (1990) Science, 247:1465-1468). Direct injection of transgenes into tissue produces only localized expression (Rosenfeld (1992) supra); Rosenfeld et al. (1991) supra; Brigham et al. (1989) supra; Nabel (1990) supra; and Hazinski et al. (1991) supra). The Brigham et al. group (Am. J. Med. Sci. (1989) 298:278-281 and Clinical Research (1991) 39 (abstract)) have reported in vivo transfection only of lungs of mice following either intravenous or intratracheal administration of a DNA liposome complex. An example of a review article of human gene therapy procedures is: Anderson, Science (1992) 256:808-813.

The antisense molecules of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, malefic acid, fumaric acid, gluconic acid, citric acid, malic acid, ascorbic acid, benzoic acid, tannic acid, palmitic acid, alginic acid, polygiutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. The pharmaceutical compositions of the present invention may be administered in a number of ways depending upon whether local or systemic treatment is desired and upon the area to be treated. Administration may be topical (including ophthalmic and to mucous membranes including rectal delivery), pulmonary, e.g., by inhalation or insufflation of powders or aerosols, (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

Kits of the Invention

The invention also provides kits for treatment of a patient with a genetic disease which kit comprises at least an antisense molecule, packaged in a suitable container, together with instructions for its use.

In a preferred embodiment, the kits will contain at least one antisense molecule as shown in Table 1A, or a cocktail of antisense molecules as shown in Table 1B or a "weasel" compound as shown in Table 1C. The kits may also contain peripheral reagents such as buffers, stabilizers, etc.

Those of ordinary skill in the field should appreciate that applications of the above method has wide application for identifying antisense molecules suitable for use in the treatment of many other diseases.

EXAMPLES

The following Examples serve to more fully describe the manner of using the above-described invention, as well as to set forth the best modes contemplated for carrying out various aspects of the invention. It is understood that these Examples in no way serve to limit the true scope of this invention, but rather are presented for illustrative purposes. The references cited herein are expressly incorporated by reference.

Methods of molecular cloning, immunology and protein chemistry, which are not explicitly described in the following examples, are reported in the literature and are known by those skilled in the art. General texts that described conventional molecular biology, microbiology, and recombinant DNA techniques within the skill of the art, included, for example: Sambrook et al, *Molecular Cloning: A Laboratory Manual*, Second Edition, Cold Spring Harbor Laboratory Press, Cold Spring Harbor, N.Y. (1989); Glover ed., *DNA Cloning: A Practical Approach*, Volumes I and II, MRL Press, Ltd., Oxford, U. K. (1985); and Ausubel, F., Brent, R., Kingston, R. E., Moore, D. D., Seidman, J. G., Smith, J. A., Struhl, K. *Current Protocols in Molecular Biology*. Greene Publishing Associates/Wiley Intersciences, New York (2002).

Determining Induced Exon Skipping in Human Muscle Cells

Attempts by the inventors to develop a rational approach in antisense molecules design were not completely successful as there did not appear to be a consistent trend that could be applied to all exons. As such, the identification of the most effective and therefore most therapeutic antisense molecules compounds has been the result of empirical studies.

These empirical studies involved the use of computer programs to identify motifs potentially involved in the splicing process. Other computer programs were also used to identify regions of the pre-mRNA which may not have had extensive secondary structure and therefore potential sites for annealing of antisense molecules. Neither of these approaches proved completely reliable in designing antisense oligonucleotides for reliable and efficient induction of exon skipping.

Annealing sites on the human dystrophin pre-mRNA were selected for examination, initially based upon known or predicted motifs or regions involved in splicing. 2OMe antisense oligonucleotides were designed to be complementary to the target sequences under investigation and were synthesised on an Expedite 8909 Nucleic Acid Synthesiser. Upon completion of synthesis, the oligonucleotides were cleaved from the support column and de-protected in ammonium hydroxide before being desalted. The quality of the oligonucleotide synthesis was monitored by the intensity of the trityl signals upon each deprotection step during the synthesis as detected in the synthesis log. The concentration of the antisense oligonucleotide was estimated by measuring the absorbance of a diluted aliquot at 260 nm.

Specified amounts of the antisense molecules were then tested for their ability to induce exon skipping in an in vitro assay, as described below.

Briefly, normal primary myoblast cultures were prepared from human muscle biopsies obtained after informed consent. The cells were propagated and allowed to differentiate into myotubes using standard culturing techniques. The cells were then transfected with the antisense oligonucleotides by delivery of the oligonucleotides to the dells as cationic lipoplexes, mixtures of antisense molecules or cationic liposome preparations.

The cells were then allowed to grow for another 24 hours, after which total RNA was extracted and molecular analysis commenced. Reverse transcriptase amplification (RT-PCR) was undertaken to study the targeted regions of the dystrophin pre-mRNA or induced exonic re-arrangements.

For example, in the testing of an antisense molecule for inducing exon 19 skipping the RT-PCR test scanned several exons to detect involvement of any adjacent exons. For example, when inducing skipping of exon 19, RT-PCR was carried out with primers that amplified across exons 17 and 21. Amplifications of even larger products in this area (i.e. exons 13-26) were also carried out to ensure that there was minimal amplification bias for the shorter induced skipped transcript. Shorter or exon skipped products tend to be amplified more efficiently and may bias the estimated of the normal and induced transcript.

The sizes of the amplification reaction products were estimated on an agarose gel and compared against appropriate size standards. The final confirmation of identity of these products was carried out by direct DNA sequencing to establish that the correct or expected exon junctions have been maintained.

Once efficient exon skipping had been induced with one antisense molecule, subsequent overlapping antisense molecules may be synthesized and then evaluated in the assay as described above. Our definition of an efficient antisense molecule is one that induces strong and sustained exon skipping at transfection concentrations in the order of 300 nM or less.

Antisense Oligonucleotides Directed at Exon 8

Antisense oligonucleotides directed at exon 8 were prepared and tested for their ability to induce exon skipping in human muscle cells using similar methods as described above.

efficient antisense molecules only induced exon skipping at concentrations of 300 nM and above. Therefore, we have shown that targeting of the antisense molecules to motifs involved in the splicing process plays a crucial role in the overall efficacy of that compound.

Efficacy refers to the ability to induce consistent skipping of a target exon. However, sometimes skipping of the target exons is consistently associated with a flanking exon. That is, we have found that the splicing of some exons is tightly linked. For example, in targeting exon 23 in the mouse model of muscular dystrophy with antisense molecules directed at the donor site of that exon, dystrophin transcripts missing exons 22 and 23 are frequently detected. As another example, when using an antisense molecule directed to exon 8 of the human dystrophin gene, all induced transcripts are missing both exons 8 and 9. Dystrophin transcripts missing only exon 8 are not observed.

Table 2 below discloses antisense molecule sequences that induce exon 8 (and 9) skipping.

TABLE 2

| SEQ ID | Antisense Oligonucleotide name | Sequence | Ability to induce skipping |
|---|---|---|---|
| 1 | H8A(-06+18) | 5'-GAU AGG UGG UAU CAA CAU CUG UAA | Very strong to 20 nM |
| 2 | H8A (-03+18) | 5'-GAU AGG UGG UAU CAA CAU CUG | Very strong skipping to 40 nM |
| 3 | H8A(-07+18) | 5'-GAU AGG UGG UAU CAA CAU CUG UAA G | Strong skipping to 40 nM |
| 4 | H8A(-06+14) | 5'-GGU GGU AUC AAC AUC UGU AA | Skipping to 300 nM |
| 5 | H8A(-10+10) | 5'-GUA UCA ACA UCU GUA AGC AC | Patchy/weak skipping to 100 nm |

Figure 3:
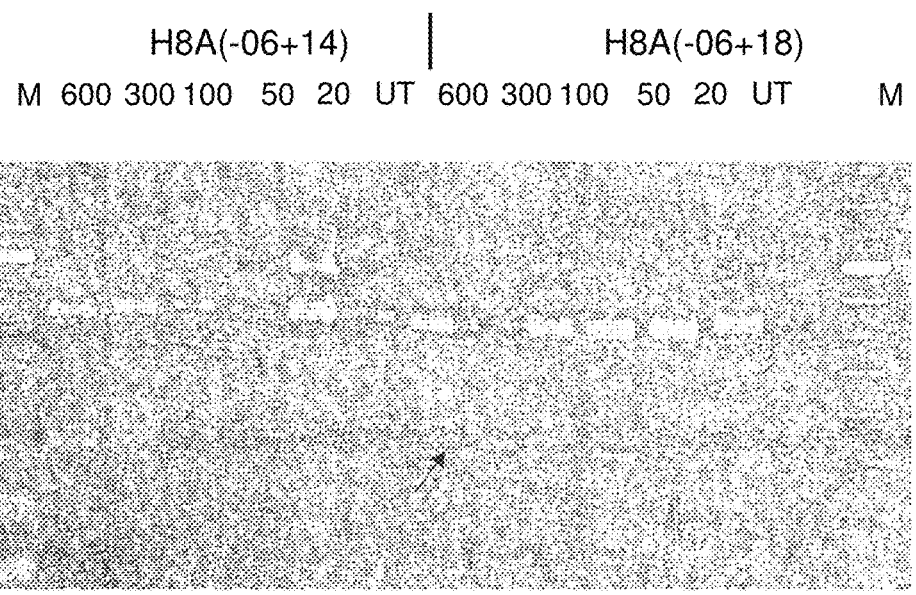
FIG. 3 Gel electrophoresis showing differing efficiencies of two antisense molecules directed at exon 8 acceptor splice site. The preferred compound [H8A(−06+18)] induces strong and consistent exon skipping at a transfection concentration of 20 nanomolar in cultured normal human muscle cells. The less preferred antisense oligonucleotide [H8A(−06+14)] also induces efficient exon skipping, but at much higher concentrations. Other antisense oligonucleotides directed at exon 8 either only induced lower levels of exon skipping or no detectable skipping at all (not shown).

FIG. 3 shows differing efficiencies of two antisense molecules directed at exon 8 acceptor splice site. H8A(-06+18) [SEQ ID NO:1], which anneals to the last 6 bases of intron 7 and the first 18 bases of exon 8, induces substantial exon 8 and 9 skipping when delivered into cells at a concentration of 20 nM. The shorter antisense molecule, H8A(-06+14) [SEQ ID NO: 4] was only able to induce exon 8 and 9 skipping at 300 nM, a concentration some 15 fold higher than H8A(-06+18), which is the preferred antisense molecule.

This data shows that some particular antisense molecules induce efficient exon skipping while another antisense molecule, which targets a near-by or overlapping region, can be much less efficient. Titration studies show one compound is able to induce targeted exon skipping at 20 nM while the less Antisense Oligonucleotides Directed at Exon 7

Antisense oligonucleotides directed at exon 7 were prepared and tested for their ability to induce exon skipping in human muscle cells using similar methods as described above.

Figure 4:
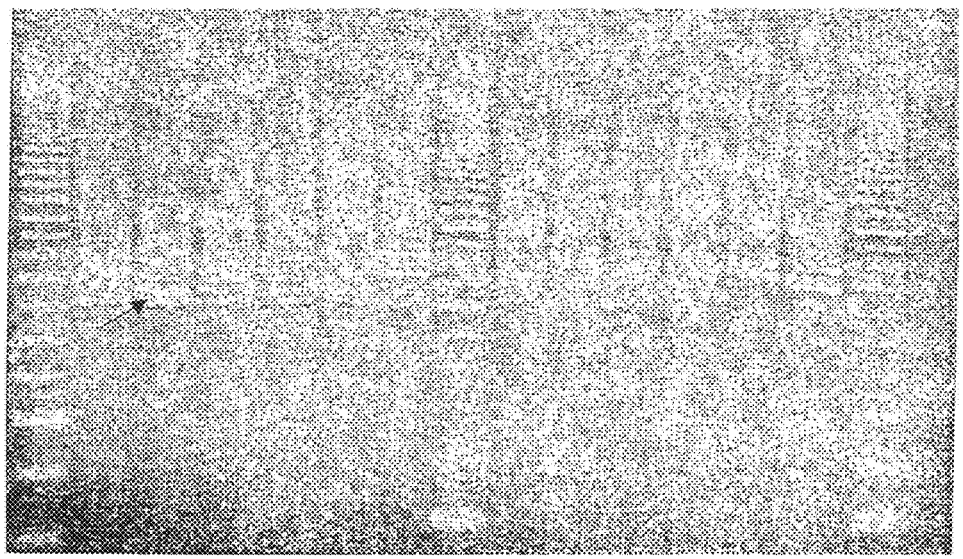
FIG. 4 Gel electrophoresis showing differing efficiencies of two antisense molecules directed at internal domains within exon 7, presumably exon splicing enhancers. The preferred compound [H7A(+45+67)] induces strong and consistent exon skipping at a transfection concentration of 20 nanomolar in cultured human muscle cells. The less preferred antisense oligonucleotide [H7A(+2+26)] induces only low levels of exon skipping at the higher transfection concentrations. Other antisense oligonucleotides directed at exon 7 either only induced lower levels of exon skipping or no detectable skipping at all (not shown).

FIG. 4 shows the preferred antisense molecule, H7A(+45+67) [SEQ ID NO: 6], and another antisense molecule, H7A(+2+26) [SEQ ID NO: 7], inducing exon 7 skipping. Nested amplification products span exons 3 to 9. Additional products above the induced transcript missing exon 7 arise from amplification from carry-over outer primers from the RT-PCR as well as heteroduplex formation.

Table 3 below discloses antisense molecule sequences for induced exon 7 skipping.

TABLE 3

| SEQ ID | Antisense Oligonucleotide name | Sequence | Ability to induce skipping |
|---|---|---|---|
| 6 | H7A(+45+67) | 5'-UGC AUG UUC CAG UCG UUG UGU GG | Strong skipping to 20 nM |

TABLE 3-continued

| SEQ ID | Antisense Oligonucleotide name | Sequence | Ability to induce skipping |
|---|---|---|---|
| 7 | H7A(+02+26) | 5'-CAC UAU UCC AGU CAA AUA GGU CUG G | Weak skipping at 100 nM |
| 8 | H7D(+15-10) | 5'-AUU UAC CAA CCU UCA GGA UCG AGU A | Weak skipping to 300 nM |
| 9 | H7A(-18+03) | 5'-GGC CUA AAA CAC AUA CAC AUA | Weak skipping to 300 nM |

Antisense Oligonucleotides Directed at Exon 6

Antisense oligonucleotides directed at exon 6 were prepared and tested for their ability to induce exon skipping in human muscle cells using similar methods as described above.

Figure 5:
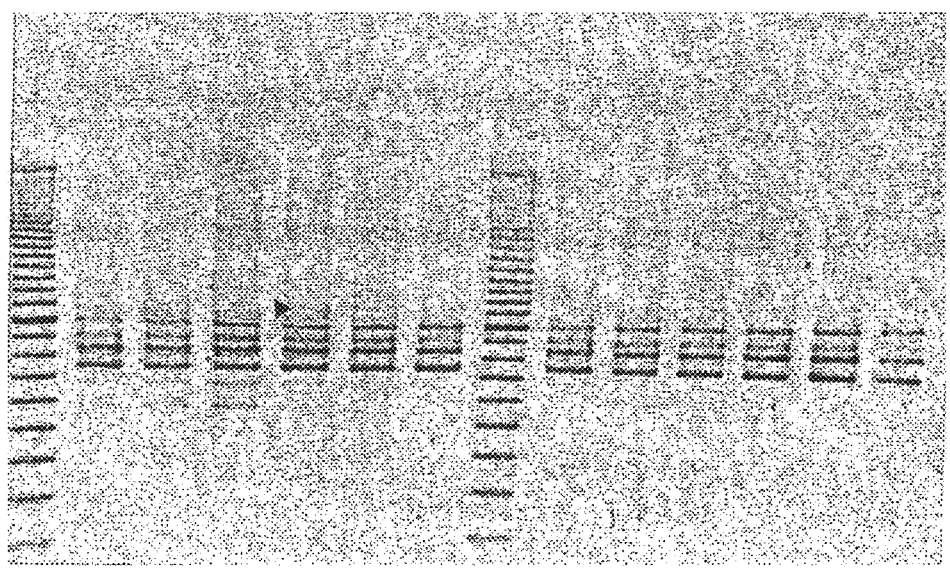
FIG. 5 Gel electrophoresis showing an example of low efficiency exon 6 skipping using two non-preferred antisense molecules directed at human exon 6 donor splice site. Levels of induced exon 6 skipping are either very low [H6D(+04−21)] or almost undetectable [H6D(+18−04)]. These are examples of non-preferred antisense oligonucleotides to demonstrate that antisense oligonucleotide design plays a crucial role in the efficacy of these compounds.

FIG. 5 shows an example of two non-preferred antisense molecules inducing very low levels of exon 6 skipping in cultured human cells. Targeting this exon for specific removal was first undertaken during a study of the canine model using the oligonucleotides as listed in Table 4, below. Some of the human specific oligonucleotides were also evaluated, as shown in FIG. 5. In this example, both antisense molecules target the donor splice site and only induced low levels of exon 6 skipping. Both H6D(+4−21) [SEQ ID NO: 17] and H6D(+18−4) [SEQ ID NO: 18] would be regarded as non-preferred antisense molecules.

Figure 6:
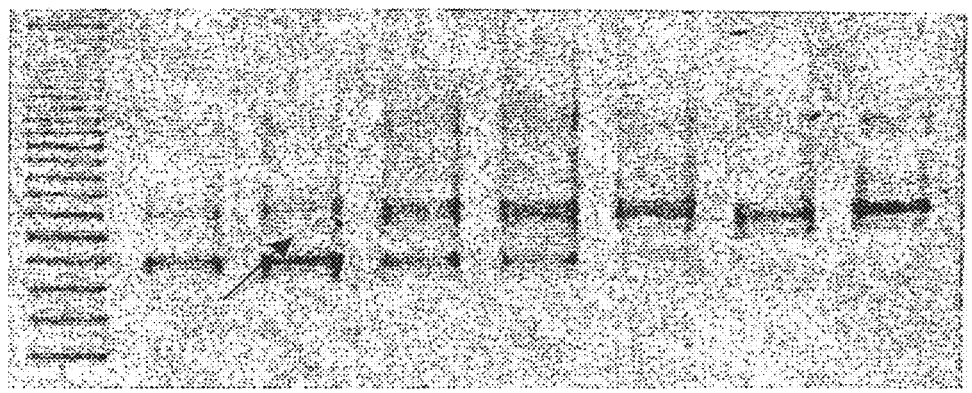
FIG. 6 Gel electrophoresis showing strong and efficient human exon 6 skipping using an antisense molecules [H6A(+69+91)] directed at an exon 6 internal domain, presumably an exon splicing enhancer. This preferred compound induces consistent exon skipping at a transfection concentration of 20 nanomolar in cultured human muscle cells.

One antisense oligonucleotide that induced very efficient exon 6 skipping in the canine model, C6A(+69+91) [SEQ ID NO: 14], would anneal perfectly to the corresponding region in human dystrophin exon 6. This compound was evaluated, found to be highly efficient at inducing skipping of that target exon, as shown in FIG. 6 and is regarded as the preferred compound for induced exon 6 skipping. Table 4 below discloses antisense molecule sequences for induced exon 6 skipping.

Antisense Oligonucleotides Directed at Exon 4

Antisense oligonucleotides directed at exon 4 were prepared and tested for their ability to induce exon skipping in human muscle cells using similar methods as described above.

Figure 7:
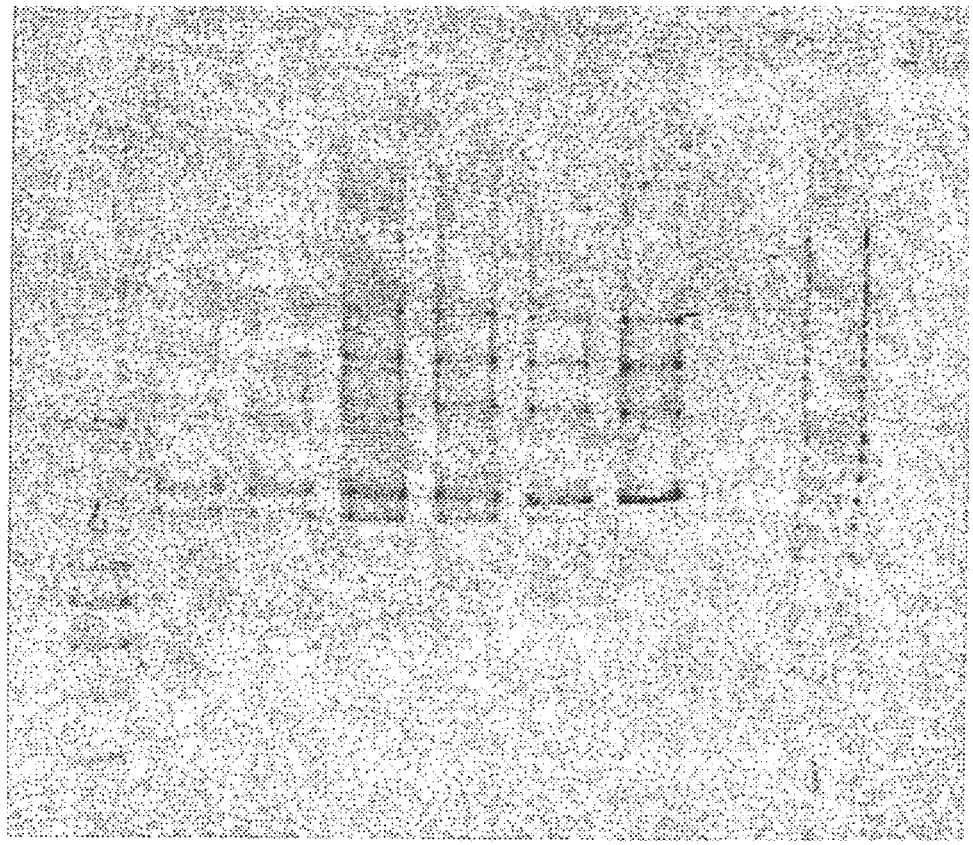
FIG. 7 Gel electrophoresis showing strong human exon 4 skipping using an antisense molecule H4A(+13+32) directed at an exon 6 internal domain, presumably an exon splicing enhancer. This preferred compound induces strong and consistent exon skipping at a transfection concentration of 20 nanomolar in cultured human muscle cells, FIG. 8A Gel electrophoresis showing strong human exon 12 skipping using antisense molecule H12A(+52+75) directed at exon 12 internal domain.

FIG. 7 shows an example of a preferred antisense molecule inducing skipping of exon 4 skipping in cultured human cells. In this example, one preferred antisense compound, H4A(+13+32) [SEQ ID NO:19], which targeted a presumed exonic splicing enhancer induced efficient exon skipping at a concentration of 20 nM while other non-preferred antisense oligonucleotides failed to induce even low levels of exon 4 skipping. Another preferred antisense molecule inducing skipping of exon 4 was H4A(+111+40) [SEQ ID NO:22], which induced efficient exon skipping at a concentration of 20 nM.

Table 5 below discloses antisense molecule sequences for inducing exon 4 skipping.

TABLE 4

| SEQ ID | Antisense Oligo name | Sequence | Ability to induce skipping |
|---|---|---|---|
| 10 | C6A(-10+10) | 5' CAU UUU UGA CCU ACA UGU GG | No skipping |
| 11 | C6A(-14+06) | 5' UUU GAC CUA CAU GUG GAA AG | No skipping |
| 12 | C6A(-14+12) | 5' UAC AUU UUU GAC CUA CAU GUG GAA AG | No skipping |
| 13 | C6A(-13+09) | 5' AUU UUU GAC CUA CAU GGG AAA G | No skipping |
| 14 | CH6A(+69+91) | 5' UAC GAG UUG AUU GUC GGA CCC AG | Strong skipping to 20 nM |
| 15 | C6D(+12-13) | 5' GUG GUC UCC UUA CCU AUG ACU GUG G | Weak skipping at 300 nM |
| 16 | C6D(+06-11) | 5' GGU CUC CUU ACC UAU GA | No skipping |
| 17 | H6D(+04-21) | 5' UGU CUC AGU AAU CUU CUU ACC UAU | Weak skipping to 50 nM |
| 18 | H6D(+18-04) | 5' UCU UAC CUA UGA CUA UGG AUG AGA | Very weak skipping to 300 nM |

TABLE 5

| SEQ ID | Antisense Oligonucleotide name | Sequence | Ability to induce skipping |
|---|---|---|---|
| 19 | H4A(+13+32) | 5' GCA UGA ACU CUU GUG GAU CC | Skipping to 20 nM |
| 22 | H4A(+11+40) | 5' UGU UCA GGG CAU GAA CUC UUG UGG AUC CUU | Skipping to 20 nM |
| 20 | H4D(+04-16) | 5' CCA GGG UAC UAC UUA CAU UA | No skipping |
| 21 | H4D(-24-44) | 5' AUC GUG UGU CAC AGC AUC CAG | No skipping |

Antisense Oligonucleotides Directed at Exon 3

Antisense oligonucleotides directed at exon 3 were prepared and tested for their ability to induce exon skipping in human muscle cells using similar methods as described above.

H3A(+30+60) [SEQ ID NO:23] induced substantial exon 3 skipping when delivered into cells at a concentration of 20 nM to 600 nM. The antisense molecule, H3A(+35+65) [SEQ ID NO: 24] induced exon skipping at 300 nM.

Table 6 below discloses antisense molecule sequences that induce exon 3 skipping.

TABLE 6

| SEQ ID | Antisense Oligonucleotide name | Sequence | Ability to induce skipping |
|---|---|---|---|
| 23 | H3A(+30+60) | UAG GAG GCG CCU CCC AUC CUG UAG GUC ACU G | Moderate skipping to 20 to 600 nM |
| 24 | H3A(+35+65) | AGG UCU AGG AGG CGC CUC CCA UCC UGU AGG U | Working to 300 nM |
| 25 | H3A(+30+54) | GCG CCU CCC AUC CUG UAG GUC ACU G | Moderate 100-600 nM |
| 26 | H3D(+46-21) | CUU CGA GGA GGU CUA GGA GGC GCC UC | No skipping |
| 27 | H3A(+30+50) | CUC CCA UCC UGU AGG UCA CUG | Moderate 20-600 nM |
| 28 | H3D(+19-03) | UAC CAG UUU UUG CCC UGU CAG G | No skipping |
| 29 | H3A(-06+20) | UCA AUA UGC UGC UUCCCA AAC UGA AA | No skipping |
| 30 | H3A(+37+61) | CUA GGA GGC GCC UCC CAU CCU GUA G | No skipping |

Antisense Oligonucleotides Directed at Exon 5

Antisense oligonucleotides directed at exon 5 were prepared and tested for their ability to induce exon skipping in human muscle cells using similar methods as described above.

H5A(+20+50) [SEQ ID NO:31] induces substantial exon 5 skipping when delivered into cells at a concentration of 100 nM. Table 7 below shows other antisense molecules tested. The majority of these antisense molecules were not as effective at exon skipping as H5A(+20+50). However, H5A(+15+45) [SEQ ID NO: 40] was able to induce exon 5 skipping at 300 nM.

Table 7 below discloses antisense molecule sequences that induce exon 5 skipping.

TABLE 7

| SEQ ID | Antisense Oligonucleotide name | Sequence | Ability to induce skipping |
|---|---|---|---|
| 31 | H5A(+20+50) | UUA UGA UUU CCA UCU ACG AUG UCA GUA CUU C | Working to 100 nM |

TABLE 7-continued

| SEQ ID | Antisense Oligonucleotide name | Sequence | Ability to induce skipping |
|---|---|---|---|
| 32 | H5D(+25-05) | CUU ACC UGC CAG UGG AGG AUU AUA UUC CAA A | No skipping |
| 33 | H5D(+10-15) | CAU CAG GAU UCU UAC CUG CCA GUG G | Inconsistent at 300 nM |
| 34 | H5A(+10+34) | CGA UGU CAG UAC UUC CAA UAU UCA C | Very weak |
| 35 | H5D(-04-21) | ACC AUU CAU CAG GAU UCU | No skipping |
| 36 | H5D(+16-02) | ACC UGC CAG UGG AGG AUU | No skipping |
| 37 | H5A(-07+20) | CCA AUA UUC ACU AAA UCA ACC UGU UAA | No skipping |
| 38 | H5D(+18-12) | CAG GAU UCU UAC CUG CCA GUG GAG GAU UAU | No skipping |
| 39 | H5A(+05+35) | ACG AUG UCA GUA CUU CCA AUA UUC ACU AAA U | No skipping |
| 40 | H5A(+15+45) | AUU UCC AUC UAC GAU GUC AGU ACU UCC AAU A | Working to 300 nM |

Antisense Oligonucleotides Directed at Exon 10

Antisense oligonucleotides directed at exon 10 were prepared and tested for their ability to induce exon skipping in human muscle cells using similar methods as described above.

H10A(-05+16) [SEQ ID NO:41] induced substantial exon 10 skipping when delivered into cells. Table 8 below shows other antisense molecules tested. The antisense molecules ability to induce exon skipping was variable. Table 8 below discloses antisense molecule sequences that induce exon 10 skipping.

TABLE 8

| SEQ ID | Antisense Oligonucleotide name | Sequence | Ability to induce skipping |
|---|---|---|---|
| 41 | H10A(-05+16) | CAG GAG CUU CCA AAU GCU GCA | Not tested |
| 42 | H10A(-05+24) | CUU GUC UUC AGG AGC UUC CAA AUG CUG CA | Not tested |
| 43 | H10A(+98+119) | UCC UCA GCA GAA AGA AGC CAC G | Not tested |
| 44 | H10A(+130+149) | UUA GAA AUC UCU CCU UGU GC | No skipping |
| 45 | H10A(-33-14) | UAA AUU GGG UGU UAC ACA AU | No skipping |

Antisense Oligonucleotides Directed at Exon 11

Antisense oligonucleotides directed at exon 11 were prepared and tested for their ability to induce exon skipping in human muscle cells using similar methods as described above.

Figure 8B:
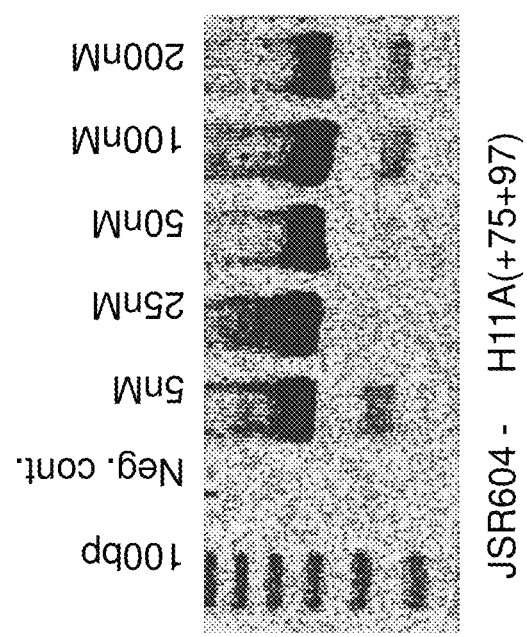
FIG. 8B Gel electrophoresis showing strong human exon 11 skipping using antisense molecule H11A(+75+97) directed at an exon 11 internal domain.

FIG. 8B shows an example of H11A(+75+97) [SEQ ID NO:49] antisense molecule inducing exon 11 skipping in cultured human cells. H11A(+75+97) induced substantial exon 11 skipping when delivered into cells at a concentration of 5 nM. Table 9 below shows other antisense molecules tested. The antisense molecules ability to induce exon skipping was observed at 100 nM.

TABLE 9

| SEQ ID | Antisense Oligonucleotide name | Sequence | Ability to induce skipping |
|---|---|---|---|
| 46 | H11D(+26+49) | CCC UGA GGC AUU CCC AUC UUG AAU | Skipping at 100 nM |
| 47 | H11D(+11-09) | AGG ACU UAC UUG CUU UGU UU | Skipping at 100 nM |
| 48 | H11A(+118+140) | CUU GAA UUU AGG AGA UUC AUC UG | Skipping at 100 nM |
| 49 | H11A(+75+97) | CAU CUU CUG AUA AUU UUC CUG UU | Skipping at 100 nM |
| 46 | H11D(+26+49) | CCC UGA GGC AUU CCC AUC UUG AAU | Skipping at 5 nM |

Antisense Oligonucleotides Directed at Exon 12

Antisense oligonucleotides directed at exon 12 were prepared and tested for their ability to induce exon skipping in human muscle cells using similar methods as described above.

Figure 8A:
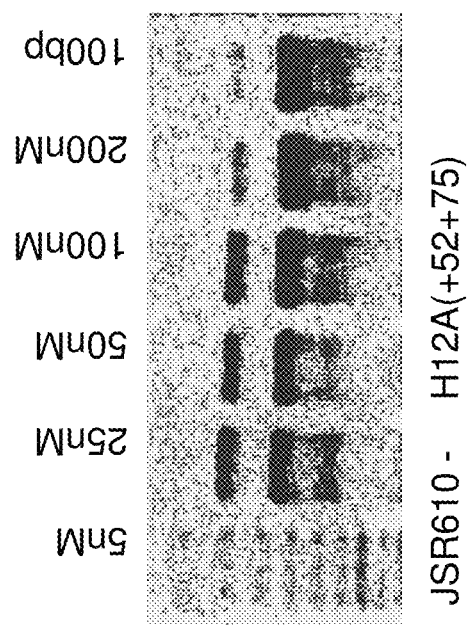

H12A(+52+75) [SEQ ID NO:50] induced substantial exon 12 skipping when delivered into cells at a concentration of 5 nM, as shown in FIG. 8A. Table 10 below shows other antisense molecules tested at a concentration range of 5, 25, 50, 100, 200 and 300 nM. The antisense molecules ability to induce exon skipping was variable.

TABLE 10

| SEQ ID | Antisense Oligonucleotide name | Sequence | Ability to induce skipping |
|---|---|---|---|
| 50 | H12A(+52+75) | UCU UCU GUU UUU GUU AGC CAG UCA | Skipping at 5 nM |
| 51 | H12A(-10+10) | UCU AUG UAA ACU GAA AAU UU | Skipping at 100 nM |
| 52 | H12A(+11+30) | UUC UGG AGA UCC AUU AAA AC | No skipping |

Antisense Oligonucleotides Directed at Exon 13

Antisense oligonucleotides directed at exon 13 were prepared and tested for their ability to induce exon skipping in human muscle cells using similar methods as described above.

H13A(+77+100) [SEQ ID NO:53] induced substantial exon 13 skipping when delivered into cells at a concentration of 5 nM. Table 11 below includes two other antisense molecules tested at a concentration range of 5, 25, 50, 100, 200 and 300 nM. These other antisense molecules were unable to induce exon skipping.

TABLE 11

| SEQ ID | Antisense Oligonucleotide name | Sequence | Ability to induce skipping |
|---|---|---|---|
| 53 | H13A(+77+100) | CAG CAG UUG CGU GAU CUC CAC UAG | Skipping at 5 nM |
| 54 | H13A(+55+75) | UUC AUC AAC UAC CAC CAC CAU | No skipping |
| 55 | H13D(+06-19) | CUA AGC AAA AUA AUC UGA CCU UAA G | No skipping |

Antisense Oligonucleotides Directed at Exon 14

Antisense oligonucleotides directed at exon 14 were prepared and tested for their ability to induce exon skipping in human muscle cells using similar methods as described above.

H14A(+37+64) [SEQ ID NO:56] induced weak exon 14 skipping when delivered into cells at a concentration of 100 nM. Table 12 below includes other antisense molecules tested at a concentration range of 5, 25, 50, 100, 200 and 300 nM. The other antisense molecules were unable to induce exon skipping at any of the concentrations tested.

TABLE 12

| SEQ ID | Antisense Oligonucleotide name | Sequence | Ability to induce skipping |
|---|---|---|---|
| 56 | H14A(+37+64) | CUU GUA AAA GAA CCC AGC GGU CUU CUG U | Skipping at 100 nM |
| 57 | H14A(+14+35) | CAU CUA CAG AUG UUU GCC CAU C | No skipping |
| 58 | H14A(+51+73) | GAA GGA UGU CUU GUA AAA GAA CC | No skipping |

TABLE 12-continued

| SEQ ID | Antisense Oligonucleotide name | Sequence | Ability to induce skipping |
|---|---|---|---|
| 59 | H14D(-02+18) | ACC UGU UCU UCA GUA AGA CG | No skipping |
| 60 | H14D(+14-10) | CAU GAC ACA CCU GUU CUU CAG UAA | No skipping |
| 61 | H14A(+61 +80) | CAU UUG AGA AGG AUG UCU UG | No skipping |
| 62 | H14A(-12+12) | AUC UCC CAA UAC CUG GAG AAG AGA | No skipping |

Antisense Oligonucleotides Directed at Exon 15

Antisense oligonucleotides directed at exon 15 were prepared and tested for their ability to induce exon skipping in human muscle cells using similar methods as described above.

Figure 9B:
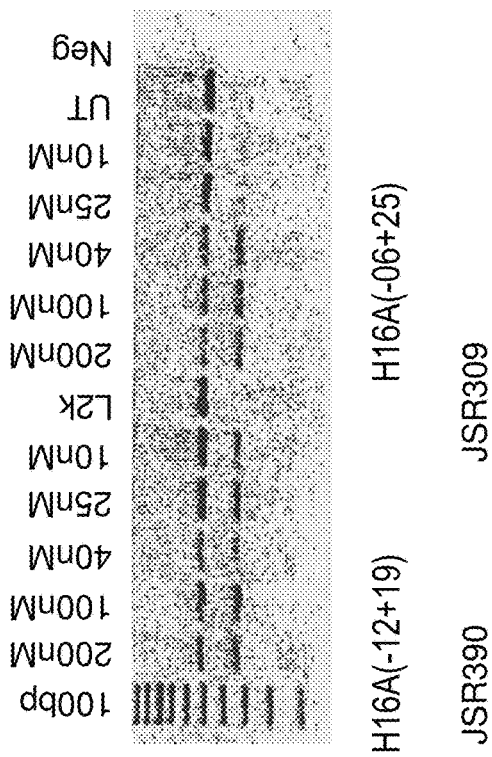
FIG. 9B Gel electrophoresis showing strong human exon 16 skipping using antisense molecules H16A(−12+19) and H16A(−06+25).
Figure 9A:
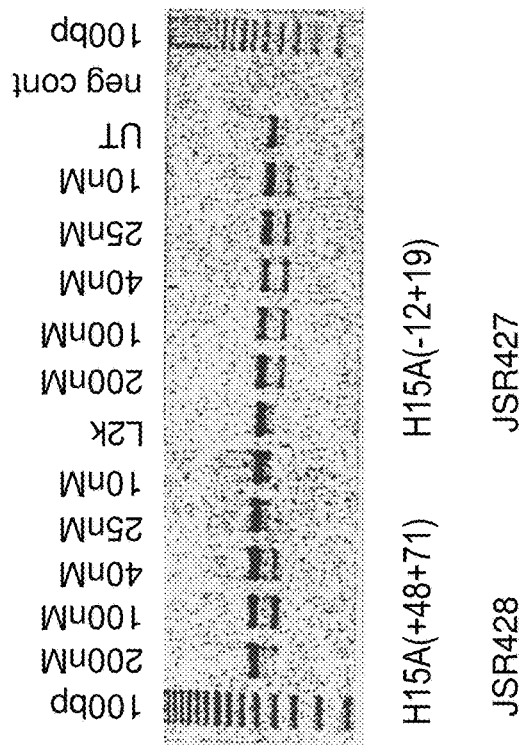
FIG. 9A Gel electrophoresis showing strong human exon 15 skipping using antisense molecules H15A(+48+71) and H15A(−12+19) directed at an exon 15 internal domain.

H15A(-12+19) [SEQ ID NO:63] and H15A(+48+71) [SEQ ID NO:64] induced substantial exon 15 skipping when delivered into cells at a concentration of 10 Nm, as shown in FIG. 9A. Table 13 below includes other antisense molecules tested at a concentration range of 5, 25, 50, 100, 200 and 300 Nm. These other antisense molecules were unable to induce exon skipping at any of the concentrations tested.

TABLE 13

| SEQ ID | Antisense Oligonucleotide name | Sequence | Ability to induce skipping |
|---|---|---|---|
| 63 | H15A(-12+19) | GCC AUG CAC UAA AAA GGC ACU GCA AGA CAU U | Skipping at 5 Nm |
| 64 | H15A(+48+71) | UCU UUA AAG CCA GUU GUG UGA AUC | Skipping at 5 Nm |
| 65 | H15A(+08+28) | UUU CUG AAA GCC AUG CAC UAA | No skipping |
| 63 | H15A(-12+19) | GCC AUG CAC UAA AAA GGC ACU GCA AGA CAU U | No skipping |
| 66 | H15D(+17-08) | GUA CAU ACG GCC AGU UUU UGA AGA C | No skipping |

Antisense Oligonucleotides Directed at Exon 16

Antisense oligonucleotides directed at exon 16 were prepared and tested for their ability to induce exon skipping in human muscle cells using similar methods as described above.

H16A(-12+19) [SEQ ID NO:67] and H16A(-06+25) [SEQ ID NO:68] induced substantial exon 16 skipping when delivered into cells at a concentration of 10 nM, as shown in FIG. 9B. Table 14 below includes other antisense molecules tested. H16A(-06+19) [SEQ ID NO:69] and H16A(+87+109) [SEQ ID NO:70] were tested at a concentration range of 5, 25, 50, 100, 200 and 300 nM. These two antisense molecules were able to induce exon skipping at 25 nM and 100 nM, respectively. Additional antisense molecules were tested at 100, 200 and 300 nM and did not result in any exon skipping.

TABLE 14

| SEQ ID | Antisense Oligonucleotide name | Sequence | Ability to induce skipping |
|---|---|---|---|
| 67 | H16A(-12+19) | CUA GAU CCG CUU UUA AAA CCU GUU AAA ACA A | Skipping at 5 nM |

TABLE 14-continued

| SEQ ID | Antisense Oligonucleotide name | Sequence | Ability to induce skipping |
|---|---|---|---|
| 68 | H16A(-06+25) | UCU UUU CUA GAU CCG CUU UUA AAA CCU GUU A | Skipping at 5 nM |
| 69 | H16A(-06+19) | CUA GAU CCG CUU UUA AAA CCU GUU A | Skipping at 25 nM |
| 70 | H16A(+87+109) | CCG UCU UCU GGG UCA CUG ACU UA | Skipping at 100 nM |
| 71 | H16A(-07+19) | CUA GAU CCG CUU UUA AAA CCU GUU AA | No skipping |
| 72 | H16A(-07+13) | CCG CUU UUA AAA CCU GUU AA | No skipping |
| 73 | H16A(+12+37) | UGG AUU GCU UUU UCU UUU CUA GAU CC | No skipping |
| 74 | H16A(+92+116) | CAU GCU UCC GUC UUC UGG GUC ACU G | No skipping |
| 75 | H16A(+45+67) | G AUC UUG UUU GAG UGA AUA CAG U | No skipping |
| 76 | H16A(+105+126) | GUU AUC CAG CCA UGC UUC CGU C | No skipping |
| 77 | H16D(+05-20) | UGA UAA UUG GUA UCA CUA ACC UGU G | No skipping |
| 78 | H16D(+12-11) | GUA UCA CUA ACC UGU GCU GUA C | No skipping |

Antisense Oligonucleotides Directed at Exon 19

Antisense oligonucleotides directed at exon 19 were prepared and tested for their ability to induce exon skipping in human muscle cells using similar methods as described above.

H19A(+35+65) [SEQ ID NO:79] induced substantial exon 19 skipping when delivered into cells at a concentration of 10 nM. This antisense molecule also showed very strong exon skipping at concentrations of 25, 50, 100, 300 and 600 nM.

Figure 10:
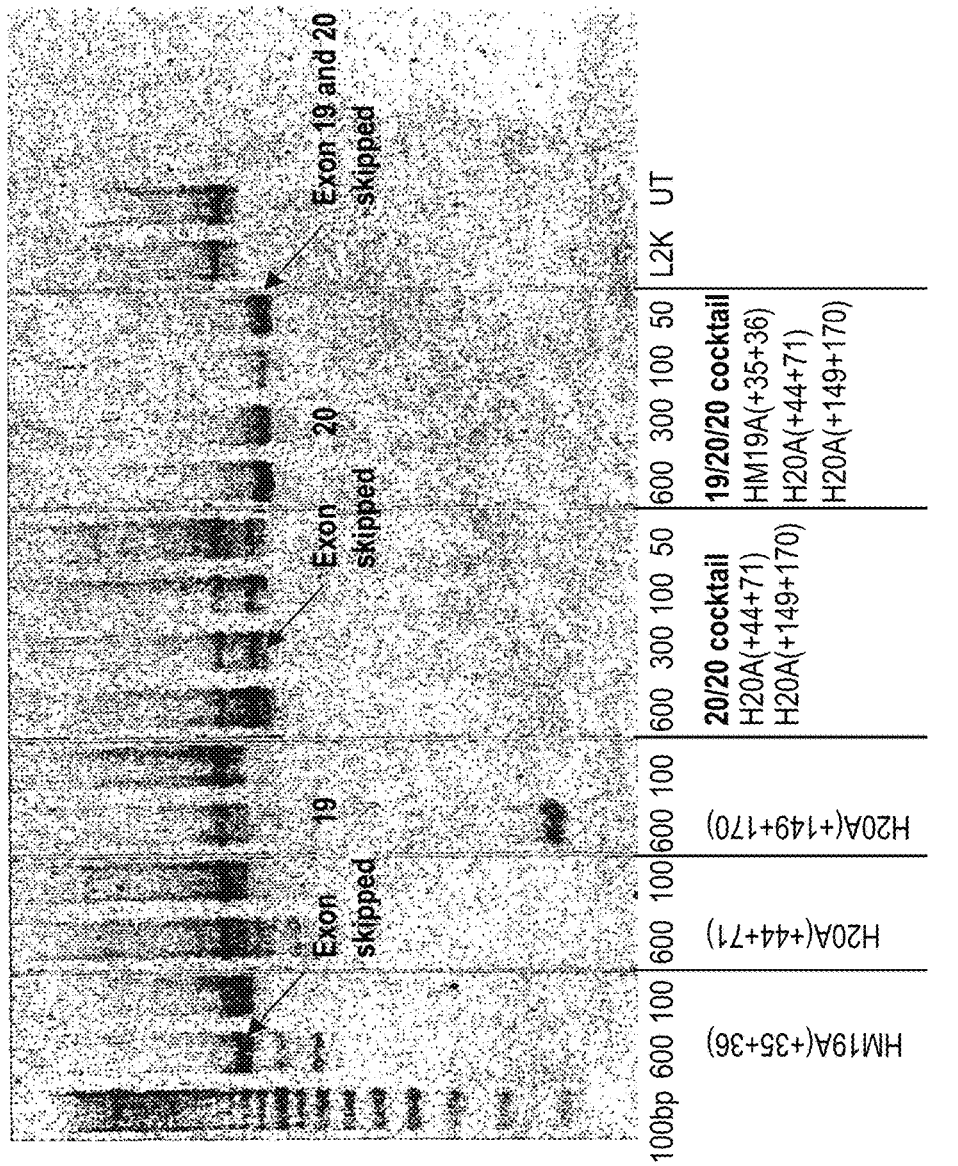
FIG. 10 Gel electrophoresis showing human exon 19/20 skipping using antisense molecules H20A(+44+71) and H20A(+149+170) directed at an exon 20 and a "cocktail" of antisense oligonucleotides H19A(+35+65, H20A(+44+71) and H20A(+149+170) directed at exons 19/20.

FIG. 10 illustrates exon 19 and 20 skipping using a "cocktail" of antisense oligonucleotides, as tested using gel electrophoresis. It is interesting to note that it was not easy to induce exon 20 skipping using single antisense oligonucleotides H20A(+44+71) [SEQ ID NO:81] or H20A(+149+170) [SEQ ID NO:82], as illustrated in sections 2 and 3 of the gel shown in FIG. 10. Whereas, a "cocktail" of antisense oligonucleotides was more efficient as can be seen in section 4 of FIG. 10 using a "cocktail" of antisense oligonucleotides H20A(+44+71) and H20A(+149+170). When the cocktail was used to target exon 19, skipping was even stronger (see section 5, FIG. 10).

Figure 11:
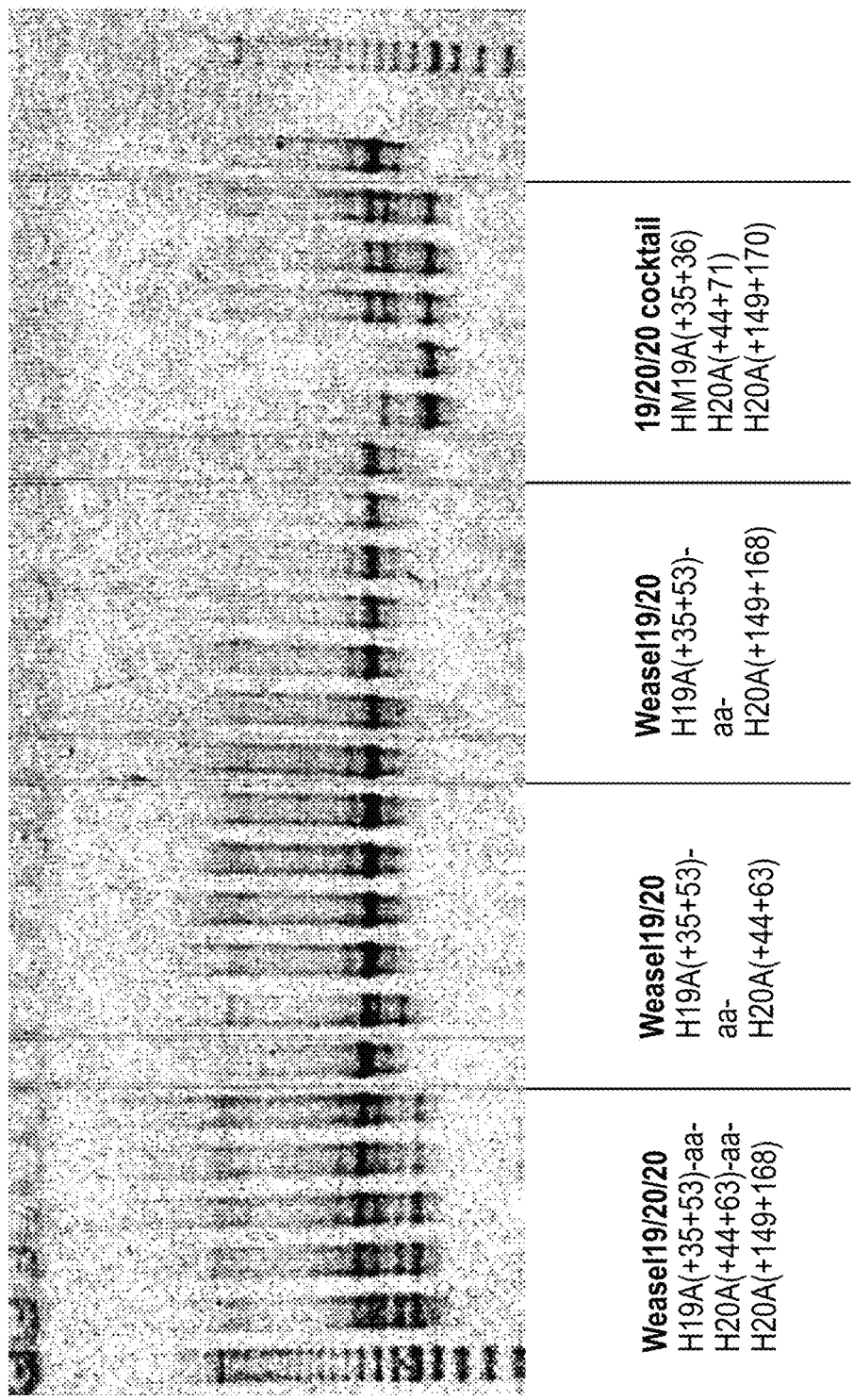
FIG. 11 Gel electrophoresis showing human exon 19/20 skipping using "weasels" directed at exons 19 and 20.

FIG. 11 illustrates gel electrophoresis results of exon 19/20 skipping using "weasels" The "weasels" were effective in skipping exons 19 and 20 at concentrations of 25, 50, 100, 300 and 600 nM. A further "weasel" sequence is shown in the last row of Table 3C. This compound should give good results.

Antisense Oligonucleotides Directed at Exon 20

Antisense oligonucleotides directed at exon 20 were prepared and tested for their ability to induce exon skipping in human muscle cells using similar methods as described above.

None of the antisense oligonucleotides tested induced exon 20 skipping when delivered into cells at a concentration of 10, 25, 50, 300 or 600 nM (see Table 15). Antisense molecules H20A(-11+17) [SEQ ID NO:86] and H20D(+08-20) [SEQ ID NO:87] are yet to be tested.

However, a combination or "cocktail" of H20A(+44+71) [SEQ ID NO: 81] and H20(+149+170) [SEQ ID NO:82] in a ratio of 1:1, exhibited very strong exon skipping at a concentration of 100 nM and 600 nM. Further, a combination of antisense molecules H19A(+35+65) [SEQ ID NO:79], H20A(+44+71) [SEQ ID NO:81] and H20A(+149+170) [SEQ ID NO:82] in a ratio of 2:1:1, induced very strong exon skipping at a concentration ranging from 10 nM to 600 nM.

TABLE 15

| SEQ ID | Antisense Oligonucleotide name | Sequence | Ability to induce skipping |
|---|---|---|---|
| 81 | H20A(+44+71) | CUG GCA GAA UUC GAU CCA CCG GCU GUU C | No skipping |
| 82 | H20A(+147+168) | CAG CAG UAG UUG UCA UCU GCU C | No skipping |
| 83 | H20A(+185+203) | UGA UGG GGU GGU GGG UUG G | No skipping |
| 84 | H20A(-08+17) | AUC UGC AUU AAC ACC CUC UAG AAA G | No skipping |

TABLE 15-continued

| SEQ ID | Antisense Oligonucleotide name | Sequence | Ability to induce skipping |
|---|---|---|---|
| 85 | H20A(+30+53) | CCG GCU GUU CAG UUG UUC UGA GGC | No skipping |
| 86 | H20A(-11+17) | AUC UGC AUU AAC ACC CUC UAG AAA GAA A | Not tested yet |
| 87 | H20D(+08-20) | GAA GGA GAA GAG AUU CUU ACC UUA CAA A | Not tested yet |
| 81 & 82 | H20A(+44+71) & H20A(+147+168) | CUG GCA GAA UUC GAU CCA CCG GCU GUU C CAG CAG UAG UUG UCA UCU GCU C | Very strong skipping |
| 80, 81 & 82 | H19A(+35+65); H20A(+44+71); H20A(+147+168) | GCC UGA GCU GAU CUG CUG GCA UCU UGC AGU U; CUG GCA GAA UUC GAU CCA CCG GCU GUU C; CAG CAG UAG UUG UCA UCU GCU C | Very strong skipping |

Antisense Oligonucleotides Directed at Exon 21

Antisense oligonucleotides directed at exon 21 were prepared and tested for their ability to induce exon skipping in human muscle cells using similar methods as described above.

H21A(+85+108) [SEQ ID NO:92] and H21A(+85+106) [SEQ ID NO:91] induced exon 21 skipping when delivered into cells at a concentration of 50 nM. Table 16 below includes other antisense molecules tested at a concentration range of 5, 25, 50, 100, 200 and 300 nM. These antisense molecules showed a variable ability to induce exon skipping

TABLE 16

| SEQ ID | Antisense Oligonucleotide name | Sequence | Ability to induce skipping |
|---|---|---|---|
| 90 | H21A(-06+16) | GCC GGU UGA CUU CAU CCU GUG C | Skips at 600 nM |
| 91 | H21A(+85+106) | CUG CAU CCA GGA ACA UGG GUC C | Skips at 50 nM |
| 92 | H21A(+85+108) | GUC UGC AUC CAG GAA CAU GGG UC | Skips at 50 nM |
| 93 | H21A(+08+31) | GUU GAA GAU CUG AUA GCC GGU UGA | Skips faintly to |
| 94 | H21D(+18-07) | UAC UUA CUG UCU GUA GCU CUU UCU | No skipping |

Antisense Oligonucleotides Directed at Exon 22

Antisense oligonucleotides directed at exon 22 were prepared and tested for their ability to induce exon skipping in human muscle cells using similar methods as described above.

Figure 12:
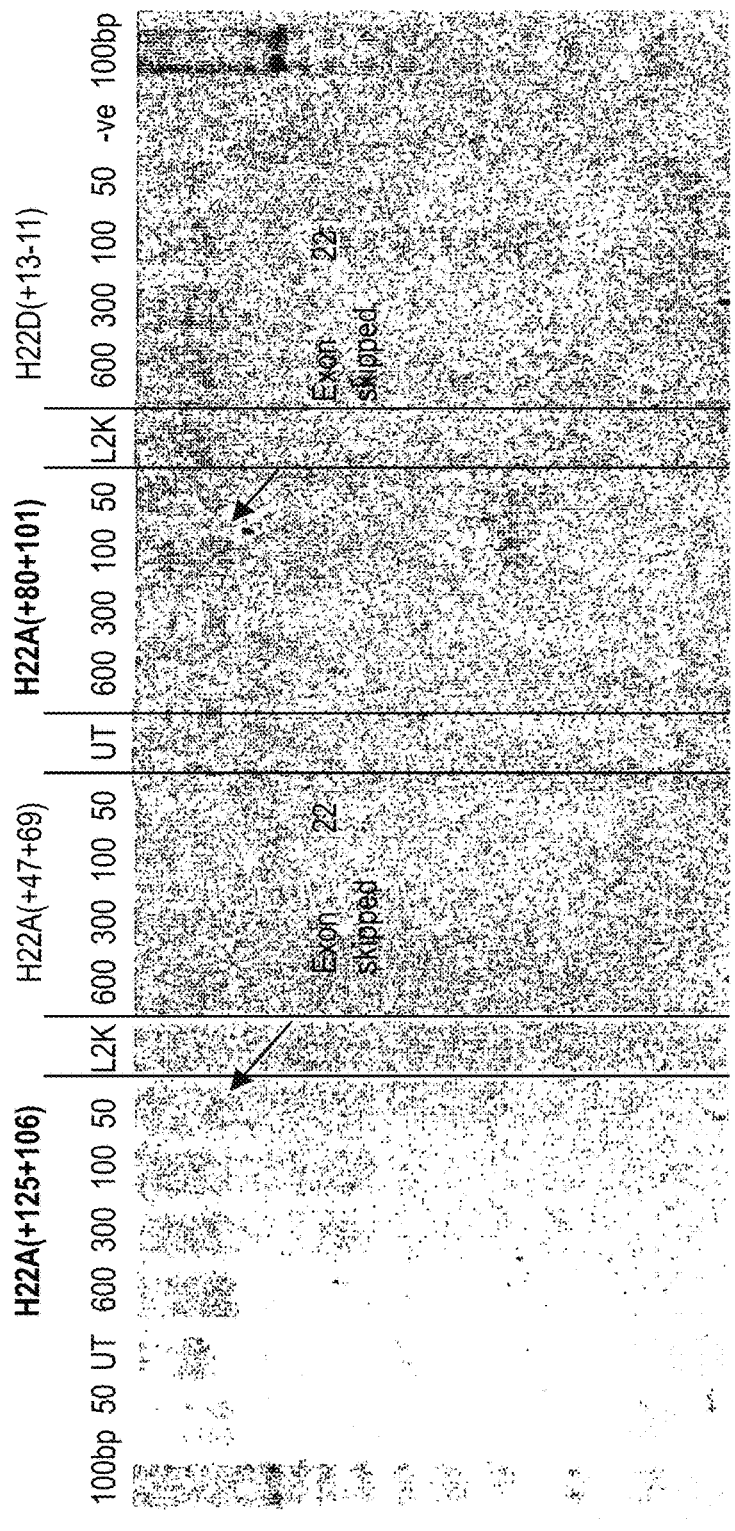
FIG. 12 Gel electrophoresis showing exon 22 skipping using antisense molecules H22A(+125+106), H22A(+47+69), H22A(+80+101) and H22D(+13-11) directed at exon 22.

FIG. 12 illustrates differing efficiencies of two antisense molecules directed at exon 22 acceptor splice site. H22A(+125+106) [SEQ ID NO:96] and H22A(+80+101) [SEQ ID NO: 98] induce strong exon 22 skipping from 50 nM to 600 nM concentration.

H22A(+125+146) [SEQ ID NO:96] and H22A(+80+101) [SEQ ID NO:98] induced exon 22 skipping when delivered into cells at a concentration of 50 nM. Table 17 below shows other antisense molecules tested at a concentration range of 50, 100, 300 and 600 nM. These antisense molecules showed a variable ability to induce exon skipping.

TABLE 17

| SEQ ID | Antisense oligonucleotide name | Sequence | Ability to induce skipping |
|---|---|---|---|
| 95 | H22A(+22+45) | CAC UCA UGG UCU CCU GAU AGC GCA | No skipping |
| 96 | H22A(+125+146) | CUG CAA UUC CCC GAG UCU CUG C | Skipping to 50 nM |
| 97 | H22A(+47+69) | ACU GCU GGA CCC AUG UCC UGA UG | Skipping to 300 nM |
| 98 | H22A(+80+101) | CUA AGU UGA GGU AUG GAG AGU | Skipping to 50 nM |
| 99 | H22D(+13-11) | UAU UCA CAG ACC UGC AAU UCC CC | No skipping |

Antisense Oligonucleotides Directed at Exon 23

Antisense oligonucleotides directed at exon 23 were prepared and tested for their ability to induce exon skipping in human muscle cells using similar methods as described above.

Table 18 below shows antisense molecules tested at a concentration range of 25, 50, 100, 300 and 600 nM. These antisense molecules showed no ability to induce exon skipping or are yet to be tested.

TABLE 18

| SEQ ID | Antisense oligonucleotide name | Sequence | Ability to induce skipping |
|---|---|---|---|
| 100 | H23A(+34+59) | ACA GUG GUG CUG AGA UAG UAU AGG CC | No skipping |
| 101 | H23A(+18+39) | UAG GCC ACU UUG UUG CUC UUG C | No Skipping |
| 102 | H23A(+72+90) | UUC AGA GGG CGC UUU CUU C | No Skipping |

Antisense Oligonucleotides Directed at Exon 24

Antisense oligonucleotides directed at exon 24 were prepared using similar methods as described above. Table 19 below outlines the antisense oligonucleotides directed at exon 24 that are yet to be tested for their ability to induce exon 24 skipping.

TABLE 19

| SEQ ID | Antisense oligonucleotide name | Sequence | Ability to induce skipping |
|---|---|---|---|
| 103 | H24A(+48+70) | GGG CAG GCC AUU CCU CCU UCA GA | Needs testing |
| 104 | H24A(-02+22) | UCU UCA GGG UUU GUA UGU GAU UCU | Needs testing |

Antisense Oligonucleotides Directed at Exon 25

Antisense oligonucleotides directed at exon 25 were prepared using similar methods as described above. Table 20 below shows the antisense oligonucleotides directed at exon 25 that are yet to be tested for their ability to induce exon 25 skipping.

TABLE 20

| SEQ ID | Antisense oligonucleotide name | Sequence | Ability to induce skipping |
|---|---|---|---|
| 105 | H25A(+9+36) | CUG GGC UGA AUU GUC UGA AUA UCA CUG | Needs testing |
| 106 | H25A(+131+156) | CUG UUG GCA CAU GUG AUC CCA CUG AG | Needs testing |
| 107 | H25D(+16-08) | GUC UAU ACC UGU UGG CAC AUG UGA | Needs testing |

Antisense Oligonucleotides Directed at Exon 26

Antisense oligonucleotides directed at exon 26 were prepared using similar methods as described above. Table 21 below outlines the antisense oligonucleotides directed at exon 26 that are yet to be tested for their ability to induce exon 26 skipping.

TABLE 21

| SEQ ID | Antisense oligonucleotide name | Sequence | Ability to induce skipping |
|---|---|---|---|
| 108 | H26A(+132+156) | UGC UUU CUG UAA UUC AUC UGG AGU U | Needs testing |
| 109 | H26A(-07+19) | CCU CCU UUC UGG CAU AGA CCU UCC AC | Needs testing |
| 110 | H26A(+68+92) | UGU GUC AUC CAU UCG UGC AUC UCU G | Faint skipping at 600 nM |

Antisense Oligonucleotides Directed at Exon 27

Antisense oligonucleotides directed at exon 27 were prepared using similar methods as described above. Table 22 below outlines the antisense oligonucleotides directed at exon 27 that are yet to be tested for their ability to induce exon 27 skipping.

TABLE 22

| SEQ ID | Antisense oligonucleotide name | Sequence | Ability to induce skipping |
|---|---|---|---|
| 111 | H27A(+82+106) | UUA AGG CCU CUU GUG CUA CAG GUG G | Needs testing |
| 112 | H27A(−4+19) | GGG CCU CUU CUU UAG CUC UCU GA | Faint skipping at 600 and 300 nM |
| 113 | H27D(+19−03) | GAC UUC CAA AGU CUU GCA UUU C | v. strong skipping at 600 and 300 nM |

Antisense Oligonucleotides Directed at Exon 28

Antisense oligonucleotides directed at exon 28 were prepared using similar methods as described above. Table 23 below outlines the antisense oligonucleotides directed at exon 28 that are yet to be tested for their ability to induce exon 28 skipping.

TABLE 23

| SEQ ID | Antisense oligonucleotide name | Sequence | Ability to induce skipping |
|---|---|---|---|
| 114 | H28A(−05+19) | GCC AAC AUG CCC AAA CUU CCU AAG | v. strong skipping at 600 and 300 nM |
| 115 | H28A(+99+124) | CAG AGA UUU CCU CAG CUC CGC CAG GA | Needs testing |
| 116 | H28D(+16−05) | CUU ACA UCU AGC ACC UCA GAG | v. strong skipping at 600 and 300 nM |

Antisense Oligonucleotides Directed at Exon 29

Antisense oligonucleotides directed at exon 29 were prepared using similar methods as described above. Table 24 below outlines the antisense oligonucleotides directed at exon 29 that are yet to be tested for their ability to induce exon 29 skipping.

TABLE 24

| SEQ ID | Antisense oligonucleotide name | Sequence | Ability to induce skipping |
|---|---|---|---|
| 117 | H29A(+57+81) | UCC GCC AUC UGU UAG GGU CUG UGC C | Needs testing |
| 118 | H29A(+18+42) | AUU UGG GUU AUC CUC UGA AUG UCG C | v. strong skipping at 600 and 300 nM |
| 119 | H29D(+17−05) | CAU ACC UCU UCA UGU AGU UCC C | v. strong skipping at 600 and 300 nM |

Antisense Oligonucleotides Directed at Exon 30

Antisense oligonucleotides directed at exon 30 were prepared using similar methods as described above. Table 25 below outlines the antisense oligonucleotides directed at exon 30 that are yet to be tested for their ability to induce exon 30 skipping.

TABLE 25

| SEQ ID | Antisense oligonucleotide name | Sequence | Ability to induce skipping |
|---|---|---|---|
| 120 | H30A (+122+147) | CAU UUG AGC UGC GUC CAC CUU GUC UG | Needs testing |
| 121 | H30A (+25+50) | UCC UGG GCA GAC UGG AUG CUC UGU UC | Very strong skipping at 600 and 300 nM. |
| 122 | H30D (+19−04) | UUG CCU GGG CUU CCU GAG GCA UU | Very strong skipping at 600 and 300 nM. |

Antisense Oligonucleotides Directed at Exon 31

Antisense oligonucleotides directed at exon 31 were prepared and tested for their ability to induce exon skipping in human muscle cells using similar methods as described above.

Figure 13:
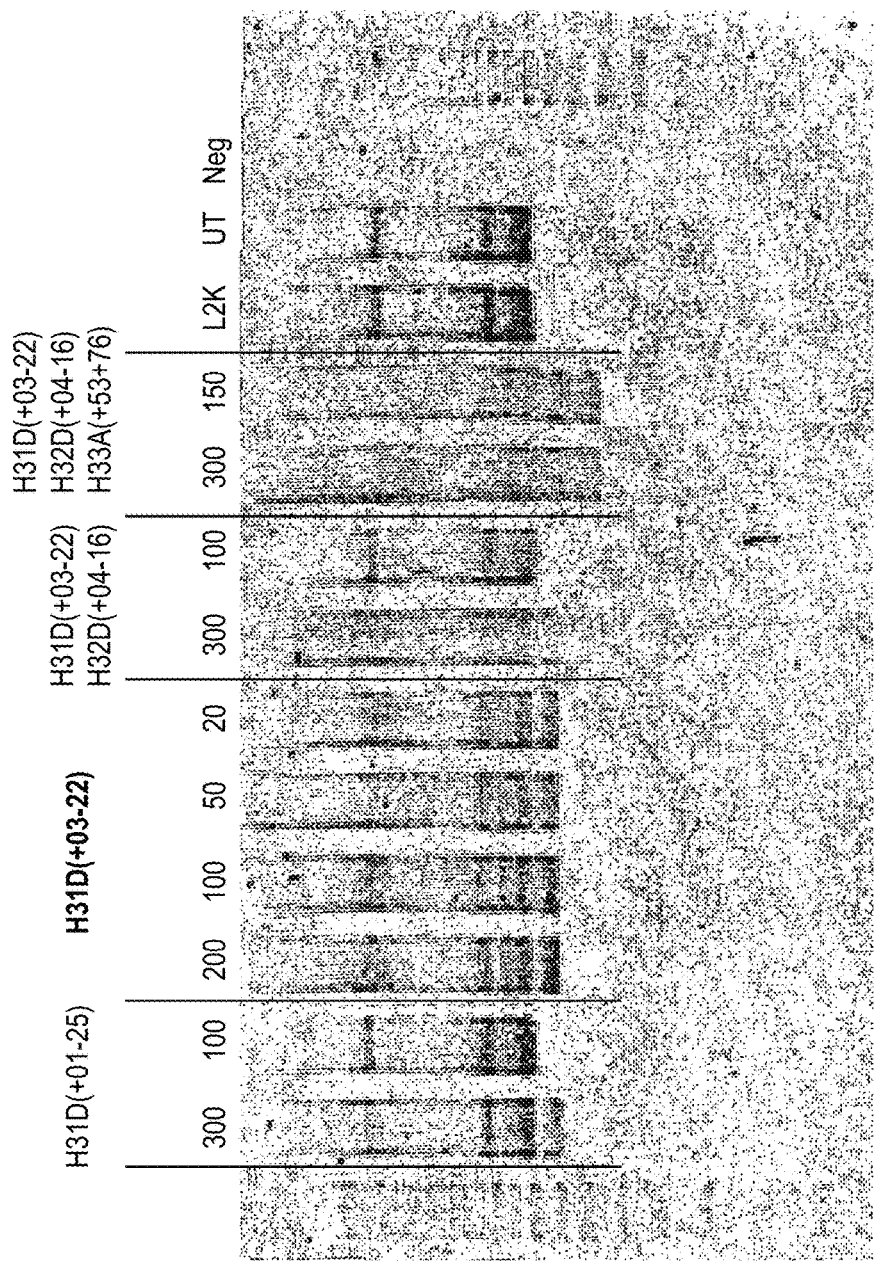
FIG. 13 Gel electrophoresis showing exon 31 skipping using antisense molecules H31D(+01−25) and H31D(+03−22); and a "cocktail" of antisense molecules directed at exon 31.

FIG. 13 illustrates differing efficiencies of two antisense molecules directed at exon 31 acceptor splice site and a "cocktail" of exon 31 antisense oligonucleotides at varying concentrations. H31D(+03−22) [SEQ ID NO:124] substantially induced exon 31 skipping when delivered into cells at a concentration of 20 nM. Table 26 below also includes other antisense molecules tested at a concentration of 100 and 300 nM. These antisense molecules showed a variable ability to induce exon skipping.

TABLE 26

| SEQ ID | Antisense oligonucleotide name | Sequence | Ability to induce skipping |
|---|---|---|---|
| 123 | H31D (+06-18) | UUC UGA AAU AAC AUA UAC CUG UGC | Skipping to 300 nM |
| 124 | H31D (+03-22) | UAG UUU CUG AAA UAA CAU AUA CCU G | Skipping to 20 nM |
| 125 | H31A (+05+25) | GAC UUG UCA AAU CAG AUU GGA | No skipping |
| 126 | H31D (+04-20) | GUU UCU GAA AUA ACA UAU ACC UGU | Skipping to 300 nM |

Antisense Oligonucleotides Directed at Exon 32

Antisense oligonucleotides directed at exon 32 were prepared and tested for their ability to induce exon skipping in human muscle cells using similar methods as described above.

H32D(+04−16) [SEQ ID NO:127] and H32A(+49+73) [SEQ ID NO:130] induced exon 32 skipping when delivered into cells at a concentration of 300 nM. Table 27 below also shows other antisense molecules tested at a concentration of 100 and 300 nM. These antisense molecules did not show an ability to induce exon skipping.

TABLE 27

| SEQ ID | Antisense oligonucleotide name | Sequence | Ability to induce skipping |
|---|---|---|---|
| 127 | H32D (+04-16) | CAC CAG AAA UAC AUA CCA CA | Skipping to 300 nM |
| 128 | H32A (+151+170) | CAA UGA UUU AGC UGU GAC UG | No skipping |
| 129 | H32A (+10+32) | CGA AAC UUC AUG GAG ACA UCU UG | No skipping |
| 130 | H32A (+49+73) | CUU GUA GAC GCU GCU CAA AAU UGG C | Skipping to 300 nM |

Antisense Oligonucleotides Directed at Exon 33

Antisense oligonucleotides directed at exon 33 were prepared and tested for their ability to induce exon skipping in human muscle cells using similar methods as described above.

Figure 14:
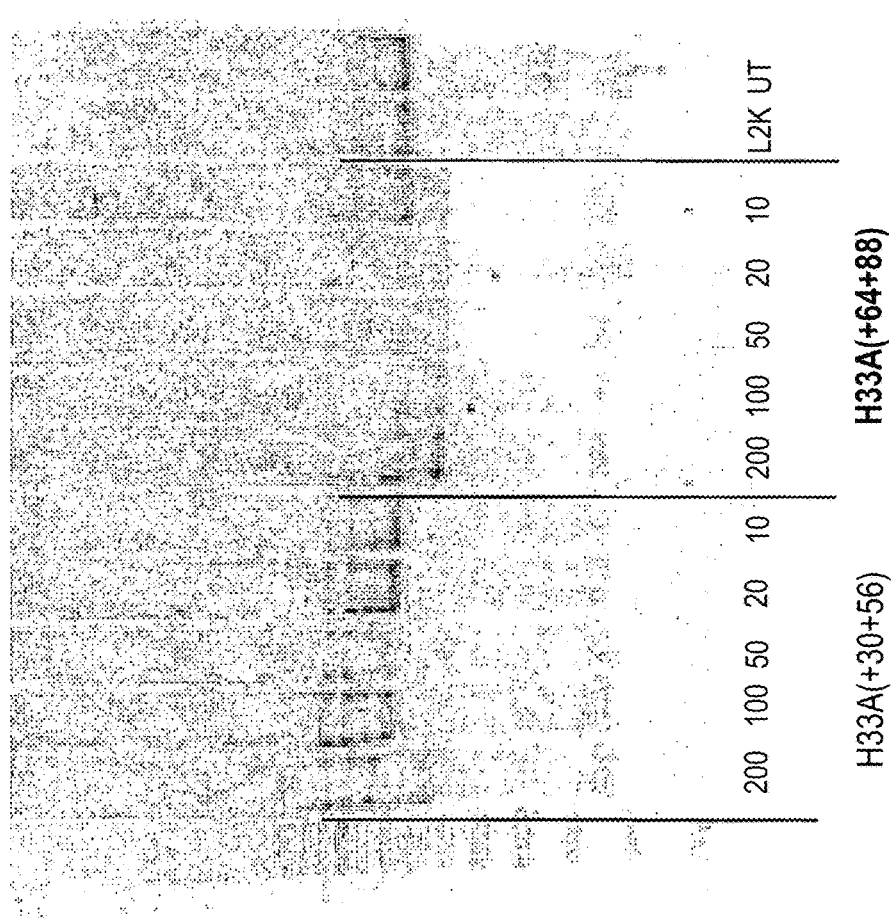
FIG. 14 Gel electrophoresis showing exon 33 skipping using antisense molecules H33A(+30+56) and H33A(+64+88) directed at exon 33.

FIG. 14 shows differing efficiencies of two antisense molecules directed at exon 33 acceptor splice site. H33A(+64+88) [SEQ ID NO:134] substantially induced exon 33 skipping when delivered into cells at a concentration of 10 nM. Table 28 below includes other antisense molecules tested at a concentration of 100, 200 and 300 nM. These antisense molecules showed a variable ability to induce exon skipping.

TABLE 28

| SEQ ID | Antisense oligonucleotide name | Sequence | Ability to induce skipping |
|---|---|---|---|
| 131 | H33D (+09−11) | CAU GCA CAC ACC UUU GCU CC | No skipping |
| 132 | H33A (+53+76) | UCU GUA CAA UCU GAC GUC CAG UCU | Skipping to 200 nM |
| 133 | H33A (+30+56) | GUG UUU AUC ACC AUU UCC ACU UCA GAC | Skipping to 200 nM |
| 134 | H33A (+64+88) | GCG UCU GCU UUU UCU GUA CAA UCU G | Skipping to 10 nM |

Antisense Oligonucleotides Directed at Exon 34

Antisense oligonucleotides directed at exon 34 were prepared and tested for their ability to induce exon skipping in human muscle cells using similar methods as described above.

Table 29 below includes antisense molecules tested at a concentration of 100 and 300 nM. These antisense molecules showed a variable ability to induce exon skipping.

TABLE 29

| SEQ ID | Antisense oligonucleotide name | Sequence | Ability to induce skipping |
|---|---|---|---|
| 135 | H34A (+83+104) | UCC AUA UCU GUA GCU GGC AGC C | No skipping |
| 136 | H34A (+143+165) | CCA GGC AAC UUC AGA AUC CAA AU | No skipping |
| 137 | H34A (−20+10) | UUU CUG UUA CCU GAA AAG AAU UAU AAU GAA | Not tested |
| 138 | H34A (+46+70) | CAU UCA UUU CCU UUC GCA UCU UAC G | Skipping to 300 nM |
| 139 | H34A (+95+120) | UGA UCU CUU UGU CAA UUC CAU AUC UG | Skipping to 300 nM |
| 140 | H34D (+10−20) | UUC AGU GAU AUA GGU UUU ACC UUU CCC CAG | Not tested |
| 141 | H34A (+72+96) | CUG UAG CUG CCA GCC AUU CUG UCA AG | No skipping |

Antisense Oligonucleotides Directed at Exon 35

Antisense oligonucleotides directed at exon 35 were prepared and tested for their ability to induce exon skipping in human muscle cells using similar methods as described above.

Figure 15:
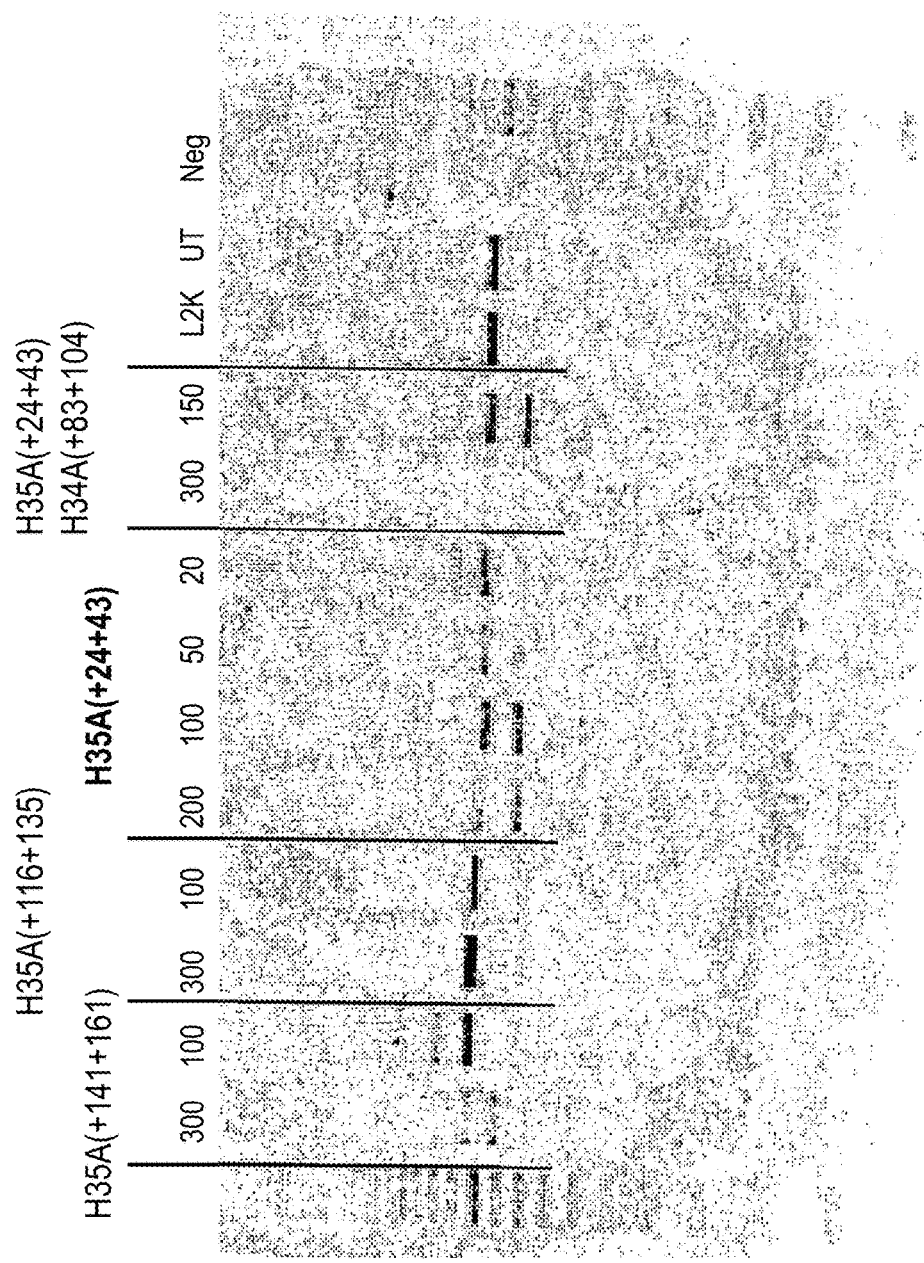
FIG. 15 Gel electrophoresis showing exon 35 skipping using antisense molecules H35A(+141+161), H35A(+116+135), and H35A(+24+43) and a "cocktail of two antisense molecules, directed at exon 35.

FIG. 15 shows differing efficiencies of antisense molecules directed at exon 35 acceptor splice site. H35A(+24+43) [SEQ ID NO:144] substantially induced exon 35 skipping when delivered into cells at a concentration of 20 nM. Table 30 below also includes other antisense molecules tested at a concentration of 100 and 300 nM. These antisense molecules showed no ability to induce exon skipping.

TABLE 30

| SEQ ID | Antisense oligonucleotide name | Sequence | Ability to induce skipping |
|---|---|---|---|
| 142 | H35A (+141+161) | UCU UCU GCU CGG GAG GUG ACA | Skipping to 20 nM |
| 143 | H35A (+116+135) | CCA GUU ACU AUU CAG AAG AC | No skipping |
| 144 | H35A (+24+43) | UCU UCA GGU GCA CCU UCU GU | No skipping |

Antisense Oligonucleotides Directed at Exon 36

Antisense oligonucleotides directed at exon 36 were prepared and tested for their ability to induce exon skipping in human muscle cells using similar methods as described above.

Figure 16:
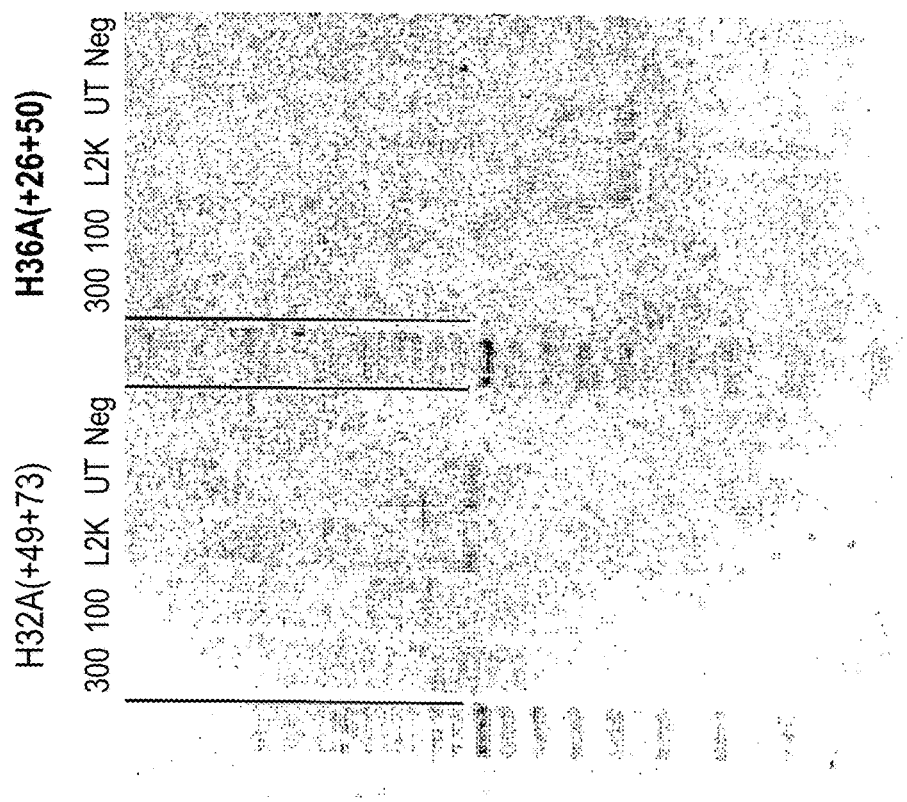
FIG. 16 Gel electrophoresis showing exon 36 skipping using antisense molecules H32A(+49+73) and H36A(+26+50) directed at exon 36.

Antisense molecule H36A(+26+50) [SEQ ID NO:145] induced exon 36 skipping when delivered into cells at a concentration of 300 nM, as shown in FIG. 16.

Antisense Oligonucleotides Directed at Exon 37

Antisense oligonucleotides directed at exon 37 were prepared and tested for their ability to induce exon skipping in human muscle cells using similar methods as described above.

Figure 17:
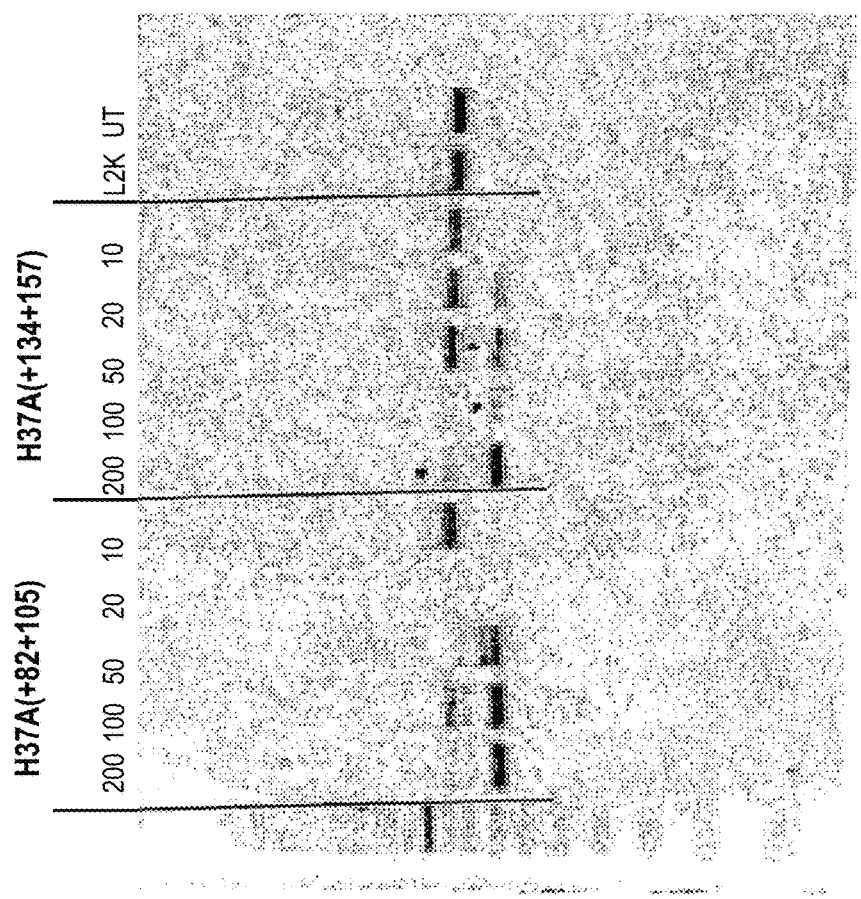
FIG. 17 Gel electrophoresis showing exon 37 skipping using antisense molecules H37A(+82+105) and H37A(+134+157) directed at exon 37.

FIG. 17 shows differing efficiencies of two antisense molecules directed at exon 37 acceptor splice site. H37A(+82+105) [SEQ ID NO:148] and H37A(+134+157) [SEQ ID NO:149] substantially induced exon 37 skipping when delivered into cells at a concentration of 10 nM. Table 31 below shows the antisense molecules tested.

TABLE 31

| SEQ ID | Antisense oligonucleotide name | Sequence | Ability to induce skipping |
|---|---|---|---|
| 147 | H37A (+26+50) | CGU GUA GAG UCC ACC UUU GGG CGU A | No skipping |
| 148 | H37A (+82+105) | UAC UAA UUU CCU GCA GUG GUC ACC | Skipping to 10 nM |
| 149 | H37A (+134+157) | UUC UGU GUG AAA UGG CUG CAA AUC | Skipping to 10 nM |

Antisense Oligonucleotides Directed at Exon 38

Antisense oligonucleotides directed at exon 38 were prepared and tested for their ability to induce exon skipping in human muscle cells using similar methods as described above.

Figure 18:
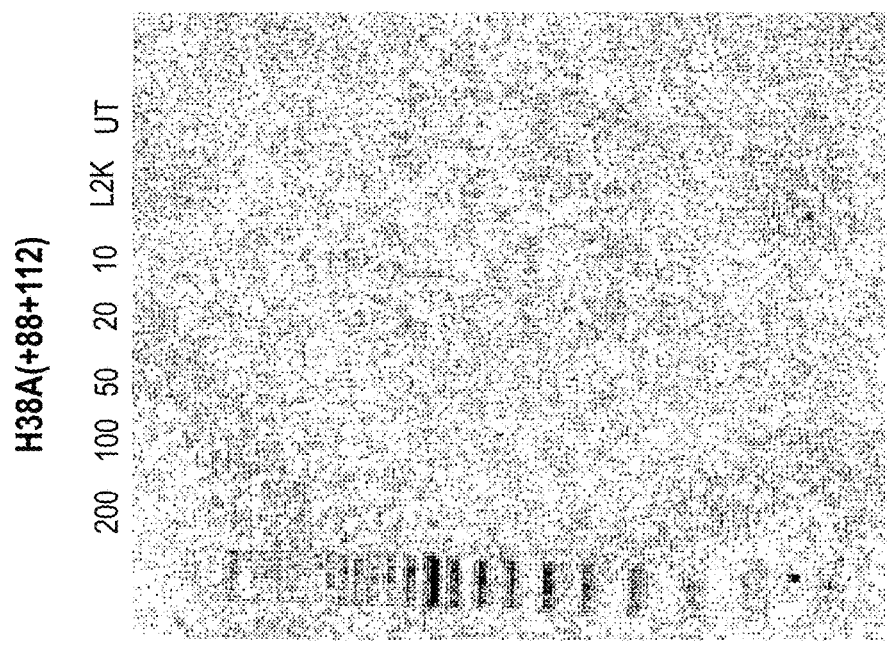
FIG. 18 Gel electrophoresis showing exon 38 skipping using antisense molecule H38A(+88+112) directed at exon 38.

FIG. 18 illustrates antisense molecule H38A(+88+112) [SEQ ID NO:152], directed at exon 38 acceptor splice site. H38A(+88+112) substantially induced exon 38 skipping when delivered into cells at a concentration of 10 nM. Table 32 below shows the antisense molecules tested and their ability to induce exon skipping.

TABLE 32

| Antisense SEQ ID | oligonucleotide name | Sequence | Ability to induce skipping |
|---|---|---|---|
| 150 | H38A (-01+19) | CCU UCA AAG GAA UGG AGG CC | No skipping |
| 151 | H38A (+59+83) | UGC UGA AUU UCA GCC UCC AGU GGU U | Skipping to 10 nM |
| 152 | H38A (+88+112) | UGA AGU CUU CCU CUU UCA GAU UCA C | Skipping to 10 nM |

Antisense Oligonucleotides Directed at Exon 39

Antisense oligonucleotides directed at exon 39 were prepared and tested for their ability to induce exon skipping in human muscle cells using similar methods as described above.

H39A(+62+85) [SEQ ID NO:153] induced exon 39 skipping when delivered into cells at a concentration of 100 nM. Table 33 below shows the antisense molecules tested and their ability to induce exon skipping.

TABLE 33

| SEQ ID | Antisense oligonucleotide name | Sequence | Ability to induce skipping |
|---|---|---|---|
| 153 | H39A (+62+85) | CUG GCU UUC UCU CAU CUG UGA UUC | Skipping to 100 nM |
| 154 | H39A (+39+58) | GUU GUA AGU UGU CUC CUC UU | No skipping |
| 155 | H39A (+102+121) | UUG UCU GUA ACA GCU GCU GU | No skipping |
| 156 | H39D (+10-10) | GCU CUA AUA CCU UGA GAG CA | Skipping to 300 nM |

Antisense Oligonucleotides Directed at Exon 40

Antisense oligonucleotides directed at exon 40 were prepared and tested for their ability to induce exon skipping in human muscle cells using similar methods as described above.

Figure 19:
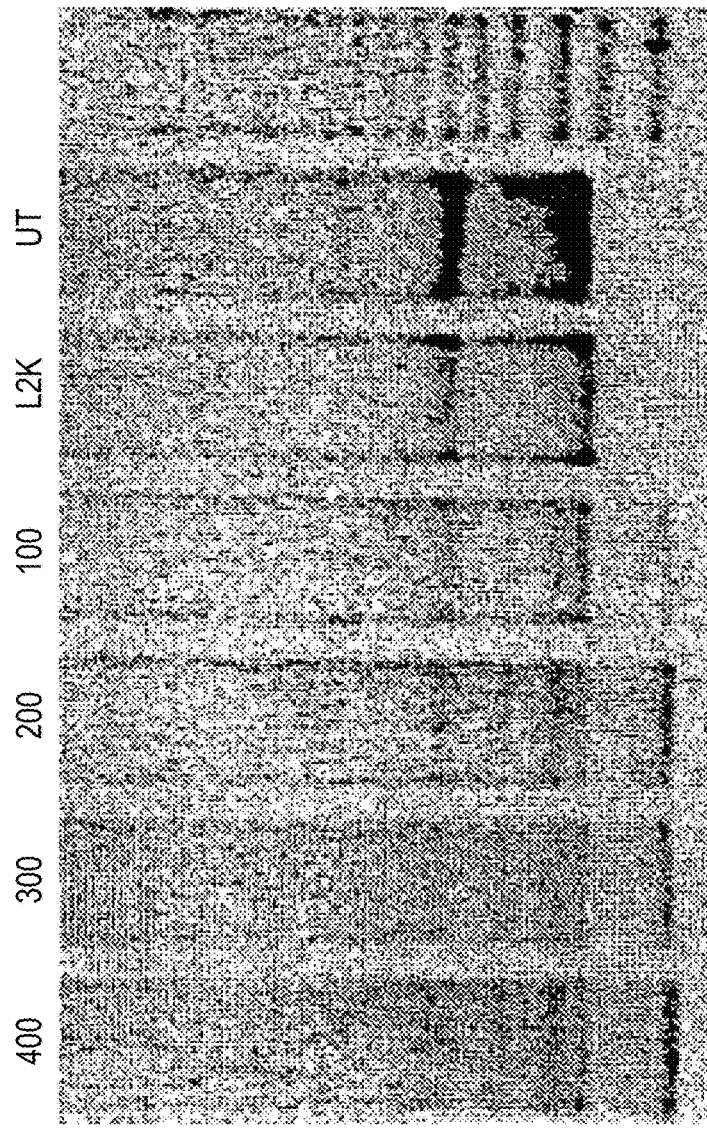
FIG. 19 Gel electrophoresis showing exon 40 skipping using antisense molecule H40A(−05+17) directed at exon 40.

FIG. 19 illustrates antisense molecule H40A(-05+17) [SEQ ID NO:157] directed at exon 40 acceptor splice site. H40A(-05+17) and H40A(+129+153) [SEQ ID NO:158] both substantially induced exon 40 skipping when delivered into cells at a concentration of 5 nM.

Antisense Oligonucleotides Directed at Exon 42

Antisense oligonucleotides directed at exon 42 were prepared and tested for their ability to induce exon skipping in human muscle cells using similar methods as described above.

Figure 20:
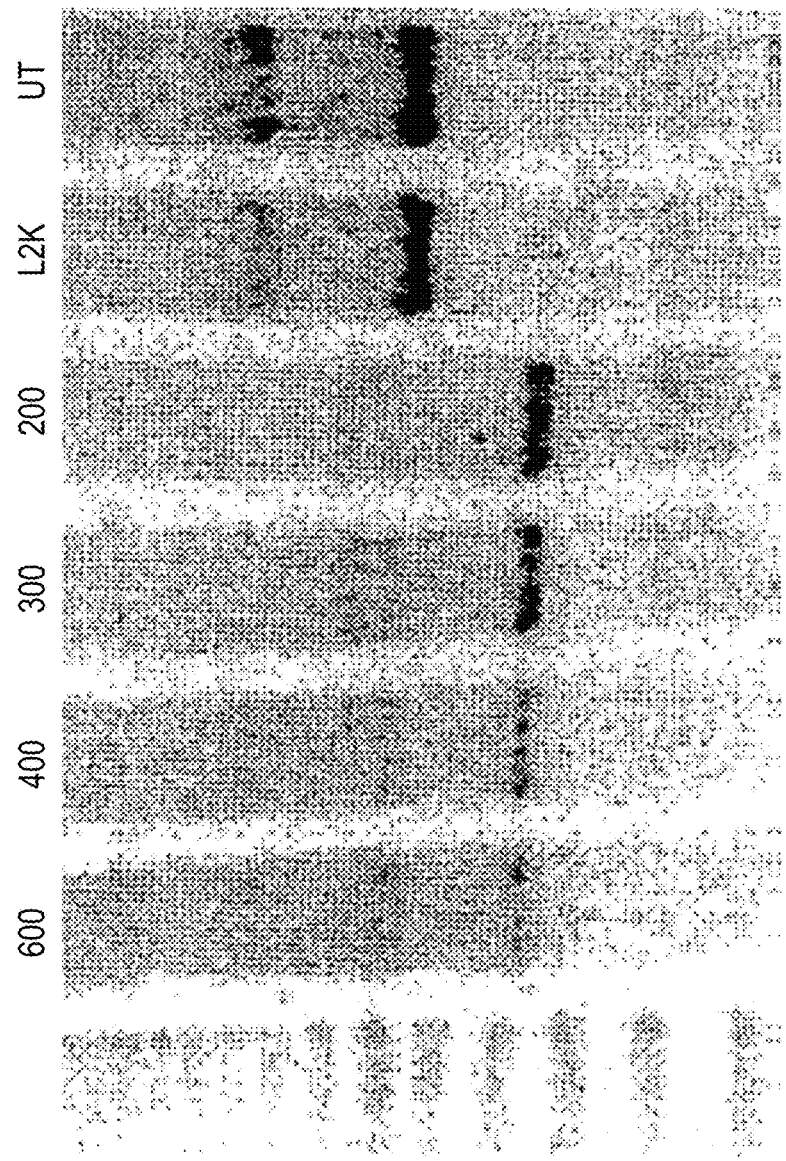
FIG. 20 Gel electrophoresis showing exon 42 skipping using antisense molecule H42A(−04+23) directed at exon 42.

FIG. 20 illustrates antisense molecule H42A(-04+23) [SEQ ID NO:159], directed at exon 42 acceptor splice site. H42A(-4+23) and H42D(+19-02) [SEQ ID NO:161] both induced exon 42 skipping when delivered into cells at a concentration of 5 nM. Table 34 below shows the antisense molecules tested and their ability to induce exon 42 skipping.

TABLE 34

| SEQ ID | Antisense afigonucleotide name | Sequence | Ability to induce skipping |
|---|---|---|---|
| 159 | H42A (-4+23) | AUC GUU UCU UCA CGG ACA GUG UGG UGC | Skipping to 5 nM |
| 160 | H42A (+86+109) | GGG CUU GUG AGA CAU GAG UGA UUU | Skipping to 100 nM |
| 161 | H42D (+19-02) | A CCU UCA GAG GAC UCC UCU UGC | Skipping to 5 nM |

Antisense Oligonucleotides Directed at Exon 43

Antisense oligonucleotides directed at exon 43 were prepared and tested for their ability to induce exon skipping in human muscle cells using similar methods as described above.

H43A(+101+120) [SEQ ID NO:163] induced exon 43 skipping when delivered into cells at a concentration of 25 nM. Table 35 below includes the antisense molecules tested and their ability to induce exon 43 skipping.

Antisense Oligonucleotides Directed at Exon 47

Antisense oligonucleotides directed at exon 47 were prepared and tested for their ability to induce exon skipping in human muscle cells using similar methods as described above.

H47A(+76+100) [SEQ ID NO:170] and H47A(−09+12) [SEQ ID NO:172] both induced exon 47 skipping when delivered into cells at a concentration of 200 nM. H47D(+25-02) [SEQ ID NO: 171] is yet to be prepared and tested.

TABLE 35

| SEQ ID | Antisense oligonucleotide name | Sequence | Ability to induce skipping |
|---|---|---|---|
| 162 | H43D (+10-15) | UAU GUG UUA CCU ACC CUU GUC GGU C | Skipping to 100 nM |
| 163 | H43A (+101+120) | GGA GAG AGC UUC CUG UAG CU | Skipping to 25 nM |
| 164 | H43A (+78+100) | UCA CCC UUU CCA CAG GCG UUG CA | Skipping to 200 nM |

Antisense Oligonucleotides Directed at Exon 44

Antisense oligonucleotides directed at exon 44 were prepared using similar methods as described above. Testing for the ability of these antisense molecules to induce exon 44 skipping is still in progress. The antisense molecules under review are shown as SEQ ID Nos: 165 to 167 in Table 1A.

Antisense Oligonucleotides Directed at Exon 45

Antisense oligonucleotides directed at exon 45 were prepared using similar methods as described above. Testing for the ability of these antisense molecules to induce exon 45 skipping is still in progress. The antisense molecules under review are shown as SEQ ID Nos: 207 to 211 in Table 1A.

Antisense Oligonucleotides Directed at Exon 46

Antisense oligonucleotides directed at exon 46 were prepared and tested for their ability to induce exon skipping in human muscle cells using similar methods as described above.

Figure 21:
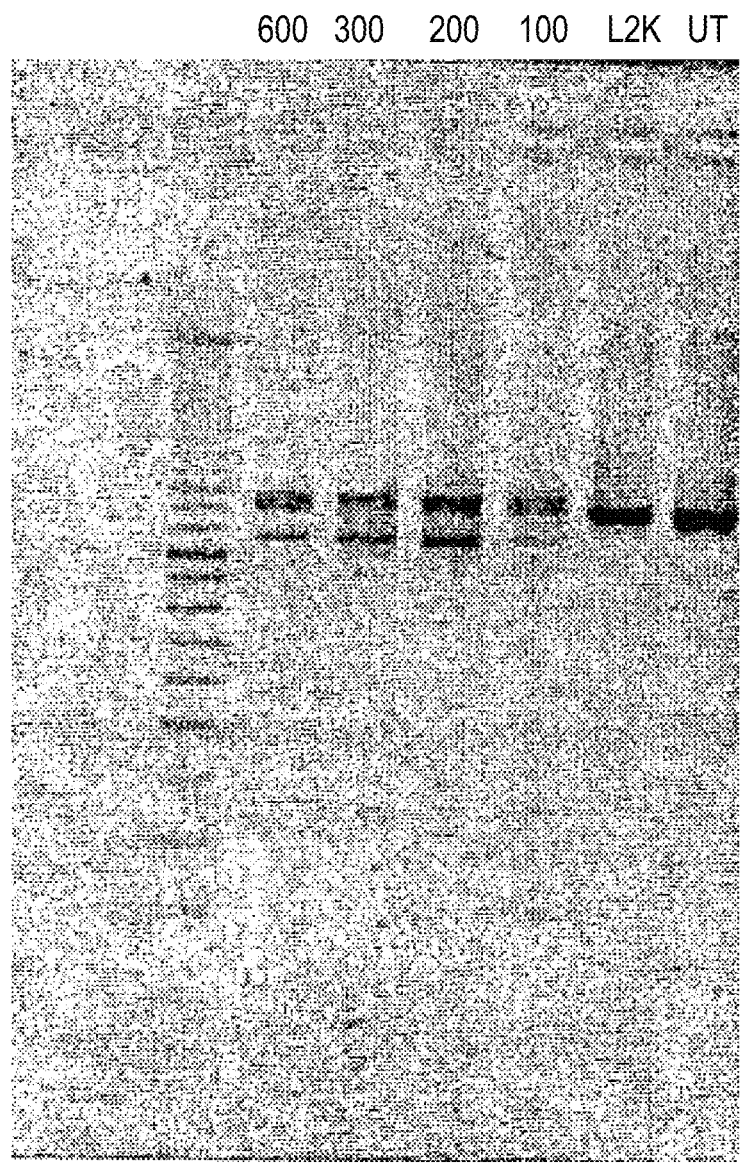
FIG. 21 Gel electrophoresis showing exon 46 skipping using antisense molecule H46A(+86+115) directed a# exon 46

FIG. 21 illustrates the efficiency of one antisense molecule directed at exon 46 acceptor splice site. Antisense oligonucleotide H46A(+86+115) [SEQ ID NO:203] showed very strong ability to induce exon 46 skipping. Table 36 below includes antisense molecules tested. These antisense molecules showed varying ability to induce exon 46 skipping.

Antisense Oligonucleotides Directed at Exon 50

Antisense oligonucleotides directed at exon 50 were prepared and tested for their ability to induce exon skipping in human muscle cells using similar methods as described above.

Antisense oligonucleotide molecule H50A(+02+30) [SEQ ID NO: 173] was a strong inducer of exon skipping. Further, H50A(+07+33) [SEQ ID NO:174] and H50D(+07-18) [SEQ ID NO:175] both induced exon 50 skipping when delivered into cells at a concentration of 100 nM.

Antisense Oligonucleotides Directed at Exon 51

Antisense oligonucleotides directed at exon 51 were prepared and tested for their ability to induce exon skipping in human muscle cells using similar methods as described above.

FIG. 22 illustrates differing efficiencies of two antisense molecules directed at exon 51 acceptor splice site. Antisense oligonucleotide H51A(+66+90) [SEQ ID NO:180] showed the stronger ability to induce exon 51 skipping. Table 37 below includes antisense molecules tested at a concentration range of 25, 50, 100, 300 and 600 nM. These antisense molecules showed varying ability to induce exon 51 skipping. The strongest inducers of exon skipping were antisense oligonucleotide H51A(+61+90) [SEQ ID NO: 179] and H51A(+66+95) [SEQ ID NO: 181].

TABLE 36

| SEQ ID | Antisense oligonucleotide name | Sequence | Ability to induce skipping |
|---|---|---|---|
| 168 | H46D (+16-04) | UUA CCU UGA CUU GCU CAA GC | No skipping |
| 169 | H46A (+90+109) | UCC AGG UUC AAG UGG GAU AC | No skipping |
| 203 | H46A (+86+115) | CUC UUU UCC AGG UUC AAG UGG GAU ACU AGC | Good skipping to 100 nM |
| 204 | H46A (+107+137) | CAA GCU UUU CUU UUA GUU GCU GCU CUU UUC C | Good skipping to 100 nM |
| 205 | H46A (−10+20) | UAU UCU UUU GUU CUU CUA GCC UGG AGA AAG | Weak skipping |
| 206 | H46A (+50+77) | CUG CUU CCU CCA ACC AUA AAA CAA AUU C | Weak skipping |

TABLE 37

| SEQ ID | Antisense oligonucleotide name | Sequence | Ability to induce skipping |
|---|---|---|---|
| 176 | H51A (-01+25) | ACC AGA GUA ACA GUC UGA GUA GGA GC | Faint skipping |
| 177 | H51D (+16-07) | CUC AUA CCU UCU GCU UGA UGA UC | Skipping at 300 nM |
| 178 | H51A (+111+134) | UUC UGU CCA AGC CCG GUU GAA AUC | Needs re-testing |
| 179 | H51A (+61+90) | ACA UCA AGG AAG AUG GCA UUU CUA GUU UGG | Very strong skipping |
| 180 | H51A (+66+90) | ACA UCA AGG AAG AUG GCA UUU CUA G | skipping |
| 181 | H51A (+66+95) | CUC CAA CAU CAA GGA AGA UGG CAU UUC UAG | Very strong skipping |
| 182 | H51D (+08-17) | AUC AUU UUU UCU CAU ACC UUC UGC U | No skipping |
| 183 | H51A/D (+08-17) & (-15+?) | AUC AUU UUU UCU CAU ACC UUC UGC UAG GAG CUA AAA | No skipping |
| 184 | H51A (+175+195) | CAC CCA CCA UCA GCC UCU GUG | No skipping |
| 185 | H51A (+199+220) | AUC AUC UCG UUG AUA UCC UCA A | No skipping |

Antisense Oligonucleotides Directed at Exon 52

Antisense oligonucleotides directed at exon 52 were prepared and tested for their ability to induce exon skipping in human muscle cells using similar methods as described above.

FIG. 22 also shows differing efficiencies of four antisense molecules directed at exon 52 acceptor splice site. The most effective antisense oligonucleotide for inducing exon 52 skipping was H52A(+17+37) [SEQ ID NO:188).

Table 38 below shows antisense molecules tested at a concentration range of 50, 100, 300 and 600 nM. These antisense molecules showed varying ability to induce exon 50 skipping. Antisense molecules H52A(+12+41) [SEQ ID NO:187] and H52A(+17+37) [SEQ ID NO:188] showed the strongest exon 50 skipping at a concentration of 50 nM.

Antisense Oligonucleotides Directed at Exon 53

Antisense oligonucleotides directed at exon 53 were prepared and tested for their ability to induce exon skipping in human muscle cells using similar methods as described above.

FIG. 22 also shows antisense molecule H53A(+39+69) [SEQ ID NO:193] directed at exon 53 acceptor splice site. This antisense oligonucleotide was able to induce exon 53 skipping at 5, 100, 300 and 600 nM. A "cocktail" of three exon 53 antisense oligonucleotides: H53A(+23+47) [SEQ ID NO:195], H53A(+150+176) [SEQ ID NO:196] and H53D(+14-07) [SEQ ID NO:194], was also tested, as shown in FIG. 20 and exhibited an ability to induce exon skipping.

Table 39 below includes other antisense molecules tested at a concentration range of 50, 100, 300 and 600 nM. These antisense molecules showed varying ability to induce exon 53 skipping. Antisense molecule H53A(+39+69) [SEQ ID NO:193] induced the strongest exon 53 skipping.

TABLE 38

| SEQ ID | Antisense oligonucleotide name | Sequence | Ability to induce skipping |
|---|---|---|---|
| 186 | H52A (-07+14) | UCC UGC AUU GUU GCC UGU AAG | No skipping |
| 187 | H52A (+12+41) | UCC AAC UGG GGA CGC CUC UGU UCC AAA UCC | Very strong skipping |
| 188 | H52A (+17+37) | ACU GGG GAC GCC UCU GUU CCA | Skipping to 50 nM |
| 189 | H52A (+93+112) | CCG UAA UGA UUG UUC UAG CC | No skipping |
| 190 | H52D (+05-15) | UGU UAA AAA ACU UAC UUC GA | No skipping |

TABLE 39

| SEQ ID | Antisense oligonucleotide name | Sequence | Ability to induce skipping |
|---|---|---|---|
| 191 | H53A (+45+69) | CAU UCA ACU GUU GCC UCC GGU UCU G | Faint skipping at 50 nM |
| 192 | H53A (+39+62) | CUG UUG CCU CCG GUU CUG AAG GUG | Faint skipping at 50 nM |
| 193 | H53A (+39+69) | CAU UCA ACU GUU GCC UCC GGU UCU GAA GGU G | Strong skipping to 50 nM |
| 194 | H53D (+14-07) | UAC UAA CCU UGG UUU CUG UGA | Very faint skipping to 50 nM |
| 195 | H53A (+23+47) | CUG AAG GUG UUC UUG UAC UUC AUC C | Very faint skipping to 50 nM |
| 196 | H53A (+150+176) | UGU AUA GGG ACC CUC CUU CCA UGA CUC | Very faint skipping to 50 nM |
| 197 | H53D (+20-05) | CUA ACC UUG GUU UCU GUG AUU UUC U | Not made yet |
| 198 | H53D (+09-18) | GGU AUC UUU GAU ACU AAC CUU GGU UUC | Faint at 600 nM |
| 199 | H53A (-12+10) | AUU CUU UCA ACU AGA AUA AAA G | No skipping |
| 200 | H53A (-07+18) | GAU UCU GAA UUG UUU CAA CUA GAA U | No skipping |
| 201 | H53A (+07+26) | AUC CCA CUG AUU CUG AAU UC | No skipping |
| 202 | H53A (+124+145) | UUG GCU CUG GCC UGU CCU AAG A | No skipping |

---

What is claimed is:

1. An antisense oligonucleotide of 20 to 31 bases comprising a base sequence that is 100% complementary to consecutive bases of a target region of exon 53 of the human dystrophin pre-mRNA, wherein the target region is within annealing site H53A(+23+47) and annealing site H53A(+39+69), wherein the base sequence comprises at least 12 consecutive bases of CUG AAG GUG UUC UUG UAC UUC AUC C (SEQ ID NO: 195), in which uracil bases are thymine bases, wherein the antisense oligonucleotide is a morpholino antisense oligonucleotide, and wherein the antisense oligonucleotide induces exon 53 skipping; or a pharmaceutically acceptable salt thereof.

2. A pharmaceutical composition comprising: (i) an antisense oligonucleotide of 20 to 31 bases comprising a base sequence that is 100% complementary to consecutive bases of a target region of exon 53 of the human dystrophin pre-mRNA, wherein the target region is within annealing site H53A(+23+47) and annealing site H53A(+39+69), wherein the base sequence comprises at least 12 consecutive bases of CUG AAG GUG UUC UUG UAC UUC AUC C (SEQ ID NO: 195), in which uracil bases are thymine bases, wherein the antisense oligonucleotide is a morpholino antisense oligonucleotide, and wherein the antisense oligonucleotide induces exon 53 skipping, or a pharmaceutically acceptable salt thereof; and (ii) a pharmaceutically acceptable carrier.

* * * * *

UNITED STATES PATENT AND TRADEMARK OFFICE
CERTIFICATE OF CORRECTION

PATENT NO. : 9,994,851 B2  
APPLICATION NO. : 15/705172  
DATED : June 12, 2018  
INVENTOR(S) : Wilton et al.

It is certified that error appears in the above-identified patent and that said Letters Patent is hereby corrected as shown below:

In the Specification

Column 1, Line 26, before "STATEMENT REGARDING SEQUENCE LISTING", insert:
--STATEMENT AS TO FEDERALLY SPONSORED RESEARCH
This invention was made with government support under grant number R01 NS044146 awarded by the National Institutes of Health. The government has certain rights in the invention.--

Signed and Sealed this
Thirty-first Day of July, 2018

Andrei Iancu
*Director of the United States Patent and Trademark Office*

SEQUENCE LISTING

<160> NUMBER OF SEQ ID NOS: 214

<210> SEQ ID NO 1
<211> LENGTH: 24
<212> TYPE: RNA
<213> ORGANISM: Artificial Sequence
<220> FEATURE:
<223> OTHER INFORMATION: Description of Artificial Sequence: Synthetic Human 2'-O-methyl phosphorothioate antisense oligonucleotide

<400> SEQUENCE: 1
gauagguggu aucaacaucu guaa          24

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic Human 2'-O-methyl phosphorothioate antisense oligonucleotide

<400> SEQUENCE: 2
gauagguggu aucaacaucu g          21

<210> SEQ ID NO 3
<211> LENGTH: 25
<212> TYPE: RNA

```
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 3
gauagguggu aucaacaucu guaag                                           25

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 4
ggugguauca acaucuguaa                                                 20

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 5
guaucaacau cuguaagcac                                                 20

<210> SEQ ID NO 6
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 6
ugcauguucc agucguugug ugg                                             23

<210> SEQ ID NO 7
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 7
cacuauucca gucaaauagg ucugg                                           25

<210> SEQ ID NO 8
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 8
auuuaccaac cuucaggauc gagua                                           25
```

```
<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 9
ggccuaaaac acauacacau a                                               21

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
      Canine 2'-O-methyl phosphorothioate antisense
      oligonucleotide

<400> SEQUENCE: 10 cauuuugac cuacaugugg                                                  20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      Canine 2'-O-methyl phosphorothioate antisense
      oligonucleotide

<400> SEQUENCE: 11
uuugaccuac auuggaaag                                                  20

<210> SEQ ID NO 12
<211> LENGTH: 26
<212> TYPE: RNA
<213> ORGANISM: Artificial Sequence
<220> FEATURE:
<223> OTHER INFORMATION: Description of Artificial Sequence: Synthetic
      Canine 2'-O-methyl phosphorothioate antisense
      oligonucleotide

<400> SEQUENCE: 12 uacauuuug accuacaugu ggaaag                                           26

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
      Canine 2'-O-methyl phosphorothioate antisense
      oligonucleotide

<400> SEQUENCE: 13 auuuugacc uacaugggaa ag                                               22

<210> SEQ ID NO 14
<211> LENGTH: 23
<212> TYPE: RNA
<213> ORGANISM: Artificial Sequence
<220> FEATURE:
<223> OTHER INFORMATION: Description of Artificial Sequence: Synthetic
      Canine 2'-O-methyl phosphorothioate antisense
```

-continued oligonucleotide

<400> SEQUENCE: 14
uacgaguuga uugucggacc cag                                              23

<210> SEQ ID NO 15
<211> LENGTH: 25
<212> TYPE: RNA
<213> ORGANISM: Artificial Sequence
<220> FEATURE:
<223> OTHER INFORMATION: Description of Artificial Sequence: Synthetic
      Canine 2'-O-methyl phosphorothioate antisense
      oligonucleotide

<400> SEQUENCE: 15
guggucuccu uaccaugac ugugg                                             25

<210> SEQ ID NO 16
<211> LENGTH: 17
<212> TYPE: RNA
<213> ORGANISM: Artificial Sequence
<220> FEATURE:
<223> OTHER INFORMATION: Description of Artificial Sequence: Synthetic
      Canine 2'-O-methyl phosphorothioate antisense
      oligonucleotide

<400> SEQUENCE: 16
ggucuccuua ccauga                                                      17

<210> SEQ ID NO 17
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 17
ugucucagua aucuucuuac cuau                                             24

<210> SEQ ID NO 18
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 18
ucuuaccuau gacuauggau gaga                                             24

<210> SEQ ID NO 19
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 19
gcaugaacuc uugugggaucc                                                 20

<210> SEQ ID NO 20
<211> LENGTH: 20

```
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 20
ccaggguacu acuuacauua                                                      20

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 21
aucguguguc acagcaucca g                                                    21

<210> SEQ ID NO 22
<211> LENGTH: 30
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 22
uguucagggc augaacucuu guggauccuu                                           30

<210> SEQ ID NO 23
<211> LENGTH: 31
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 23
uaggaggcgc cucccauccu guaggucacu g                                         31

<210> SEQ ID NO 24
<211> LENGTH: 31
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 24
aggucuagga ggcgccuccc auccuguagg u                                         31

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 25
```

```
gcgccuccca uccuguaggu cacug                                          25

<210> SEQ ID NO 26
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 26
cuucgaggag gucuaggagg cgccuc                                         26

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 27
cucccauccu guaggucacu g                                              21

<210> SEQ ID NO 28
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 28
uaccaguuuu ugcccuguca gg                                             22

<210> SEQ ID NO 29
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 29
ucaauaugcu gcuucccaaa cugaaa                                         26

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 30
cuaggaggcg ccucccaucc uguag                                          25

<210> SEQ ID NO 31
<211> LENGTH: 31
<212> TYPE: RNA
<213> ORGANISM: Artificial Sequence
<220> FEATURE:
<223> OTHER INFORMATION: Description of Artificial Sequence: Synthetic
```

Human 2'-O-methyl phosphorothioate antisense
      oligonucleotide

<400> SEQUENCE: 31
uuaugauuuc caucuacgau gucaguacuu c                                         31

<210> SEQ ID NO 32
<211> LENGTH: 31
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 32
cuuaccugcc aguggaggau uauauuccaa a                                         31

<210> SEQ ID NO 33
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 33
caucaggauu cuuaccugcc agugg                                                25

<210> SEQ ID NO 34
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 34
cgaugucagu acuuccaaua uucac                                                25

<210> SEQ ID NO 35
<211> LENGTH: 18
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 35 accaucauc aggauucu                                                         18

<210> SEQ ID NO 36
<211> LENGTH: 18
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 36
accugccagu ggaggauu                                                        18

<210> SEQ ID NO 37

```
<211> LENGTH: 27
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 37
ccaauauuca cuaaaucaac cuguuaa                                            27

<210> SEQ ID NO 38
<211> LENGTH: 30
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 38
caggauucuu accugccagu ggaggauuau                                         30

<210> SEQ ID NO 39
<211> LENGTH: 31
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 39
acgaugucag uacuuccaau auucacuaaa u                                       31

<210> SEQ ID NO 40
<211> LENGTH: 31
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 40
auuuccaucu acgaugucag uacuuccaau a                                       31

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 41
caggagcuuc caaaugcugc a                                                  21

<210> SEQ ID NO 42
<211> LENGTH: 29
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 42
```

```
cuugucuuca ggagcuucca aaugcugca                                         29

<210> SEQ ID NO 43
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 43
uccucagcag aaagaagcca cg                                                22

<210> SEQ ID NO 44
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 44
uuagaaaucu cuccuugugc                                                   20

<210> SEQ ID NO 45
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 45
uaaauugggu guuacacaau                                                   20

<210> SEQ ID NO 46
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 46
cccugaggca uucccaucuu gaau                                              24

<210> SEQ ID NO 47
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 47
aggacuuacu ugcuuuguuu                                                   20

<210> SEQ ID NO 48
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      Human 2'-O-methyl phosphorothioate antisense
      oligonucleotide

<400> SEQUENCE: 48
cuugaauuua ggagauucau cug                                             23

<210> SEQ ID NO 49
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 49
caucuucuga uaauuuuccu guu                                             23

<210> SEQ ID NO 50
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 50
ucuucuguuu uuguuagcca guca                                            24

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 51
ucuauguaaa cugaaaauuu                                                 20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 52
uucuggagau ccauuaaaac                                                 20

<210> SEQ ID NO 53
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 53
cagcaguugc gugaucucca cuag                                            24
```

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 54
uucaucaacu accaccacca u                                            21

<210> SEQ ID NO 55
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 55
cuaagcaaaa uaaucugacc uuaag                                        25

<210> SEQ ID NO 56
<211> LENGTH: 28
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 56
cuuguaaaag aacccagcgg ucuucugu                                     28

<210> SEQ ID NO 57
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 57
caucuacaga uguuugccca uc                                           22

<210> SEQ ID NO 58
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 58
gaaggauguc uuguaaaaga acc                                          23

<210> SEQ ID NO 59
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

```
<400> SEQUENCE: 59
accuguucuu caguaagacg                                              20

<210> SEQ ID NO 60
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 60
caugacacac cuguucuuca guaa                                         24

<210> SEQ ID NO 61
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 61
cauuugagaa ggaugucuug                                              20

<210> SEQ ID NO 62
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 62
aucucccaau accuggagaa gaga                                         24

<210> SEQ ID NO 63
<211> LENGTH: 31
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 63
gccaugcacu aaaaaggcac ugcaagacau u                                 31

<210> SEQ ID NO 64
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 64
ucuuuaaagc caguugugug aauc                                         24

<210> SEQ ID NO 65
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      Human 2'-O-methyl phosphorothioate antisense
      oligonucleotide

<400> SEQUENCE: 65
uuucugaaag ccaugcacua a                                              21

<210> SEQ ID NO 66
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 66
guacauacgg ccaguuuuug aagac                                          25

<210> SEQ ID NO 67
<211> LENGTH: 31
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 67
cuagauccgc uuuuaaaacc uguuaaaaca a                                   31

<210> SEQ ID NO 68
<211> LENGTH: 31
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 68
ucuuuucuag auccgcuuuu aaaaccuguu a                                   31

<210> SEQ ID NO 69
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 69
cuagauccgc uuuuaaaacc uguua                                          25

<210> SEQ ID NO 70
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 70
ccgucuucug ggucacugac uua                                            23
```

<210> SEQ ID NO 71
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 71
cuagauccgc uuuuaaaacc uguuaa                                          26

<210> SEQ ID NO 72
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 72
ccgcuuuuaa aaccuguuaa                                                 20

<210> SEQ ID NO 73
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 73
uggauugcuu uuucuuuucu agaucc                                          26

<210> SEQ ID NO 74
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 74
caugcuuccg ucuucggguu cacug                                           25

<210> SEQ ID NO 75
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 75
gaucuuguuu gagugaauac agu                                             23

<210> SEQ ID NO 76
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

```
<400> SEQUENCE: 76
guuauccagc caugcuuccg uc                                              22

<210> SEQ ID NO 77
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 77
ugauaauugg uaucacuaac cugug                                           25

<210> SEQ ID NO 78
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 78
guaucacuaa ccugugcugu ac                                              22

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 79
cugcuggcau cuugcaguu                                                  19

<210> SEQ ID NO 80
<211> LENGTH: 31
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 80
gccugagcug aucugcuggc aucuugcagu u                                    31

<210> SEQ ID NO 81
<211> LENGTH: 28
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 81
cuggcagaau ucgauccacc ggcuguuc                                        28

<210> SEQ ID NO 82
<211> LENGTH: 22
<212> TYPE: RNA
```

```
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 82
cagcaguagu ugucaucugc uc                                              22

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 83
ugauggggug guggguugg                                                  19

<210> SEQ ID NO 84
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 84
aucugcauua acacccucua gaaag                                           25

<210> SEQ ID NO 85
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 85
ccggcuguuc aguuguucug aggc                                            24

<210> SEQ ID NO 86
<211> LENGTH: 28
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 86
aucugcauua acacccucua gaaagaaa                                        28

<210> SEQ ID NO 87
<211> LENGTH: 28
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 87
gaaggagaag agauucuuac cuuacaaa                                        28
```

<210> SEQ ID NO 88
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 88
auucgaucca ccggcuguuc                                              20

<210> SEQ ID NO 89
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 89
cagcaguagu ugucaucugc                                              20

<210> SEQ ID NO 90
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 90
gccgguugac uucauccugu gc                                           22

<210> SEQ ID NO 91
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 91
cugcauccag gaacaugggu cc                                           22

<210> SEQ ID NO 92
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 92
gucugcaucc aggaacaugg guc                                          23

<210> SEQ ID NO 93
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense oligonucleotide

<400> SEQUENCE: 93
guugaagauc ugauagccgg uuga                                              24

<210> SEQ ID NO 94
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 94
uacuuacugu cuguagcucu uucu                                              24

<210> SEQ ID NO 95
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 95
cacucauggu cuccugauag cgca                                              24

<210> SEQ ID NO 96
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 96
cugcaauucc ccgagucucu gc                                                22

<210> SEQ ID NO 97
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 97
acugcuggac ccauguccug aug                                               23

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 98
cuaaguugag guauggagag u                                                 21

<210> SEQ ID NO 99
<211> LENGTH: 23

```
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 99
uauucacaga ccugcaauuc ccc                                          23

<210> SEQ ID NO 100
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 100
acaguggugc ugagauagua uaggcc                                       26

<210> SEQ ID NO 101
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 101
uaggccacuu uguugcucuu gc                                           22

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 102
uucagagggc gcuuucuuc                                               19

<210> SEQ ID NO 103
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 103
gggcaggcca uuccuccuuc aga                                          23

<210> SEQ ID NO 104
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 104
```
ucuucagggu uuguauguga uucu                     24

<210> SEQ ID NO 105
<211> LENGTH: 27
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 105
cugggcugaa uugucugaau aucacug                  27

<210> SEQ ID NO 106
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 106
cuguuggcac augugauccc acugag                   26

<210> SEQ ID NO 107
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 107
gucuauaccu guuggcacau guga                     24

<210> SEQ ID NO 108
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 108
ugcuuucugu aauucaucug gaguu                    25

<210> SEQ ID NO 109
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 109
ccuccuuucu ggcauagacc uuccac                   26

<210> SEQ ID NO 110
<211> LENGTH: 25
<212> TYPE: RNA
<213> ORGANISM: Artificial Sequence
<220> FEATURE:
<223> OTHER INFORMATION: Description of Artificial Sequence: Synthetic Human 2'-O-methyl phosphorothioate antisense
oligonucleotide

<400> SEQUENCE: 110
ugugucaucc auucgugcau cucug                                          25

<210> SEQ ID NO 111
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 111
uuaaggccuc uugugcuaca ggugg                                          25

<210> SEQ ID NO 112
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 112
gggccucuuc uuuagcucuc uga                                            23

<210> SEQ ID NO 113
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 113
gacuuccaaa gucuugcauu uc                                             22

<210> SEQ ID NO 114
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 114
gccaacaugc ccaaacuucc uaag                                           24

<210> SEQ ID NO 115
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 115
cagagauuuc cucagcuccg ccagga                                         26

<210> SEQ ID NO 116

-continued

```
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 116
cuuacaucua gcaccucaga g                                              21

<210> SEQ ID NO 117
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 117
uccgccaucu guuagggucu gugcc                                          25

<210> SEQ ID NO 118
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 118
auuuggguua uccucugaau gucgc                                          25

<210> SEQ ID NO 119
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 119
cauaccucuu cauguaguuc cc                                             22

<210> SEQ ID NO 120
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 120
cauuugagcu gcguccaccu ugucug                                         26

<210> SEQ ID NO 121
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 121
```

```
uccugggcag acuggaugcu cuguuc                                          26

<210> SEQ ID NO 122
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 122
uugccugggc uuccugaggc auu                                             23

<210> SEQ ID NO 123
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 123
uucugaaaua acauauaccu gugc                                            24

<210> SEQ ID NO 124
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 124
uaguuucuga aauaacauau accug                                           25

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 125
gacuugucaa aucagauugg a                                               21

<210> SEQ ID NO 126
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 126
guuucugaaa uaacauauac cugu                                            24

<210> SEQ ID NO 127
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      Human 2'-O-methyl phosphorothioate antisense
      oligonucleotide

<400> SEQUENCE: 127
caccagaaau acauaccaca                                               20

<210> SEQ ID NO 128
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 128
caaugauuua gcugugacug                                               20

<210> SEQ ID NO 129
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 129
cgaaacuuca uggagacauc uug                                           23

<210> SEQ ID NO 130
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 130
cuuguagacg cugcucaaaa uuggc                                         25

<210> SEQ ID NO 131
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 131
caugcacaca ccuuugcucc                                               20

<210> SEQ ID NO 132
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 132
ucuguacaau cugacgucca gucu                                          24
```

```
<210> SEQ ID NO 133
<211> LENGTH: 27
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 133
gucuuuauca ccauuccac uucagac                                        27

<210> SEQ ID NO 134
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 134
ccgucugcuu uuucuguaca aucug                                         25

<210> SEQ ID NO 135
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 135
uccauaucug uagcugccag cc                                            22

<210> SEQ ID NO 136
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 136
ccaggcaacu ucagaaucca aau                                           23

<210> SEQ ID NO 137
<211> LENGTH: 30
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 137
uuucuguuac cugaaaagaa uuauaaugaa                                    30

<210> SEQ ID NO 138
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide
```

```
<400> SEQUENCE: 138
cauucauuuc cuuucgcauc uuacg                                          25

<210> SEQ ID NO 139
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 139
ugaucucuuu gucaauucca uaucug                                         26

<210> SEQ ID NO 140
<211> LENGTH: 30
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 140
uucagugaua uagguuuuac cuuuccccag                                     30

<210> SEQ ID NO 141
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 141
cuguagcugc cagccauucu gucaag                                         26

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 142
ucuucugcuc gggaggugac a                                              21

<210> SEQ ID NO 143
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 143
ccaguuacua uucagaagac                                                20

<210> SEQ ID NO 144
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      Human 2'-O-methyl phosphorothioate antisense
      oligonucleotide

<400> SEQUENCE: 144
ucuucaggug caccuucugu                                                     20

<210> SEQ ID NO 145
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 145
ugugaugugg uccacauucu gguca                                               25

<210> SEQ ID NO 146
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 146
ccauguguuu cugguauucc                                                     20

<210> SEQ ID NO 147
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 147
cguguagagu ccaccuuugg gcgua                                               25

<210> SEQ ID NO 148
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 148
uacuaauuuc cugcaguggu cacc                                                24

<210> SEQ ID NO 149
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 149
uucuguguga aauggcugca aauc                                                24
```

<210> SEQ ID NO 150
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 150
ccuucaaagg aauggaggcc                                               20

<210> SEQ ID NO 151
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 151
ugcugaauuu cagccuccag ugguu                                         25

<210> SEQ ID NO 152
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 152
ugaagucuuc cucuuucaga uucac                                         25

<210> SEQ ID NO 153
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 153
cuggcuuucu cucaucugug auuc                                          24

<210> SEQ ID NO 154
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense oligonucleotide

<400> SEQUENCE: 154
guuguaaguu gucuccucuu                                               20

<210> SEQ ID NO 155
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide -continued

```
<400> SEQUENCE: 155
uugucuguaa cagcugcugu                                              20

<210> SEQ ID NO 156
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 156
gcucuaauac cuugagagca                                              20

<210> SEQ ID NO 157
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 157
cuuugagacc ucaaauccug uu                                           22

<210> SEQ ID NO 158
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 158 cuuuauuuc cuuucaucuc ugggc                                         25

<210> SEQ ID NO 159
<211> LENGTH: 27
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 159
aucguuucuu cacggacagu gugcugg                                      27

<210> SEQ ID NO 160
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 160
gggcuuguga gacaugagug auuu                                         24

<210> SEQ ID NO 161
<211> LENGTH: 22
<212> TYPE: RNA
<213> ORGANISM: Artificial Sequence
```

```
<220> FEATURE:
<223> OTHER INFORMATION: Description of Artificial Sequence: Synthetic
      Human 2'-O-methyl phosphorothioate antisense
      oligonucleotide

<400> SEQUENCE: 161
accuucagag gacuccucuu gc                                              22

<210> SEQ ID NO 162
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 162
uauguguuac cuacccuugu cgguc                                           25

<210> SEQ ID NO 163
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 163
ggagagagcu uccuguagcu                                                 20

<210> SEQ ID NO 164
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 164
ucacccuuuc cacaggcguu gca                                             23

<210> SEQ ID NO 165
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 165
uuugugucuu ucugagaaac                                                 20

<210> SEQ ID NO 166
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 166
aaagacuuac cuuaagauac                                                 20
```

```
<210> SEQ ID NO 167
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 167
aucugucaaa ucgccugcag                                                  20

<210> SEQ ID NO 168
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 168
uuaccuugac uugcucaagc                                                  20

<210> SEQ ID NO 169
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 169
uccagguuca agugggauac                                                  20

<210> SEQ ID NO 170
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 170
gcucuucugg gcuuauggga gcacu                                            25

<210> SEQ ID NO 171
<211> LENGTH: 27
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 171
accuuuaucc acuggagauu ugucugc                                          27

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide
```

<400> SEQUENCE: 172
uuccaccagu aacugaaaca g                                              21

<210> SEQ ID NO 173
<211> LENGTH: 29
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 173
ccacucagag cucagaucuu cuaacuucc                                      29

<210> SEQ ID NO 174
<211> LENGTH: 27
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 174
cuuccacuca gagcucagau cuucuaa                                        27

<210> SEQ ID NO 175
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 175
gggauccagu auacuuacag gcucc                                          25

<210> SEQ ID NO 176
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 176
accagaguaa cagucugagu aggagc                                         26

<210> SEQ ID NO 177
<211> LENGTH: 23
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 177
cucauaccuu cugcuugaug auc                                            23

<210> SEQ ID NO 178
<211> LENGTH: 24
<212> TYPE: RNA

```
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 178
uucuguccaa gcccgguuga aauc                                              24

<210> SEQ ID NO 179
<211> LENGTH: 30
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 179
acaucaagga agauggcauu ucuaguuugg                                        30

<210> SEQ ID NO 180
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 180
acaucaagga agauggcauu ucuag                                             25

<210> SEQ ID NO 181
<211> LENGTH: 30
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 181
cuccaacauc aaggaagaug gcauuucuag                                        30

<210> SEQ ID NO 182
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 182
aucauuuuuu cucauaccuu cugcu                                             25

<210> SEQ ID NO 183
<211> LENGTH: 36
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 183
aucauuuuuu cucauaccuu cugcuaggag cuaaaa                                 36
```

```
<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 184
cacccaccau cacccucugu g                                              21

<210> SEQ ID NO 185
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 185
aucaucucgu ugauauccuc aa                                             22

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 186
uccugcauug uugccuguaa g                                              21

<210> SEQ ID NO 187
<211> LENGTH: 30
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 187
uccaacuggg gacgccucug uuccaaaucc                                     30

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 188
acuggggacg ccucuguucc a                                              21

<210> SEQ ID NO 189
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
```

```
                                 oligonucleotide

<400> SEQUENCE: 189
ccguaaugau uguucuagcc                                                      20

<210> SEQ ID NO 190
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 190
uguuaaaaaa cuuacuucga                                                      20

<210> SEQ ID NO 191
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 191
cauucaacug uugccuccgg uucug                                                25

<210> SEQ ID NO 192
<211> LENGTH: 24
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 192
cuguugccuc cgguucugaa ggug                                                 24

<210> SEQ ID NO 193
<211> LENGTH: 31
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 193
cauucaacug uugccuccgg uucugaaggu g                                         31

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 194
uacuaaccuu gguuucugug a                                                    21

<210> SEQ ID NO 195
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 195
cugaaggugu ucuuguacuu caucc                                          25

<210> SEQ ID NO 196
<211> LENGTH: 27
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 196
uguauaggga cccuccuucc augacuc                                        27

<210> SEQ ID NO 197
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 197
cuaaccuugg uuucugugau uuucu                                          25

<210> SEQ ID NO 198
<211> LENGTH: 27
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 198
gguaucuuug auacuaaccu ugguuuc                                        27

<210> SEQ ID NO 199
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 199
auucuuucaa cuagaauaaa ag                                             22

<210> SEQ ID NO 200
<211> LENGTH: 25
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 200
```

```
gauucugaau ucuuucaacu agaau                                            25

<210> SEQ ID NO 201
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 201
aucccacuga uucugaauuc                                                  20

<210> SEQ ID NO 202
<211> LENGTH: 22
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 202
uuggcucugg ccuguccuaa ga                                               22

<210> SEQ ID NO 203
<211> LENGTH: 30
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 203
cucuuuucca gguucaagug ggauacuagc                                       30

<210> SEQ ID NO 204
<211> LENGTH: 31
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 204
caagcuuuuc uuuuaguugc ugcucuuuuc c                                     31

<210> SEQ ID NO 205
<211> LENGTH: 30
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 205
uauucuuuug uucuucuagc cuggagaaag                                       30

<210> SEQ ID NO 206
<211> LENGTH: 28
<212> TYPE: RNA
<213> ORGANISM: Artificial Sequence
<220> FEATURE:
<223> OTHER INFORMATION: Description of Artificial Sequence: Synthetic
```

Human 2'-O-methyl phosphorothioate antisense
oligonucleotide

<400> SEQUENCE: 206
cugcuuccuc caaccauaaa acaaauuc                                      28

<210> SEQ ID NO 207
<211> LENGTH: 26
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 207
ccaaugccau ccuggaguuc cuguaa                                        26

<210> SEQ ID NO 208
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 208
uccuguagaa uacuggcauc                                               20

<210> SEQ ID NO 209
<211> LENGTH: 27
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 209
ugcagaccuc cugccaccgc agauuca                                       27

<210> SEQ ID NO 210
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 210
cuaccucuuu uuucugucug                                               20

<210> SEQ ID NO 211
<211> LENGTH: 20
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 211
uguuuuugag gauugcugaa                                               20

<210> SEQ ID NO 212

```
<211> LENGTH: 84
<212> TYPE: RNA
<213> ORGANISM: Artificial Sequence
<220> FEATURE:
<223> OTHER INFORMATION: Description of Artificial Sequence: Synthetic
      Human 2'-O-methyl phosphorothioate antisense
      oligonucleotide

<400> SEQUENCE: 212
cagcaguagu ugucaucugc ucaacuggca gaauucgauc caccggcugu ucaagccuga     60
gcugaucugc ucgcaucuug cagu                                           84

<210> SEQ ID NO 213
<211> LENGTH: 44
<212> TYPE: RNA
<213> ORGANISM: Homo sapiens

<400> SEQUENCE: 213
ucaugcacug agugaccucu uucucgcagg cgcuagcugg agca                      44

<210> SEQ ID NO 214
<211> LENGTH: 22
<212> TYPE: RNA
<213> ORGANISM: Homo sapiens

<400> SEQUENCE: 214
ccgugcagac ugacggucuc au                                              22
```